(12) United States Patent
Panjwani et al.

(10) Patent No.: US 10,226,509 B2
(45) Date of Patent: Mar. 12, 2019

(54) LYMPHANGIOGENESIS INHIBITORS FOR CANCER AND FOR GRAFT SURVIVAL

(71) Applicant: TUFTS UNIVERSITY, Boston, MA (US)

(72) Inventors: Noorjahan Panjwani, Medford, MA (US); Wei-Sheng Chen, Kaohsiung (TW)

(73) Assignee: Tufts University, Boston, MA (US)

( * ) Notice: Subject to any disclaimer, the term of this patent is extended or adjusted under 35 U.S.C. 154(b) by 0 days.

(21) Appl. No.: 15/389,509

(22) Filed: Dec. 23, 2016

(65) Prior Publication Data

US 2017/0202915 A1 Jul. 20, 2017

Related U.S. Application Data

(63) Continuation of application No. PCT/US2015/037641, filed on Jun. 25, 2015.

(60) Provisional application No. 62/016,862, filed on Jun. 25, 2014.

(51) Int. Cl.
| | |
|---|---|
| *A61K 38/17* | (2006.01) |
| *A61K 38/47* | (2006.01) |
| *G01N 33/68* | (2006.01) |
| *A61K 31/702* | (2006.01) |

(52) U.S. Cl.
CPC ........ *A61K 38/1732* (2013.01); *A61K 31/702* (2013.01); *A61K 38/47* (2013.01); *C12Y 302/02029* (2013.01); *G01N 33/6893* (2013.01); *G01N 2333/4724* (2013.01); *G01N 2333/912* (2013.01); *G01N 2800/52* (2013.01)

(58) Field of Classification Search
None
See application file for complete search history.

(56) References Cited

U.S. PATENT DOCUMENTS

| | | |
|---|---|---|
| 2008/0015149 A1 | 1/2008 | Ni et al. |
| 2008/0044385 A1 | 2/2008 | Nishi et al. |

FOREIGN PATENT DOCUMENTS

| | | |
|---|---|---|
| WO | 2014078655 A1 | 5/2014 |

OTHER PUBLICATIONS

Navarro, A et al. Polarized migration of lymphatic endothelial cells is critically dependent on podoplanin regulation of Cdc42. 2011, Am J Physiol Lung Cell Mol Physiol 300:L32-42.
Navarro, A et al. T1alphaipodoplanin is essential for capillary morphogenesis in lymphatic endothelial cells. 2008, Am J Physiol Lung Cell Mol Physiol 295:L543-551.
Offner, H et al. Recombinant human beta-galactoside binding lectin suppresses clinical and histological signs of experimental autoimmune encephalomyelitis. 1990, J. Neuroimmunol. 28:177-84.
Panjwani, N et al. Localization of lectin binding sites in human, cat, and rabbit corneas. 1986, Invest Ophthalmol Vis Sci 27:1280-1284.
Partridge, EA et al. Regulation of cytokine receptors by Golgi N-glycan processing and endocytosis. 2004, Science 306:120-124.
Pytowski, B et al. Complete and specific inhibition of adult lymphatic regeneration by a novel VEGFR-3 neutralizing antibody. 2005, J Natl Cancer Inst 97:14-21.
Rabinovich, GA et al. Functions of cell surface galectin-glycoprotein lattices. 2007, Curr Opin Struct Biol 17:513-520.
Raz, A et al. Evidence for the role of 34-kDa galactoside-binding lectin in transformation and metastasis. 1990, Int. J. Cancer 46:871-7.
Reynolds, AR. Potential relevance of bell-shaped and u-shaped dose-responses for the therapeutic targeting of angiogenesis in cancer 2010, Dose Response 8:253-284.
Rogers, MS, et al. The mouse cornea micropocket angiogenesis assay. 2007, Nat Protoc 2:2545-2550.
Saad, RS, et al. Lymphatic microvessel density as prognostic marker in colorectal cancer 2006, Mod Pathol 19:1317-1323.
Saravanan, C et al. Galectin-3 promotes lamellipodia formation in epithelial cells by interacting with complex N-glycans on alpha3beta1 integrin. 2009, J Cell Sci 122:3684-3693.
Sato, S et al. Binding specificity of a baby hamster kidney lectin for H type I and II chains, polylactosamine glycans, and appropriately glycosylated forms of laminin and fibronectin 1992, J. Biol. Chem. 267:6983-90.
Schacht, V et al. T1alpha/podoplanin deficiency disrupts normal lymphatic vasculature formation and causes lymphedema. 2003, EMBO J 22:3546-3556.
Schoppmann, SF et al. Prognostic value of lymphangiogenesis and lymphovascular invasion in invasive breast cancer 2004, Ann Surg 240:306-312.
Seetharaman, J et al. X-ray crystal structure of the human galectin-3 carbohydrate recognition domain at 2.1-A resolution. 1998 J. Biol. Chem. 273:13047-52.
Seguin, L et al. An integrin $\beta_3$-KRAS-RalB complex drives tumour stemness and resistance to EGFR inhibition. 2014. Nat Cell Biol 16(5):457-68.
Sharon, N. Lectin-carbohydrate complexes of plants and animals: an atomic view. 1993, Trends Biochem. Sci. 18: 221-226.
Singh, N et al. Soluble vascular endothelial growth factor receptor 3 is essential for corneal alymphaticity. 2013, Blood 121:4242-4249.
Skobe, M et al. Blocking the path of lymphatic vessels. 2009, Nat Med 15:993-994.

(Continued)

*Primary Examiner* — Layla D Berry
(74) *Attorney, Agent, or Firm* — Sonia K. Guterman; Preeti T. Arun; Lawson & Weitzen, LLP

(57) ABSTRACT

Compositions and methods are provided for treating and/or preventing lymphangiogenesis in a subject by using an inhibitor of a galectin-8 protein in an amount effective to inhibit or to modulate an activity of the galectin-8 protein or a portion thereof sufficient to inhibit the lymphangiogenesis associated with cancer, corneal injury, dry eye disease, inflammation, lymphedema, organ rejection or graft rejection.

7 Claims, 39 Drawing Sheets

Specification includes a Sequence Listing.

(56) References Cited

OTHER PUBLICATIONS

Sonnhammer, ELL et al. Pfam 3.1: 1313 multiple alignments and profile HMMs match the majority of proteins. 1999, Nucleic Acids Res. 27(1): 260-262.
Stillman, BN et al. Galectin-3 and galectin-1 bind distinct cell surface glycoprotein receptors to induce T cell death. 2006, J Immunol 176:778-789.
Stultz, CM et al. Structural analysis based on state-space modeling. 1993, Protein Sci. 2:305-14.
Suryawanshi, A et al. Galectin-1-mediated suppression of Pseudomonas aeruginosa-induced corneal Immunopathology. 2013, J Immunol 190:6397-6409.
Szuba, A et al. Lymphedema: classification, diagnosis and therapy. 1998, Vasc Med 3:145-156.
Veikkola, T et al. Signalling via vascular endothelial growth factor receptor-3 is sufficient for lymphangiogenesis in transgenic mice. 2001, EMBO J 20:1223-1231.
Wang, JF et al. Stimulation of beta 1 integrin induces tyrosine phosphorylation of vascular endothelial growth factor receptor-3 and modulates cell migration. 2001, Journal of biological chemistry 276, 41950-41957.
Wells, V et al. Identification of an autocrine negative growth factor: mouse beta-galactoside-binding protein is a cytostatic factor and cell growth regulator. 1991, Cell 64:91-97.
Wirzenius, M et al. Distinct vascular endothelial growth factor signals for lymphatic vessel enlargement and sprouting. 2007, Journal of experimental medicine 204, 1431-1440.
Witte, MH et al. Lymphangiogenesis and hemangiogenesis: potential targets for therapy. 2011, J Surg Oncol 103:489-500.
Yang, RY et al. Role of the carboxyl-terminal lectin domain in self-association of galectin-3. 1998, Biochemistry 37:4086-4092.
Zeng, Y et al. Lymphatic vessel density and lymph node metastasis in prostate cancer. 2005, Prostate 65:222-230.
Zhang, X et al. Extracellular matrix regulates endothelial functions through interaction of VEGFR-3 and integrin alpha5beta1. 2005, Journal of cellular physiology 202, 205-214.
International Search Report and Written Opinion of the International Searching Authority dated Oct. 6, 2015, in PCT/US2015/037641 (13 pgs.).
Yu, J et al. Slit2N and Robo4 regulate lymphangiogenesis through the VEGF-C/VEGFR-3 pathway. 2014, Cell Communication and Signalling, vol. 12. No. 25, pp. 1-15.
Alitalo, K et al. Review Article Lymphangiogenesis in development and human disease. 2005 Nature 438:946-953.
Bando, H et al. Immunodetection and quantification of vascular endothelial growth factor receptor-3 in human malignant tumor tissues. 2004 Int J Cancer 111:184-191.
Barondes, SH et al. Galectins. Structure and function of a large family of animal lectins. 1994, J. Biol. Chem. 269:20807-10.
Breiteneder-Geleff, S et al. Podoplanin, novel 43-kd membrane protein of glomerular epithelial cells, is down-regulated in puromycin nephrosis. 1997, Am J Pathol 151:1141-1152.
Brorson, H et al. Controlled compression and liposuction treatment for lower extremity lymphedema. 2008, Lymphology 41:52-63.
Cao, R et al. Mouse corneal lymphangiogenesis model. 2011, Nat Protoc 6:817-826.
Carlsson, S et al. Affinity of galectin-8 and its carbohydrate recognition domains for ligands in solution and at the cell surface. 2007 Glycobiology 17:663-676.
Carlsson, S et al. Intracellular sorting of galectin-8 based on carbohydrate fine specificity. 2007 Glycobiology 17:906-912.
Chen, J et al. Integrins and Their Extracellular Matrix Ligands in Lymphangiogenesis and Lymph Node Metastasis 2012. International journal of cell biology. 2012, 853703 (12 pgs.).
Chen, W et al. Pathological Lymphangiogenesis Is Regulated by Galectin-8-Dependent Crosstalk among VEGF-C, Podoplanin and Integrin Pathways. 2015 FASEB J 29:890.6 (1 pg.).
Cho, YK et al. Vascular Endothelial Growth Factor Receptor 1 Morpholino Decreases Angiogenesis in a Murine Corneal Suture Model. 2012, Invest Ophthalmol Vis Sci 53:685-692.
Choi, I et al. Visualization of lymphatic vessels by Prox1-promoter directed GFP reporter in a bacterial artificial chromosome-based transgenic mouse. 2011, Blood 117:362-365.
Cooper, DNW et al. Endogenous muscle lectin inhibits myoblast adhesion to laminin. 1991, J. Cell Biol. 115:1437-1447.
Cueni, LN et al. Galectin-8 interacts with podoplanin and modulates lymphatic endothelial cell functions. 2009, Exp Cell Res 315:1715-1723.
Cueni, LN et al. Podoplanin-Fc reduces lymphatic vessel formation in vitro and in vivo and causes disseminated intravascular coagulation when transgenically expressed in the skin. 2010, Blood 116, 4376-4384.
Cursiefen, C et al. Roles of thrombospondin-1 and -2 in regulating corneal and iris angiogenesis. 2004 Invest Ophthalmol Vis Sci 45:1117-1124.
Dietrich, T et al. Cutting Edge: Lymphatic Vessels, Not Blood Vessels, Primarily Mediate Immune Rejections After Transplantation. 2010, J Immunol 184:535-539.
Diskin, S et al. The role of integrin glycosylation in galectin-8-mediated trabecular meshwork cell adhesion and spreading. 2009, Glycobiology 19:29-37.
Flister, MJ et al. Inflammation induces lymphangiogenesis through up-regulation of VEGFR-3 mediated by NF-κb and Prox1. 2010, Blood 115:418-429.
Fu, J et al. Endothelial cell O-glycan deficiency causes blood/lymphatic misconnections and consequent fatty liver disease in mice. 2008, J Clin Invest 118:3725-3737.
Garner, OB et al. Galectin-glycan lattices regulate cell-surface glycoprotein organization and signalling. Biochemical Society Transactions. 2008, Biochemical Society transactions 36, 1472-1477.
Goyal, S et al. Evidence of corneal lymphangiogenesis in dry eye disease: a potential link to adaptive immunity? 2010, Arch Ophthalmol 128:819-824.
Gribskov, M et al. Profile Analysis. 1990, Meth. Enzymol. 183:146-159.
Hadari, YR et al. Galectin-8: on the road from structure to function. 1997, Trends in Glycosci and Glycotechnol. 9: 103-112.
Hall, FT et al. Intratumoral lymphatics and lymph node metastases in papillary thyroid carcinoma. 2003, Arch Otolaryngol Head Neck Surg 129:716-719.
Henrick, K et al., Evidence for subsites in the galectins involved in sugar binding at the nonreducing end of the central galactose of oligosaccharide ligands: sequence analysis, homology modeling and mutagenesis studies of hamster galectin-3. 1998, Glycobiology 8:45-47.
Herzog, BH et al. Podoplanin maintains high endothelial venule integrity by interacting with platelet CLEC-2. 2013, Nature 502:105-109.
Hughes, RC. Lectins as cell adhesion molecules. 1992, Curr. Opin. Struct. Biol., 2 pp. 687-692.
Ideo, H et al. Galectin-8-N-domain recognition mechanism for sialylated and sulfated glycans. 2011, J Biol Chem 286:11346-11355.
Ideo, H et al. The N-terminal carbohydrate recognition domain of galectin-8 recognizes specific glycosphingolipids with high affinity. 2003, Glycobiology 13:713-723.
Jeltsch, M et al. Hyperplasia of lymphatic vessels in VEGF-C transgenic mice. 1997, Science 276:1423-1425.
John, CM, et al. Truncated galectin-3 inhibits tumor growth and metastasis in orthotopic nude mouse model of human breast cancer. 2003, Clin Cancer Res 9:2374-2383.
Joukov, V. et al. Proteolytic processing regulates receptor specificity and activity of VEGF-C. 1997, EMBO journal 16, 3898-3911.
Kaneko MK, et al. Functional glycosylation of human podoplanin: glycan structure of platelet aggregation-inducing factor. 2007. FEBS Lett 581:331-336.
Karaman, S et al. Mechanisms of lymphatic metastasis. 2014, J Clin Invest 124:922-928.
Karkkainen, MJ, et al. Vascular endothelial growth factor C is required for sprouting of the first lymphatic vessels from embryonic veins. 2004, Nat Immunol 5:74-80.
Kim, H et al. Inflammation-associated lymphangiogenesis: a double-edged sword? 2014, J Clin Invest 124:936-942.

(56) References Cited

OTHER PUBLICATIONS kuwabara, I et al. Galectin-7 (PIG1) exhibits pro-apoptotic function through JNK activation and mitochondrial cytochrome c release. 2002, J Biol Chem 277:3487-3497.

Lajoie P. et al. Lattices, rafts, and scaffolds: domain regulation of receptor signaling at the plasma membrane. 2009, J Cell Biol 185:381-385.

Levy, Y et al. It depends on the hinge: a structure-functional analysis of galectin-8, a tandem-repeat type lectin. 2006, Glycobiology 16:463-476.

Lobsanov, YD et al. X-ray Crystal Structure of the Human Dimeric S-Lac Lectin, L-14-11, in Complex with Lactose at 2.9-A Resolution. 1993, J. Biol. Chem. 267:27034-38.

Maby-El Hajjami, H et al. Developmental and pathological lymphangiogenesis: from models to human disease. 2008, Histochem Cell Biol 130:1063-107.

Machnik, A et al. Macrophages regulate salt-dependent volume and blood pressure by a vascular endothelial growth factor-C-dependent buffering mechanism. 2009, Nat Med 15:545-552.

Markowska, AI et al. Galectin-3 is an important mediator of VEGF- and bFGF-mediated angiogenic response. 2010, J Exp Med 207:1981-1993.

Markowska, AI et al. Galectin-3 protein modulates cell surface expression and activation of vascular endothelial growth factor receptor 2 in human endothelial cells. 2011, J Biol Chem 286:29913-29921.

Matsumoto, M et al. Signaling for lymphangiogenesis via VEGFR-3 is required for the early events of metastasis. 2013, Clin Exp Metastasis 30:819-832.

Maula, SM et al. Intratumoral lymphatics are essential for the metastatic spread and prognosis in squamous cell carcinomas of the head and neck region. 2003, Cancer Res 63:1920-1926.

Miyata, Y et al. Tumor lymphangiogenesis in transitional cell carcinoma of the upper urinary tract: association with clinicopathological features and prognosis. 2006, J Urol 176:348-353.

Mortimer, PS et al. New developments in clinical aspects of lymphatic disease. 2014, J Clin Invest 124:915-921.

Murakami, M et al. VEGFR1 tyrosine kinase signaling promotes lymphangiogenesis as well as angiogenesis indirectly via macrophage recruitment 2008, Arterioschl. Thromb. Vasc. Biol. 28 (4): 658-664.

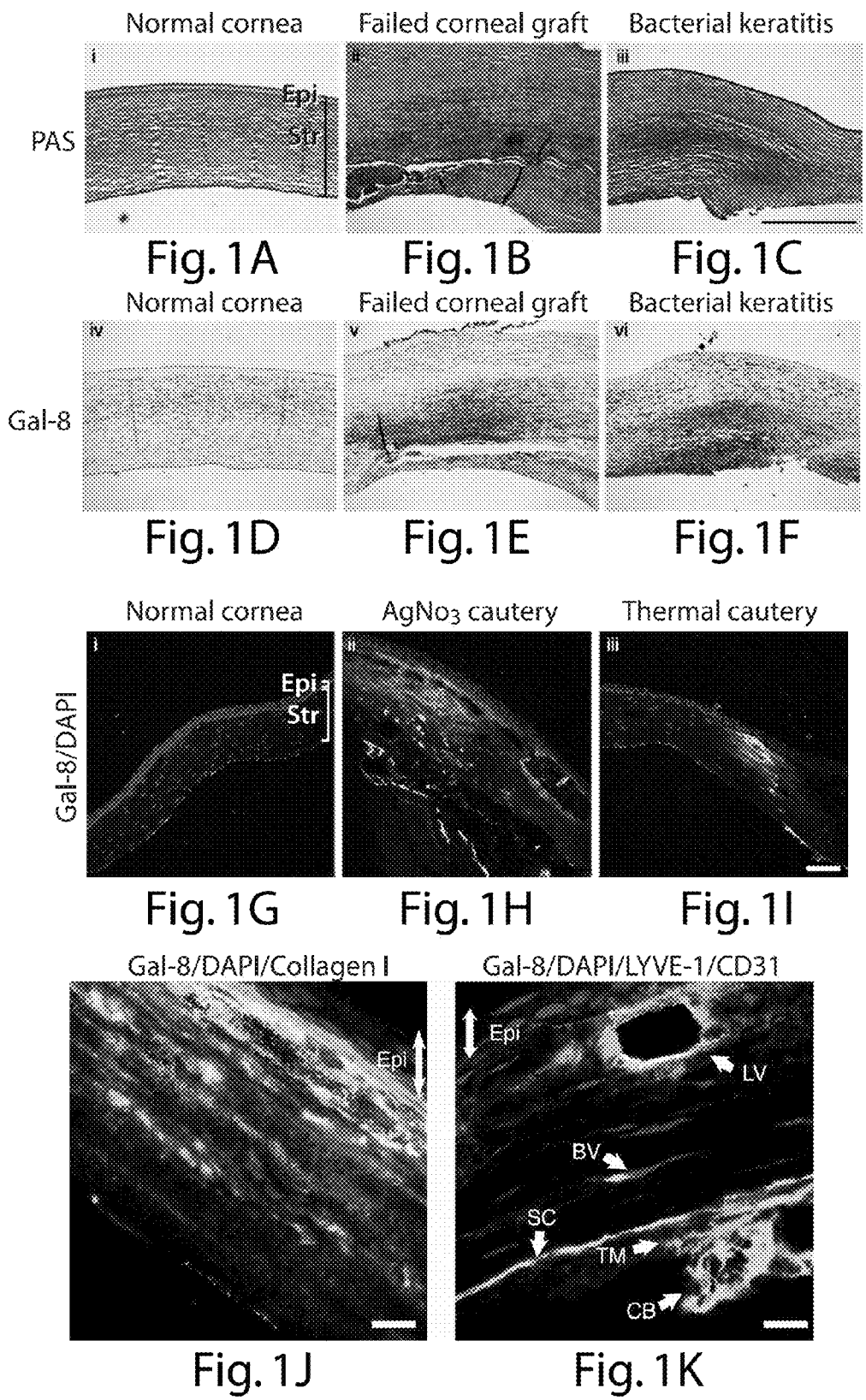

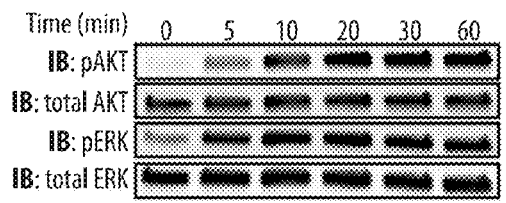 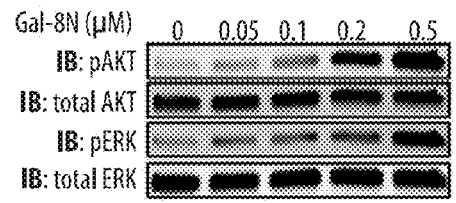
Fig. 3A    Fig. 3B
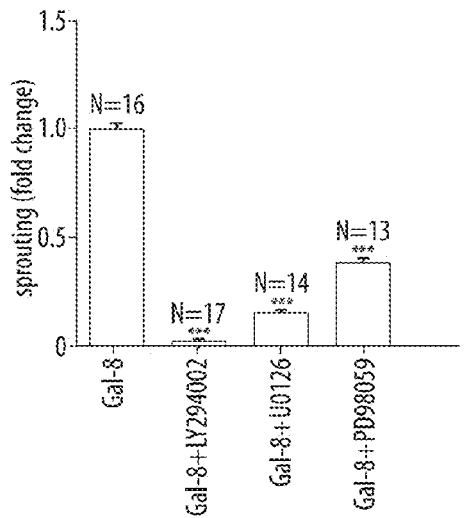 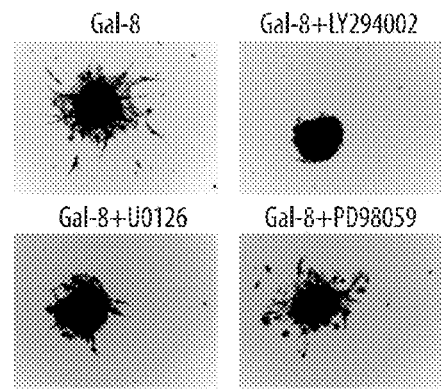
Fig. 3C    Fig. 3D
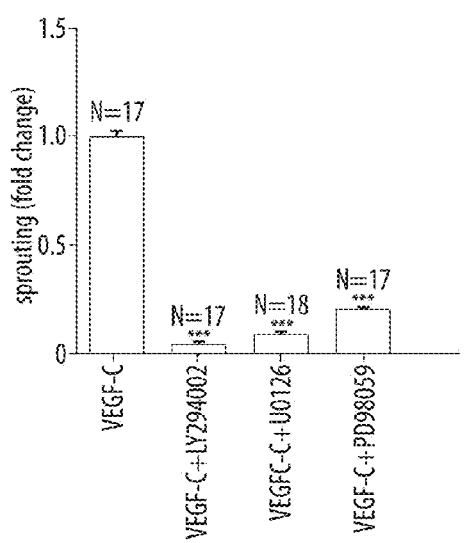 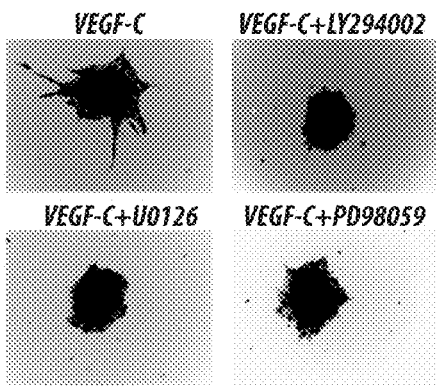
Fig. 3E    Fig. 3F

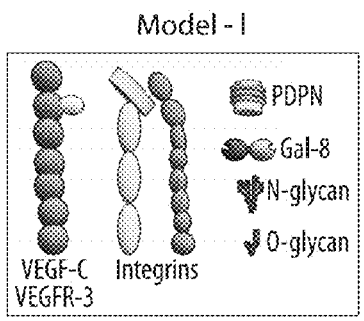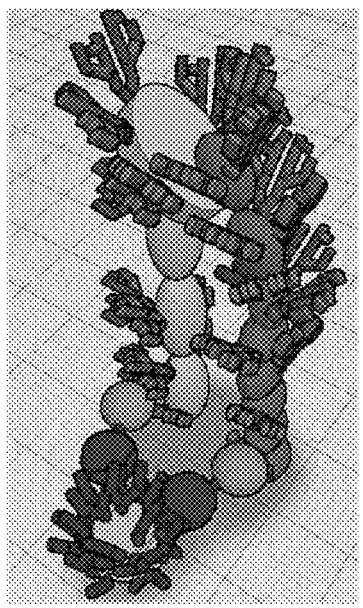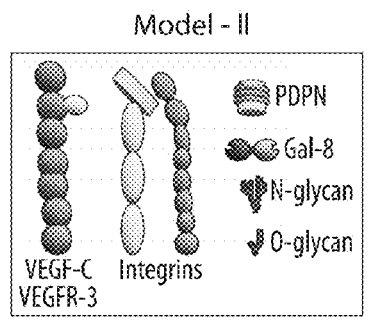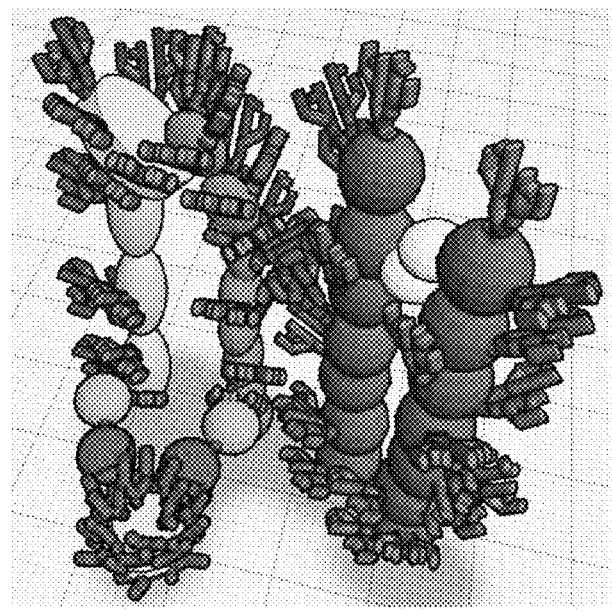
Fig. 16A    Fig. 16B

SEQUENCE LISTING

```
<160> NUMBER OF SEQ ID NOS: 2

<210> SEQ ID NO 1
<211> LENGTH: 316
<212> TYPE: PRT
<213> ORGANISM: Homo sapiens

<400> SEQUENCE: 1

Met Leu Ser Leu Asn Asn Leu Gln Asn Ile Ile Tyr Asn Pro Val Ile
1               5                   10                  15

Pro Tyr Val Gly Thr Ile Pro Asp Gln Leu Asp Pro Gly Thr Leu Ile
            20                  25                  30
```

-continued

```
Val Ile Cys Gly His Val Pro Ser Asp Ala Asp Arg Phe Gln Val Asp
         35                  40                  45
Leu Gln Asn Gly Ser Ser Val Lys Pro Arg Ala Asp Val Ala Phe His
 50                  55                  60
Phe Asn Pro Arg Phe Lys Arg Ala Gly Cys Ile Val Cys Asn Thr Leu
 65                  70                  75                  80
Ile Asn Glu Lys Trp Gly Arg Glu Glu Ile Thr Tyr Asp Thr Pro Phe
                 85                  90                  95
Lys Arg Glu Lys Ser Phe Glu Ile Ile Met Val Leu Lys Asp Lys
                100                 105                 110
Phe Gln Val Ala Val Asn Gly Lys His Thr Leu Leu Tyr Gly His Arg
                115                 120                 125
Ile Gly Pro Glu Lys Ile Asp Thr Leu Gly Ile Tyr Gly Lys Val Asn
130                 135                 140
Ile His Ser Ile Gly Phe Ser Phe Ser Ser Asp Leu Gln Ser Thr Gln
145                 150                 155                 160
Ala Ser Ser Leu Glu Leu Thr Glu Ile Ser Arg Glu Asn Val Pro Lys
                165                 170                 175
Ser Gly Thr Pro Gln Leu Ser Leu Pro Phe Ala Ala Arg Leu Asn Thr
                180                 185                 190
Pro Met Gly Pro Gly Arg Thr Val Val Lys Gly Glu Val Asn Ala
                195                 200                 205
Asn Ala Lys Ser Phe Asn Val Asp Leu Leu Ala Gly Lys Ser Lys Asp
                210                 215                 220
Ile Ala Leu His Leu Asn Pro Arg Leu Asn Ile Lys Ala Phe Val Arg
225                 230                 235                 240
Asn Ser Phe Leu Gln Glu Ser Trp Gly Glu Glu Arg Asn Ile Thr
                245                 250                 255
Ser Phe Pro Phe Ser Pro Gly Met Tyr Phe Glu Met Ile Ile Tyr Cys
                260                 265                 270
Asp Val Arg Glu Phe Lys Val Ala Val Asn Gly Val His Ser Leu Glu
                275                 280                 285
Tyr Lys His Arg Phe Lys Glu Leu Ser Ser Ile Asp Thr Leu Glu Ile
                290                 295                 300
Asn Gly Asp Ile His Leu Leu Glu Val Arg Ser Trp
305                 310                 315

<210> SEQ ID NO 2
<211> LENGTH: 359
<212> TYPE: PRT
<213> ORGANISM: Homo sapiens

<400> SEQUENCE: 2

Met Met Leu Ser Leu Asn Asn Leu Gln Asn Ile Ile Tyr Ser Pro Val
 1               5                  10                  15
Ile Pro Tyr Val Gly Thr Ile Pro Asp Gln Leu Asp Pro Gly Thr Leu
                 20                  25                  30
Ile Val Ile Cys Gly His Val Pro Ser Asp Ala Asp Arg Phe Gln Val
                 35                  40                  45
Asp Leu Gln Asn Gly Ser Ser Val Lys Pro Arg Ala Asp Val Ala Phe
 50                  55                  60
His Phe Asn Pro Arg Phe Lys Arg Ala Gly Cys Ile Val Cys Asn Thr
 65                  70                  75                  80
Leu Ile Asn Glu Lys Trp Gly Arg Glu Glu Ile Thr Tyr Asp Thr Pro
                 85                  90                  95
```

-continued

```
Phe Lys Arg Glu Lys Ser Phe Glu Ile Val Ile Met Val Leu Lys Asp
            100                 105                 110
Lys Phe Gln Val Ala Val Asn Gly Lys His Thr Leu Leu Tyr Gly His
            115                 120                 125
Arg Ile Gly Pro Glu Lys Ile Asp Thr Leu Gly Ile Tyr Gly Lys Val
130                 135                 140
Asn Ile His Ser Ile Gly Phe Ser Phe Ser Ser Asp Leu Gln Ser Thr
145                 150                 155                 160
Gln Ala Ser Ser Leu Glu Leu Thr Glu Ile Ser Arg Glu Asn Val Pro
            165                 170                 175
Lys Ser Gly Thr Pro Gln Leu Pro Ser Asn Arg Gly Gly Asp Ile Ser
            180                 185                 190
Lys Ile Ala Pro Arg Thr Val Tyr Thr Lys Ser Lys Asp Ser Thr Val
            195                 200                 205
Asn His Thr Leu Thr Cys Thr Lys Ile Pro Pro Thr Asn Tyr Val Ser
            210                 215                 220
Lys Ile Leu Pro Phe Ala Ala Arg Leu Asn Thr Pro Met Gly Pro Gly
225                 230                 235                 240
Gly Thr Val Val Val Lys Gly Glu Val Asn Ala Asn Ala Lys Ser Phe
            245                 250                 255
Asn Val Asp Leu Leu Ala Gly Lys Ser Lys His Ile Ala Leu His Leu
            260                 265                 270
Asn Pro Arg Leu Asn Ile Lys Ala Phe Val Arg Asn Ser Phe Leu Gln
            275                 280                 285
Glu Ser Trp Gly Glu Glu Arg Asn Ile Thr Ser Phe Pro Phe Ser
            290                 295                 300
Pro Gly Met Tyr Phe Glu Met Ile Ile Tyr Cys Asp Val Arg Glu Phe
305                 310                 315                 320
Lys Val Ala Val Asn Gly Val His Ser Leu Glu Tyr Lys His Arg Phe
            325                 330                 335
Lys Glu Leu Ser Ser Ile Asp Thr Leu Glu Ile Asn Gly Asp Ile His
            340                 345                 350
Leu Leu Glu Val Arg Ser Trp
            355
```

LYMPHANGIOGENESIS INHIBITORS FOR CANCER AND FOR GRAFT SURVIVAL

RELATED APPLICATIONS

This application claims the benefit of international application serial number PCT/US2015/037641 filed Jun. 25, 2015, which claims the benefit of U.S. provisional application ser. no. 62/016,862 filed Jun. 25, 2014 entitled,"Lymphangiogenesis inhibitors for cancer and for graft survival", inventors Noorjahan Panjwani and Wei-Sheng Chen, each of which is hereby incorporated by reference herein in its entirety.

GOVERNMENT SUPPORT

This invention was made with government support under grants R01EY007088, R01EY009349 awarded by the National Eye Institute. The government has certain rights in the invention.

TECHNICAL FIELD

The present invention generally relates to compositions and methods to prevent or treat lymphangiogenesis associated with cancer, inflammation and graft rejection.

BACKGROUND

Lymphangiogenesis is the formation of new lymphatic vessels from preexisting lymphatic vessels and is associated with diverse pathological conditions including metastatic dissemination, graft rejection (e.g. cornea, kidney and heart), type 2 diabetes, obesity, hypertension, and lymphedema (Alitalo, K., et al. 2005. *Nature* 438:946-953; Karaman, S., et al. 2014. *J Clin Invest* 124:922-928; Kim, H., et al. 2014. *J Clin Invest* 124:936-942; Maby-El Hajjami, H., et al. 2008. *Histochem Cell Biol* 130:1063-107; Machnik, A., et al. 2009. *Nat Med* 15:545-552; Mortimer, P. S., et al. 2014. *J Clin Invest* 124:915-921; Skobe, M., et al. 2009. *Nat Med* 15:993-994).

Lymphatic vessel invasion in and around a primary tumor compared to invasion of blood vessels is a prognostic marker of the aggressiveness of various types of cancers. Growth of lymphatic vessels is also involved in graft rejection (Dietrich, T., et al. 2010. *J Immunol* 184:535-539; Hall, F. T., et al. 2003. *Arch Otolaryngol Head Neck Surg* 129: 716-719; Maula, S. M., et al. 2003. *Cancer Res* 63:1920-1926; Miyata, Y., et al. 2006. *J Urol* 176:348-353; Saad, R. S., et al. 2006. *Mod Pathol* 19:1317-1323; Schoppmann, S. F., et al. 2004. *Ann Surg* 240:306-312; Zeng, Y., et al. 2005. *Prostate* 65:222-230).

A regulatory protein that induces lymphangiogenesis is a tyrosine kinase receptor identified as vascular endothelial growth factor receptor-3 (VEGFR-3), which is highly expressed in lymphatic endothelial cells (LECs) and is further upregulated in response to inflammation (Flister, M. J., et al. 2010. *Blood* 115:418-429). That VEGFR-3 plays a central role in lymphangiogenesis has been demonstrated by showing a reduction in lymphatic vessel density following VEGFR-3 blockade during a variety of pathological conditions including malignancy and chronic inflammation (Matsumoto, M., et al. 2013. *Clin Exp Metastasis* 30:819-832; Pytowski, B., et al. 2005. *J Natl Cancer Inst* 97:14-21; Singh, N., et al. 2013. *Blood* 121:4242-4249).

Podoplanin (PDPN), first detected on the surface of podocytes, is a transmembrane receptor protein (Breiteneder-Geleff, S., et al. 1997. *Am J Pathol* 151:1141-1152). PDPN is expressed by LECs but not by blood endothelial cells and promotes blood-lymph separation during development. Mice lacking PDPN have leaky lymphatic vessels and congenital lymphedema (Fu, J., et al. 2008. *J Clin Invest* 118:3725-3737; Schacht, V., et al. 2003. *Embo J* 22:3546-3556). PDPN expression in LECs is required for lymphatic capillary tubule formation in matrigel a VEGF-A-induced cell migration in scratch wound assays (Navarro, A., et al. 2008. *Am J Physiol Lung Cell Mol Physiol* 295:L543-551; Navarro, A., et al. 2011. *Am J Physiol Lung Cell Mol Physiol* 300:L32-42). The extracellular domain of PDPN plays a critical role in lymphangiogenesis. The Fc fusion protein of PDPN extracellular domain (PDPN-Fc) inhibits LEC migration and tube formation in cell culture and suppresses lymphangiogenesis but not hemangiogenesis in inflamed mouse corneas in vivo (Cueni, L. N., et al. 2010. *Blood* 116:4376-4384). These results indicate a requirement of PDPN in lymphangiogenic process. The extracellular domain of PDPN is heavily glycosylated, and O-glycosylation and sialylation are involved in PDPN-mediated blood-lymph separation and platelet aggregation (Fu, J., et al. 2008. *J Clin Invest* 118:3725-3737; Kaneko, M. K., et al. 2007. *FEBS Lett* 581:331-336).

Members of the galectin family of mammalian lectins characterized by a carbohydrate recognition domain (CRD) with affinity for β-galactoside containing glycans, play a role in hemangiogenesis. A galectin family member, Gal-3, modulates VEGF-induced angiogenic response by binding through its CRD to the N-glycans of αvβ3 integrin and VEGFR-2 and subsequently activating angiogenic signaling pathways (Markowska, A. I., et al. 2011. *J Biol Chem* 286:29913-29921; Markowska, A. I., et al. 2010. *J Exp Med* 207:1981-1993). VEGFR-3 and PDPN are glycosylated similarly to most cell receptors. However, little is known about the function of the galectins in the context of the carbohydrate-mediated recognition system. Gal-8 is a tandem-repeat type member of galectin family and contains two different CRDs. The N-terminal CRD (Gal-8N) prefers α2,3-sialyl glycans and mainly contributes to unique carbohydrate-binding specificity of this protein (Carlsson, S., et al. 2007. *Glycobiology* 17:663-676; Ideo, H., et al. 2011. *J Biol Chem* 286:11346-11355; Ideo, H., et al. 2003. *Glycobiology* 13:713-723). Gal-8 is robustly expressed by LECs, binds to PDPN, and promotes LEC haptotactic migration when immobilized on to a surface (Cueni, L. N., et al. 2009. *Exp Cell Res* 315:1715-1723 and Detmar, 2009).

Anti-lymphangiogenic agents are useful for treatment of debilitating diseases of the eye. The growth of lymphatic vessels is the major reason of corneal graft rejection (Dietrich, T., et al. 2010. *J Immunol* 184:535-539). Penetrating keratoplasty is the most common form of solid tissue transplantation. Approximately 40,000 corneal transplantations are performed each year in the United States. Success rate of penetrating keratoplasty is as high as 90% for uncomplicated first grafts performed in avascular low-risk beds. However, the rejection rate of the corneal grafts placed in high-risk vascularized host beds is extremely high (70% to 90%). Thus the development of safe and targeted new regimens to inhibit lymphangiogenesis is needed to promote graft survival.

Anti-lymphangiogenesis drugs are useful also for treatment of dry eye disease. Significant upregulation of pro-lymphangiogenic factors (e.g. VEGF-C, VEGF-D, and VEGFR-3) and selective growth of lymphatic vessels without concurrent growth of blood vessels has been demonstrated in corneas with dry eye disease (Goyal, S., et al.

2010. *Arch Ophthalmol* 128:819-824). Dry eye disease is an immune-mediated disorder affecting about 5 million Americans. It severely impacts the vision-related quality of life and the symptoms can be debilitating. The current therapeutic options for dry eye disease are limited, mostly palliative, and expensive. Therefore, development of lymphangiogenesis inhibitors is of therapeutic value for treatment of dry eye disease.

Moreover, there is need for development of pro-lymphangiogenic therapy for disorders such as lymphedema, a condition of localized fluid retention caused by a compromised lymphatic system. Lymphedema affects approximately 140 million people worldwide (Brorson, H., et al. 2008. *Lymphology* 41:52-63). The disease most frequently occurs after surgical removal of lymph nodes or radiation therapy, during the treatment of cancer. It is a progressive and lifelong complication notably of breast cancer for which no curative treatment exists (Szuba, A., et al. 1998. *Vasc Med* 3:145-156; Witte, M. H., et al. 2011. *J Surg Oncol* 103:489-500). Despite the well-established significance of lymphatics in the pathogenesis of numerous diseases, little is known about effective anti-lymphangiogenic agents compared to the abundance of anti-hemangiogenic agents that have entered clinical trials. Therefore, development of lymphangiogenesis inhibitors is of therapeutic value for treatment for lymphedema.

There is a need for methods and compositions that inhibit the activities of pro-lymphangiogenic factors and for methods that prevent or treat graft rejection, dry-eye disease tumor metastasis, lymphedema and other inflammatory conditions.

SUMMARY

An aspect of the invention provides a pharmaceutical composition for use in a subject to inhibit lymphangiogenesis which contains an inhibitor of a galectin-8 protein in an amount effective to inhibit or to modulate an activity of the galectin-8 protein or a portion of this protein sufficient to inhibit the lymphangiogenesis, and a pharmaceutically suitable carrier or a diluent. In various embodiments of the invention, the composition binds to the galectin-8 protein and modulates a VEGF-C/VEGF receptor-3 pathway in the subject. In other embodiments of the invention, the composition binds to the galectin-8 protein and modulates a podoplanin (PDPN) pathway in the subject. For example, the inhibitor binds to an N-carbohydrate recognition domain of the galectin-8 protein.

In various embodiments of the composition, the inhibitor is selected from at least one of: a polymer, a protein, a peptide, a carbohydrate, a low molecular weight compound, an oligonucleotide, a polynucleotide, and a genetic material such as DNA or RNA. For example, the inhibitor is selected from a dominant negative inhibitor or a saccharide inhibitor. In various embodiments of the composition, the saccharide inhibitor is selected from Thymine DNA glycosylase (TDG), 3'-sialyl lactose, and *Maackia amurensis* II (MAA II).

In various embodiments of the invention, the composition is formulated for topical administration. In alternative embodiments of the invention, the composition is formulated for administration by transscleral delivery and by a route selected from the group of passive diffusion, osmotic pump, iontophoresis, ocular implant, and controlled release device.

An aspect of the invention provides a method for treating or preventing lymphangiogenesis in a subject, the method including: administering a therapeutically effective amount of a pharmaceutical composition to the subject, such that the composition comprises an inhibitor of a galectin-8 protein or a portion thereof; and, measuring a decrease in a lymphangiogenesis marker in the subject. The method further includes analyzing an amount or an activity of at least one of the lymphangiogenesis marker selected from: podoplanin (PDPN), LYVE-1, PROX-1, desmoplakin, VEGF-C, VEGF-D receptor, and VEGFR-3.

The method in various embodiments further includes measuring interaction between at least two of the following: galectin-8 protein, VEGFR-3, and PDPN. The method in various embodiments further includes associating the lymphangiogenesis with a cancer, a corneal injury, a dry eye disease, an inflammation, a lymphedema, or a graft rejection. In various embodiments the administering further includes transscleral delivery by a route selected from the group of: passive diffusion, osmotic pump, iontophoresis, ocular implant or controlled release device. An embodiment of the administering is topical delivery.

The method in various embodiments further includes analyzing binding of the composition to the galectin-8 protein and modulating a VEGF-C/VEGF receptor-3 pathway and/or a PDPN pathway in the subject. The method in various embodiments prior to administering further includes selecting the inhibitor from a dominant negative inhibitor or a saccharide inhibitor. The saccharide inhibitor is for example selected from Thymine DNA glycosylase (TDG), 3'-sialyl lactose, and *Maackia amurensis* II (MAA II).

An aspect of the invention provides a method to identify an inhibitor of a galectin-8 protein, the method including: contacting a first sample of a galectin-8 protein with a test compound and measuring an amount of binding of the galectin-8 protein to a target protein, such that the target protein is at least one of VEGFR-3 or podoplanin (PDPN), under conditions for the galectin-8 protein to interact with the target protein; and comparing the amount of binding to that of a second sample of the galectin-8 protein not contacted by the test compound and otherwise identical, such that presence of the inhibitor is identified by a reduction of binding of galectin-8 in the first sample compared to the second sample. In various embodiments of the method the test compound is a sample which contains a plurality of compounds, for example from a library of compounds.

In various embodiments of the method to identify the inhibitor, the galectin-8 protein is in vitro. In other embodiments of the method the galectin-8 protein is in a cell. The method in various embodiments further includes contacting the inhibitor to mammalian cells and measuring a decrease in at least one of lymphangiogenesis markers.

In various embodiments of the method the plurality compounds in the sample which is identified as containing an inhibitory activity are chemically characterized and are tested for at least one property of binding to galectin-8, binding to galectin VEGFR-3, binding to PDPN, and decrease in in vivo induction of a lymphangiogenesis marker.

An aspect of the invention provides a pharmaceutical composition for use in a subject to treat lymphedema comprising a galectin-8 protein or a portion of this protein in a dose sufficient to promote lymphangiogenesis thereby treating lymphedema, and a pharmaceutically suitable carrier or a diluent.

In various embodiments of the composition, the galectin-8 protein is substantially identical to amino acid sequence of SEQ ID NO. 1 or a portion thereof, such that the amino acid sequence is at least about 70%, about 75%, about 80%, about 85%, about 90%, about 95%, or about 99% identical to SEQ ID NO: 1 or a portion thereof.

In other embodiments of the composition, the galectin-8 protein is substantially identical to amino acid sequence of SEQ ID NO. 2 or a portion thereof, such that the amino acid sequence is at least about 70%, about 75%, about 80%, about 85%, about 90%, about 95%, or about 99% identical to SEQ ID NO: 2 or a portion thereof. In various embodiments of the composition the galectin-8 protein comprises an N-carbohydrate recognition domain.

The sequence listing material in computer readable form ASCII text file (7 kilobytes) created 09/30/2016 entitled "34724-172 seqid ST25", containing sequence listings numbers 1-2, has been electronically filed herewith and is incorporated by reference herein in its entirety.

An aspect of the invention provides a method for treating or preventing lymphedema in a subject, the method including: formulating a composition comprising a galectin-8 protein or a portion of this protein sufficient to promote lymphangiogenesis; contacting the subject with the composition; and measuring a decrease in at least a symptom of lymphedema.

In various embodiments of the method, measuring further includes analyzing an amount of an activity of the at least one of symptom of lymphedema selected from swelling, thickness of skin, hardening of skin, feeling of fullness, aching, discomfort, and restricted range of motion. The method in various embodiments further includes analyzing binding of the galectin-8 protein to VEGFR-3 and/or podoplanin (PDPN).

An aspect of the invention provides a kit for treating or preventing lymphedema in a subject, the kit including: a pharmaceutical composition having a galectin-8 protein or a portion of this protein in a dose sufficient to promote lymphangiogenesis thereby treating lymphedema; instructions for use; and, a container.

An aspect of the invention provides a kit for treating or preventing lymphangiogenesis in a subject or cells from the subject, the kit including: a pharmaceutical composition having an inhibitor that inhibits a galectin-8 protein or portion thereof, such that the composition binds to the galectin protein and modulates a VEGF-C/VEGF receptor-3 pathway and/or a podoplanin (PDPN) pathway in the subject; instructions for use; and, a container.

BRIEF DESCRIPTION OF DRAWINGS

FIG. 1A-FIG. 1K are a set of photomicrographs showing that galectin-8 is markedly upregulated in inflamed human and mouse corneas. FIG. 1A-FIG. 1F shows human corneas with periodic acid-Schiff staining and galectin-8 immunostaining. Corneas and corneal buttons were removed at keratoplasty from patients with corneal graft failure, patients with bacterial keratitis, and patients with normal corneas. The corneal samples were embedded for paraffin sections and stained with periodic acid-Schiff and for galectin-8 immunoreactivity. The dark colored staining indicates immunostaining positive for galectin-8 activity. Compared to the normal corneas, markedly greater Gal-8 immunoreactivity was detected in the corneal stroma of patients with graft failure and bacterial keratitis. Four normal corneas, corneal buttons from six patients with graft failure, four patients with bacterial keratitis and two patients with *Acanthamoeba keratitis* were examined and the data obtained was observed to be reproducible.

FIG. 1G-FIG. 1K show immunohistochemistry for mouse corneas. For FIG. 1G-FIG. 1I mouse corneas were subjected to silver nitrate or thermal cautery, were allowed to partially heal in vivo, and were then analyzed for Gal-8 immunoreactivity in frozen sections. Nuclei were visualized by counterstaining with 4',6-diamidino-2-phenylindole (DAPI). Compared to the normal corneas, markedly greater Gal-8 immunoreactivity was detected in cauterized corneas. For FIG. 1J-FIG. 1K mouse corneas were subjected to alkaline burn, allowed to heal in vivo for two weeks and were then analyzed for galectin-8 (green) and type I collagen (red) immunoreactivity (FIG. 1J). Frozen sections of normal mouse corneas were also analyzed for galectin-8 (green), CD31 (cyan) and LYVE-1 (red) immunoreactivity. The color images were published April 2015 in The Journal of the Federation of American Societies for Experimental Biology which is entitled, "Pathological Lymphangiogenesis Is Regulated by Galectin-8-Dependent Crosstalk among VEGF-C, Podoplanin and Integrin Pathways", authored by Wei-Sheng Chen, Zhiyi Cao, Hakon Leffler, Ulf Nilsson, Lijun Xia and Nooijahan Panjwani (Chen et al. FASEB J April 2015 29:890.6), and which is incorporated by reference herein in its entirety. BV: blood vessel, CB: ciliary body, Epi: epithelium; LV: lymphatic vessel; SC: endothelium of Schlemm's canal; Str: stroma; TM: trabecular meshwork. Scale bar: 400 µm (FIG. 1A-FIG. 1F), 75 µm (FIG. 1G-FIG. 1I) and 10 µm (FIG. 1J-FIG. 1K).

FIG. 2C-FIG. 2D demonstrate that Gal-8 promotes lymphangiogenesis in an in vitro LEC sprouting assay. LEC spheroids were incubated with media containing various test agents. After 24 hours, the cumulative length of the sprouts was quantified. FIG. 2C shows that Gal-8, and not Gal-1, Gal-3 or Gal-7, promotes LEC sprouting. Representative photomicrographs for these results are shown in FIG. 2D.

FIG. 2E shows that Gal-8 promotion of lymphangiogenesis is dose-dependent and carbohydrate-dependent. FIG. 2F shows that Gal-8 mutant, Gal-8Q47A, which was engineered to have lost ability to bind to α2,3-sialylated glycans, did not promote LEC sprouting. FIG. 2G shows that 3'-SL, and not 6'-SL, inhibited Gal-8-induced LEC sprouting. FIG. 2H shows that Gal-8N does not promote LEC sprouting. FIG. 2I shows that Gal-8N inhibited Gal-8-induced sprouting. A value of 1.0 was assigned to the sprout length of Gal-8-treated cells. The values for other groups are expressed as a change in the sprout length with respect to Gal-8-treated LEC spheroids. Data are plotted as mean±SEM and analyzed using one-way ANOVA (FIG. 2Bi-FIG. 2E) and Student's t test (FIG. 2F and FIG. 2G). *$P<0.05$, ***$P<0.001$ vs control, ####$p<0.001$ vs Gal-8 (0.75 µM). TDG, thiodigalactoside; 3'-SL, 3'-sialylated lactose; 6'-SL, 6'-sialylated lactose; Gal-8N, N-terminal CRD. The data shown are representative of two or more independent examples.

FIG. 3A-FIG. 3F contains photographs, photomicrographs and bar graphs showing that Gal-8-induced LEC sprouting is dependent on activation of AKT and ERK pathways. FIG. 3A and FIG. 3B show that Gal-8 treatment activates AKT and ERK pathways. Primary LECs were treated with Gal-8 prior to lysis. Samples were separated by SDS-PAGE and analyzed by western blot with phospho-specific antibodies directed against 5473 of AKT and T202/Y204 of ERK. FIG. 3A shows western blot results for LECs incubated with Gal-8 (0.5 µM) for time periods ranging from 0 to 60 minutes prior to lysis. FIG. 3B shows western blot results for LECs incubated with concentrations of Gal-8 from 0.05 to 0.5 µM for 30 minutes prior to lysis. FIG. 3C and FIG. 3D show that inhibitors of PI3K and MEK inhibit Gal-8-induced LEC sprouting. LEC spheroids were stimulated with Gal-8 (0.75 µM) in the presence or absence of PI3K inhibitor (LY294002, 20 µM) or one of each of two different MEK inhibitors (U0126, 20 µM; PD0325901, 1 µM). Accumulated sprout lengths were quantified. A value of 1.0 was assigned to the sprout length of Gal-8 treated cells. The values for inhibitor treated groups are expressed as a change in the sprout length with respect to Gal-8 treated cells. Representative photomicrograph of sprouts is shown in FIG. 3D. FIG. 3E and FIG. 3F show data from positive controls with cells treated with VEGF-C (50 ng/ml). Data are plotted as mean±SEM and analyzed using one-way ANOVA. ***P<0.001 vs control. The results are representative of two independent examples.

FIG. 4A is a bar graph of quantified accumulated sprout lengths showing that Gal-8, and not Gal-1, Gal-3 or Gal-7, has a synergistic effect on VEGF-C-induced LEC sprouting. LEC spheroids were treated with VEGF-C (50 ng/ml) in the presence of Gal-1, Gal-3, Gal-7 or Gal-8, or absence of a galectin as a negative control, and the accumulated sprout lengths were quantified. FIG. 4B shows corresponding representative fluorescent images. FIG. 4C is a bar graph of fold changes in sprouting showing that a synergistic effect of Gal-8 on VEGF-C-induced LEC sprouting is dose-dependent. The LEC spheroids were treated with VEGF-C (50 ng/ml), in the presence or absence of varying concentrations of Gal-8. A value of 1.0 was assigned to the sprout length of VEGF-C treated cells. The values for other groups are expressed as a change in the sprout length with respect to VEGF-C-treated LEC spheroids. Gal-8 was observed to markedly enhance VEGF-C-induced lymphangiogenesis in vivo. Pellets containing either VEGF-C or Gal-8, were implanted in corneas of Prox1-EGFP reporter mice. One week after surgery, vessel area was calculated as described in examples herein and plotted in a bar graph shown in FIG. 4D. Representative fluorescent images are shown in FIG. 4E. Black asterisk indicates a control pellet; gray asterisk indicates VEGF-C pellet; and dark gray asterisk indicates Gal-8 pellet. Data are plotted as mean±SEM and analyzed using one-way ANOVA. ***P<0.001 vs control (FIG. 4A-FIG. 4B), VEGF-C (B). #P<0.05 vs VEGF-C (FIG. 4A-FIG. 4B); ###P<0.001 vs VEGF-C (FIG. 4A-FIG. 4B). The results are representative of two independent examples.

FIG. 5A is a photograph of a western blot showing that VEGFR-3 is a Gal-8 binding protein. LEC lysates were incubated with Gal-8-conjugated agarose beads in the presence or absence of 0.1 M of lactose (an inhibiting sugar) or sucrose (a non-inhibiting sugar) or absence (negative control) of a sugar. Bound proteins were examined with total cell lysates (input) by western blot using anti-VEGFR-3 antibody. LEC lysates incubated with unconjugated beads served as a negative control. To determine whether VEGFR-3 contains α2,3-sialylated glycans, binding of VEGFR-3 to a plant lectin, MAA II, which binds selectively to α2,3-linked sialic acids was examined. FIG. 5B-FIG. 5G shows that VEGF-C-induced LEC sprouting was observed to be inhibited by inhibitors of Gal-8. LEC spheroids were stimulated with VEGF-C (50 ng/ml) in the presence or absence of varying concentrations of TDG (FIG. 5B), 3'-SL (FIG. 5D) or Gal-8N (FIG. 5F). After 24 hr, accumulated sprout lengths were quantified. A value of 1.0 was assigned to the sprout length of VEGF-C treated LEC spheroids. The values observed for inhibitor treated groups are expressed as a change in the sprout length with respect to VEGF-C treated LEC spheroids. Representative images of sprouts from corresponding examples are shown FIG. 5C, FIG. 5E, and FIG. 5G respectively. Data were plotted as mean±SEM and analyzed using Student's t test. *P<0.05, P<0.01, *P<0.001 vs VEGF-C. MAA II, *Maakia amurensis* agglutinin II, 3'-SL, 3'-sialyllactose. The results are representative of two or more independent examples.

FIG. 6A is a bar graph of accumulated sprout length showing that VEGFR-3 knockdown using siRNA for VEGFR-3 did not decrease Gal-8-induced lymphangiogenesis compared to control siRNA. LEC spheroids prepared using primary LECs transfected with control or VEGFR-3 siRNA were treated with Gal-8 (0.75 µM) or VEGF-C (50 ng/ml). After 24 hr, accumulated sprout lengths were quantified. Representative images are shown in FIG. 6B. FIG. 6C-FIG. 6E are bar graphs showing that VEGFR-3-Fc only modestly reduced Gal-8-induced lymphangiogenesis. LEC spheroids were stimulated with Gal-8 (0.75 µM) in the presence 10 µM of VEGFR-3-Fc, VEGFR-2-Fc, Avastin or control IgG (FIG. 6E). Accumulated sprout lengths were quantified. Treatment with VEGF-C (50 ng/ml) and VEGF-A (50 ng/ml) served as positive controls (FIGS. 6C and D). It was observed from the data in FIG. 6F-FIG. 6G that VEGFR-3 knockdown moderately reduced Gal-8-induced activation of AKT and ERK. Primary LECs were transfected with control or VEGFR-3 siRNA; the cells were serum-starved and treated with Gal-8 (0.5 µM) or VEGF-C (50 ng/ml, positive control) for 30 min. Electrophoresis blots of cell lysates were probed with indicated antibodies (FIG. 6F). Data were plotted as mean±SEM and analyzed using Student's t test (FIG. 6A, FIG. 6F and FIG. 6G) and one-way ANOVA (FIG. 6C-FIG. 6E) as shown in FIG. 6G. ***P<0.001 vs Gal-8 (0.75 µM), VEGF-C, or VEGF-A (FIG. 6C-FIG. 6E). For panel Cii, N=3 in each group. ###P<0.001 vs Gal-8/VEGF-C/VEGF-A+Ctrl IgG (FIG. 6C-FIG. 6E). The results are representative of two or more independent examples.

FIG. 7A is a photograph of western blot showing that PDPN binds to Gal-8, and does not bind to Gal-1, Gal-3 or Gal-7. LEC lysates were incubated with galectins and MAA II conjugated to agarose beads. Bound proteins were examined and were compared to total cell lysates (input) by western blot using anti-PDPN. FIG. 7B is a photograph of a western blot of PDPN knockdown cells. Primary LECs were transfected with control (mock) or two siRNA that targeted different regions of PDPN. Knockdown efficiency was assessed by western blot using anti-PDPN and anti-β-actin antibodies. FIG. 7C-FIG. 7D show that PDPN knockdown inhibits each of VEGF-C- and Gal-8-induced LEC sprouting. Spheroids prepared using primary LECs transfected with control or pooled PDPN siRNA were treated with Gal-8 (0.75 µM) or VEGF-C (50 ng/ml). After 24 hr, accumulated sprout lengths were quantified and plotted in a bar graph shown in FIG. 7C. Representative images of the sprouts are shown in FIG. 7D. FIG. 7E-FIG. 7F show that PDPN knockdown significantly decreased both Gal-8-induced and VEGF-C-induced activation of AKT but not of ERK. Primary LECs were transfected with control or PDPN siRNA. The cells were serum-starved and treated with Gal-8 (0.5 µM) or VEGF-C (50 ng/ml, positive control) for 30 min. Electrophoresis blots of cell lysates were probed with indicated antibodies as shown in FIG. 7E. Quantification of fluorescence intensity of western blots (N=5) is shown in bar graph of FIG. 7F. Data are plotted as mean±SEM and analyzed using Student's t test (FIG. 7C and FIG. 7F). *$P<0.05$, ***$P<0.001$ vs corresponding control. The results are representative of two or more independent examples.

FIG. 8A-FIG. 8D show that VEGF-C-induced hemangiogenesis and lymphangiogenesis. FIG. 8E-FIG. 8H show that Gal-8-induced hemangiogenesis and lymphangiogenesis. VEGF-C pellets (160 ng) (FIG. 8A-FIG. 8D) and Gal-8 pellets (160 ng) (FIG. 8E-FIG. 8H) were implanted into wild type (WT) (FIG. 8C and FIG. 8E) and PDPN inducible KO (FIG. 8D and FIG. 8H) mice. Seven days post implantation, the corneal flat mounts were stained with anti-CD31 and anti-LYVE-1 to visualize blood and lymphatic vessels, respectively. Blood vessel (FIG. 8A and FIG. 8E) and lymphatic vessel (FIG. 8B and FIG. 8F) areas were quantified. Representative fluorescence images from each group are shown in FIG. 8C, Fig. D, Fig. G and Fig. H respectively. Data are plotted as mean±SEM and analyzed using Student's t test. *$P<0.05$, **$P<0.01$ vs WT.

FIG. 9A-FIG. 9D shows that in control LECs, VEGFR-3 and PDPN were distributed at the cell junctions and cytosol and endogenous Gal-8 was distributed mainly in the cytosol. FIG. 9F-FIG. 9I shows that exogenous Gal-8 caused sequestration of each of VEGFR-3 and PDPN. PDPN and VEGFR-3 distribution was reorganized and colocalized at cell borders as a result of Gal-8 treatment. The arrows in FIG. 9F indicate colocolization of VEGFR-3, PDPN and Gal-8. FIG. 9E and FIG. 9J shows that Gal-8 increased cell-surface residency of PDPN and VEGFR-3. Primary LECs were treated with VEGF-C (50 ng/ml) or Gal-8 (0.2 µM) for 10 and 30 min. Cells were fixed and stained with anti-PDPN and VEGFR-3 antibodies. Cell surface expression of PDPN (FIG. 9E) and VEGFR-3 (FIG. 9J) was analyzed with flow cytometry and quantified with FlowJo. Data are plotted as Mean±SEM from three independent examples and analyzed with Student's t test. *$P<0.05$, ***$P<0.001$ vs VEGF-C treatment. MFI: mean fluorescence intensity. Scale bar: 10 µm.

FIG. 10A, FIG. 10B, FIG. 10E, FIG. 10G and FIG. 10I), or with Gal-8N (15 µg, a dominant negative inhibitor of Gal-8; FIG. 10C, FIG. 10D, FIG. 10F, FIG. 10H and FIG. 10J) by local subconjunctival injections on days 0, 2, 4 and 6 post-surgery. At the end of the treatment period, lymphatic vessel areas were quantified as shown in FIG. 10A, FIG. 10C, FIG. 10E and FIG. 10F. Representative images are shown in FIG. 10A, FIG. 10D, FIG. 10G-FIG. 10J. Data are plotted as mean±SEM and analyzed using Student's t test. The results are representative of two independent examples.

FIG. 14A-FIG. 14C show that VEGF-C-induced hemangiogenesis and lymphangiogenesis are reduced in galectin-8 knockout (KO) mice. VEGF-C pellets (160 ng) were implanted into wild type (WT, N=10) (FIG. 14B) and galectin-8 KO (N=10) (FIG. 14C) mice. Seven days post implantation, the corneal flat mounts were stained with anti-CD31 and anti-LYVE-1 to visualize blood and lymphatic vessels, respectively. FIG. 14D-FIG. 14F show that suture-induced inflammatory hemangiogenesis and lymphangiogenesis are reduced in galectin-8 knockout (KO) mice. Sutures were placed 2 mm above the limbal vessel in the corneas of WT (N=5) (FIG. 14E) and galectin-8 KO (N=10) (FIG. 14F) mice. Seven days post surgery, the corneal flat mounts were stained with anti-CD31 and anti-LYVE-1 to visualize blood and lymphatic vessels, respectively. Blood vessel and lymphatic vessel areas were quantified (FIG. 14A, and FIG. 14D). Representative fluorescence images from each group are shown in FIG. 14B, FIG. 14C, FIG. 14E and FIG. 14F. Data are plotted as mean±SEM and analyzed using Student's t test. *P<0.05 vs WT.

FIG. 15A bar graphs show that α1β1 and α5β1 inhibition reduces both VEGF-C- and galectin-8-induced LEC sprouting. LEC spheroids were stimulated with VEGF-C (50 ng/ml) (FIG. 15A, left panel) or galectin-8 (0.75 µM) (FIG. 15A, right panel) in the presence or absence as indicated of control IgG, functional blocking antibodies (20 µg/ml) and peptides. The blocking peptides used in the assay were 4 µM of Obtustatin (specific for integrin α1β1) and 20 µM of BIO1211 (specific for integrin α4β1). The accumulated sprout lengths were quantified after 24 hours. A value of 1.0 was assigned to the sprout length of VEGF-C or galectin-8 treated LEC spheroids. The values for the inhibitor treated groups are expressed as a change in the sprout length with respect to VEGF-C or galectin-8 treated LEC spheroids. FIG. 15B-FIG. 15C are photomicrographs showing that galectin-8 clusters VEGFR-3 and PDPN on cell surface. LECs were treated with or without galectin-8 for 15 min, fixed without permeabilization, stained with antibodies to anti-VEGFR-3 (green), PDPN (blue) and galectin-8 (red), and examined by confocal microscopy. Merged images are shown in the FIG. 15B and FIG. 15C right panels. In control LECs, no colocalization of VEGFR-3, galectin-8 and PDPN was observed (FIG. 15B). FIG. 15C shows that exogenous galectin-8 caused VEGFR-3 and PDPN to sequester. PDPN and VEGFR-3 distribution were observed to have been reorganized and colocalized (white spots in the merged image) at cell borders after galectin-8 treatment. Scale bar: 7.5 µM. FIG. 15D contains photographs of western blots showing that Integrins α5 and β1 interact with PDPN in a galectin-8-dependent manner. LECs were incubated with or without galectin-8 (0.5 µM) for 15 min at 37° C. Total cell lysates were immunoprecipitated as indicated with control antibody and anti-PDPN antibody, and were processed for western blotting using antibodies indicated. Fold changes were normalized to PDPN. Data are plotted as mean SEM and analyzed using one-way ANOVA (FIG. 15A). ***P<0.001 vs VEGF-C or Gal-8 (FIG. 15A); ###P<0.001 vs VEGF-C or Gal-8+ control IgG (FIG. 15A).

FIG. 16A-FIG. 16B are 3D schematic protein structure drawings for a model of galectin-8-mediated lymphangiogenesis. FIG. 16A envisions a galectin-8-mediated lymphangiogenesis model in which galectin-8 cross-links and clusters integrins α1β1/α5β1 and PDPN on the cell surface. The clustering activates lymphangiogenic signaling pathways that modulate events such as endothelial cell migration and sprouting without the involvement of VEGFR-3. This model is supported by examples herein showing that: VEGFR-3 is dispensable in galectin-8-mediated lymphangiogenesis; galectin-8-mediated lymphangiogenesis is dependent on PDPN, and integrins α1β1/α5β1; and galectin-8 treatment increases the interaction of PDPN and integrin β1. FIG. 16B envisions a galectin-8-mediated lymphangiogenesis model in the presence of VEGFR-3 in which PDPN-galectin-8-integrin interactions substantially increase the magnitude of lymphangiogenic pathway by potentiating the VEGF-C/VEGFR-3 signaling. This model is supported by data obtained in the examples herein which show that galectin-8 stimulates VEGF-C-induced lymphangiogenesis in vitro and in vivo, galectin-8 inhibitors attenuate VEGF-C-induced lymphangiogenesis in vitro and in vivo, and that Gal-8-induced lymphangiogenesis is reduced by α1β1 and α5β1 inhibitors. In FIG. 16A-FIG. 16B only extracellular domains of glycoproteins are shown.

FIG. 18A is a dose-response curve of galectin-8-mediated LEC sprouting. Open circles indicate actual data points. LEC sprouting activity of galectin-8 at 0.75 µM is set at 100%. EC50 of galectin-8-mediated LEC sprouting was observed to be 0.52 µM and Hill's coefficient (nH) is 3.7. FIG. 18B shows theoretical curves of different nH (nH=1 to 5), broken lines were simulated and the solid line indicates galectin-8-mediated LEC sprouting based on experimental results. The results are plotted in Origin 9.1 (FIG. 18A) and R programming language (FIG. 18B).

FIG. 19A-FIG. 19C show inhibitory effect of concentration of 3'-SL on galectin-8-mediated LEC sprouting at 0.75 µM. FIG. 19D-FIG. 19F shows inhibitory effect of Gal-8N on galectin-8-mediated LEC sprouting at 0.75 µM. Open circles indicate the actual data points. IC50 of the inhibitory effect of 3'-SL (FIG. 19A) and Gal-8N (FIG. 19D) are 1.25 mM and 1.98 µM respectively. nH of 3'-SL and Gal-8N are 3.38 and 3.85 respectively. Ki of 3'-SL and Gal-8N are 1.67 mM and 0.86 µM respectively. (Ki=IC50/(1+[A]/EC50)). Theoretical curves of different nH (nH=1 to 5) red broken lines, were simulated and the blue lines indicate the inhibitory curves of 3'-SL and Gal-8N respectively based on the observed results (FIG. 19B, FIG. 19E respectively). Inhibitory effect of 3'-SL (FIG. 19C) and Gal-8N (FIG. 19F) on galectin-8-mediated LEC sprouting at varying concentrations were also simulated. The results are plotted in Origin 9.1 (FIG. 19A, FIG. 19D), R programming language (FIG. 19B, FIG. 19E) and MATLAB2013 (FIG. 19C, FIG. 19F).

FIG. 21A shows that none of the four galectins assayed bind VEGF-C. VEGFR-1 indirectly promotes lymphangiogenesis by recruiting macrophages (Murakami, M. et al., 2008, *Arterioschl. Thromb. Vasc. Biol.* 28 (4): 658-664), accordingly examples herein were conducted to determine whether VEGFR-1 binds to one or more galectins. VEGFR-1 was observed to not interact with any of these four lectins. Primary LECs were incubated with agarose beads (control), and galectin-conjugated agarose beads at 4° C. overnight. Unbound proteins were removed and the bound proteins were eluted with 20 μL of 2x Laemmli sample buffer and analyzed and compared to control input by western blotting. FIG. 21B shows that VEGFR-3 is a galectin-8 binding protein. LEC lysates were incubated with galectin-8-conjugated agarose beads in the presence or absence of 100 mM of lactose (an inhibiting sugar) or sucrose (a non-inhibiting sugar). Bound proteins were observed with total cell lysates (input) by western blot using anti-VEGFR-3 antibody. LEC lysates incubated with unconjugated beads served as a negative control. To determine whether VEGFR-3 contains α2,3-sialylated glycans, ligands of galectin-8, binding of VEGFR-3 to a plant lectin, MAA II, which binds selectively to α2,3-linked sialic acids were assayed. MAA II, *Maakia amurensis* agglutinin II.

In FIG. 22B exogenous galectin-8 was observed to sequester VEGFR-3 and PDPN. PDPN and VEGFR-3 distribution was observed to reorganize and colocalize (white spots in the merged image) at cell borders after galectin-8 treatment. Scale bar: 7.5 μm.

FIG. 23A, FIG. 23B, FIG. 23D and FIG. 23E show results from LEC spheroids that were prepared using primary LECs transfected with control, VEGFR-3 siRNA (FIG. 23A, FIG. 23B) or Nrp2 siRNA (FIG. 23D, FIG. 23E) and were treated with galectin-8 (0.75 μM) or VEGF-C (50 ng/ml). After 24 hours, accumulated sprout lengths were quantified (FIG. 23A, FIG. 23D). Representative images are shown in FIG. 23B and FIG. 23E. Data are plotted as mean±SEM and analyzed using Student's t test. FIG. 23C and FIG. 23F show assessment of VEGFR-3 and Nrp2 knockdown efficiency. Cell lysates from control, VEGFR-3 knockdown, or Nrp2 knockdown cells were subjected to SDS-PAGE followed by immunoblotting with anti-VEGFR-3, anti-Nrp2 or anti-GAPDH as indicated. Three independent samples were used in the control and VEGFR-3 or Nrp2 knockdown.

In FIG. 25A, LECs were incubated with or without anti-PDPN Ab or isotype control Ab (10 μg/ml). In FIG. 25B, LECs were transfected with control siRNA or PDPN siRNA. The cells were seeded into the upper chamber of Transwell inserts. The lower-side of the insert membrane was coated with fibronectin (10 μg/ml) or galectin-8 (0.5 μM). After incubation for 2 hours at 37° C., LECs were assayed by counting the number that had migrated to the lower side of the membrane (FIG. 25B). Results are expressed as % change in which the control is set as 100%. Data are plotted as mean±SEM and analyzed using one-way ANOVA (FIG. 25A) and Student's t test (FIG. 25B). *P<0.05, P<0.01 vs control IgG (FIG. 25A); *P<0.001 vs control siRNA (FIG. 25B); ##P<0.01 vs control IgG (FIG. 25A).

DETAILED DESCRIPTION

Figure 2A:
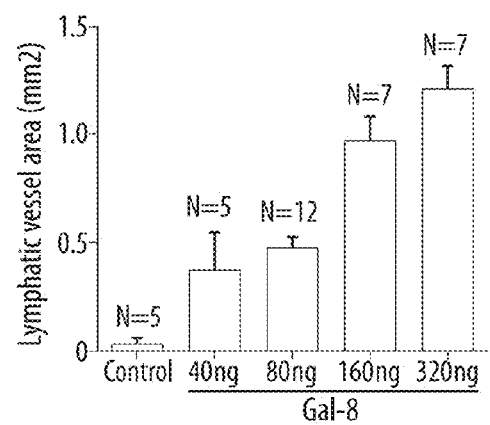
FIG. 2A-FIG. 2I are photomicrographs and bar and line graphs showing that Gal-8 promotes lymphangiogenesis in vivo and in vitro. Sustained-release polymer pellets containing various doses of Gal-8 were implanted in the corneas of Prox1-EGFP reporter mice. One week after surgery, the vessel area was calculated and shows that Gal-8 promotes lymphangiogenesis in vivo. Data are expressed as mean±SEM. A representative fluorescence photomicrograph of a cornea implanted with Gal-8 pellet (160 ng/pellet) is shown in FIG. 2B. White asterisk indicates the pellet. Bar=400 µM.

Lymphangiogenesis plays a vital role in diverse pathological conditions. The role of galectins, a family of carbohydrate-binding proteins, in lymphangiogenesis is still elusive. The examples herein show that galectin-8 is a potent lymphangiogenic factor. Galectin-8 was markedly upregulated in inflamed human and mouse corneas, and inhibitors of galectin-8 reduced suture-induced lymphangiogenesis in mouse corneas. In corneal micropocket assays and 3D sprouting assays, galectin-8 promoted lymphangiogenesis in a carbohydrate-dependent manner. In contrast, Galectins-1, -3, and -7 are not lymphangiogenic. Galectin-8 was identified as a key mediator of VEGF-C/VEGFR-3 signaling. Galectin-8 inhibitors reduced VEGF-C-induced lymphangiogenesis. Conversely, exogenous galectin-8 markedly enhanced VEGF-C-induced lymphangiogenesis in a carbohydrate-dependent manner. Galectin-8 binds also to glycans of VEGFR-3 and another lymphangiogenic molecule, podoplanin, and VEGF-C and galectin-8-mediated lymphangiogenesis is reduced in podoplanin knockout mice and podoplanin knockdown lymphatic endothelial cells (LECs). Importantly, galectin-8 added to LECs caused segregation of VEGFR-3 and podoplanin on plasma membranes and activated AKT and ERK pathways. Collectively, these data indicate that galectinal-8 binds to specific glycan ligands on cell-surface VEGFR-3 and podoplanin and segregates them into discrete signaling complexes to activate lymphangiogenesis. In summary, lymphangiogenesis is regulated by galectin-8-dependent crosstalk between VEGFR-3 and podoplanin.

Galectins

Lectins are proteins that are defined by their ability to bind carbohydrates specifically and to agglutinate cells (see, for example, Sharon, *Trends Biochem. Sci.* 18: 221, 1993). Lectins have been shown to be involved in a wide variety of cellular functions including cell-cell and cell-matrix interactions. Lectins are widespread among plants, invertebrates and mammals. Animal lectins have been grouped into four distinct families: 1) C-type lectins; 2) P-type lectins; 3) galectins (formerly termed S-type lectins); and 4) pentraxins (see, for example, Barondes et al., *J. Biol. Chem.* 269:20807, 1994).

Mammalian galectins that have been analyzed in detail recognize β-lactose and related β-galactosides. While all mammalian galectins share similar affinity for small β-galactosides, they show significant differences in binding specificity for more complex glycoconjugates (Henrick et al., *Glycobiology* 8:45, 1998; Sato et al., *J. Biol. Chem.* 267:6983, 1992; and Seetharaman et al., *J. Biol. Chem.* 273:13047, 1998). In addition to binding β-galactoside sugars, galectins possess hemagglutination activity. Laminin, a naturally occurring glycoprotein containing numerous polylactosamine chains, has been shown to be a natural ligand for certain galectins. Laminin is a component of the basal laminae, the extracellular matrix which underlies all epithelia and surrounds individual muscle, fat and Schwann cells. Interactions between cells and the basal laminae are known to influence the migration and/or differentiation of various cell types during mammalian development. Galectins do not contain traditional sequences that specify membrane translocation, but are both secreted and located intracellularly. In addition to their affinity for β-galactoside sugars, members of the galectin family share significant sequence similarity in the carbohydrate recognition domain (CRD; also referred to as the carbohydrate-binding domain), the relevant amino acid residues of which have been determined by X-ray crystallography (Lobsanov et al., *J. Biol. Chem.* 267:27034, 1993 and Seetharaman et al., supra). Galectins have been implicated in a wide variety of biological functions including cell adhesion (Cooper et al., *J. Cell Biol.* 115:1437, 1991), growth regulation (Wells et al., *Cell* 64:91, 1991), cell migration (Hughes, *Curr. Opin. Struct. Biol.* 2:687, 1992), neoplastic transformation (Raz et al., *Int. J. Cancer* 46:871, 1990) and immune responses (Offner et al., *J. Neuroimmunol.* 28:177, 1990). There are presently 12 characterized eukaryotic members of the galectin family.

Galectin-8

Galectin-8 is a widely expressed protein, present for example, in liver, heart, muscle, kidney, spleen, hind-limb and brain, and the sequence of human and rat galectin-8 genes and proteins are available (see for example Hadari, et al., Trends in Glycosci and Glycotechnol. 9: 103-112, 1997). The highly hydrophilic character and function for binding to Galβ1-4GlcNAC disaccharides found in the O-linked oligosaccharides of mucins make this protein an ideal agent for treating dry eye syndrome.

Two forms of amino acid sequence for human galectin-8 are known, a 316 amino acid form (Accession number 000214, created 1 Nov. 1997) and a 359 amino acid form (Accession number Q8TEV1, created 1 Jun. 2002). These sequences, while similar or identical for significant lengths, are not overall mere length variants, having portions of difference. The 316 form amino acid sequence, using the one letter amino acid code, is shown below (SEQ ID NO: 1):

```
MLSLNNLQNI IYNPVIPYVG TIPDQLDPGT LIVICGHVPS DADRFQVDLQ NGSSVKPRAD   60

VAFHFNPRFK RAGCIVCNTL INEKWGREEI TYDTPFKREK SFEIVIMVLK DKFQVAVNGK  120

HTLLYGHRIG PEKIDTLGIY GKVNIHSIGF SFSSDLQSTQ ASSLELTEIS RENVPKSGTP  180

QLSLPFAARL NTPMGPGRTV VVKGEVNANA KSFNVDLLAG KSKDIALHLN PRLNIKAFVR  240

NSFLQESWGE EERNITSFPF SPGMYFEMII YCDVREFKVA VNGVHSLEYK HRFKELSSID  300

TLEINGDIHL LEVRSW                                                 316
```

The amino acid sequence of the longer form is shown below (SEQ ID NO: 2):

```
MMLSLNNLQN IIYSPVIPYV GTIPDQLDPG TLIVICGHVP SDADRFQVDL QNGSSVKPRA   60

DVAFHFNPRF KRAGCIVCNT LINEKWGREE ITYDTPFKRE KSFEIVIMVL KDKFQVAVNG  120

KHTLLYGHRI GPEKIDTLGI YGKVNIHSIG FSFSSDLQST QASSLELTEI SRENVPKSGT  180

PQLPSNRGGD ISKIAPRTVY TKSKDSTVNH TLTCTKIPPT NYVSKILPFA ARLNTPMGPG  240

GTVVVKGEVN ANAKSFNVDL LAGKSKHIAL HLNPRLNIKA FVRNSFLQES WGEEERNITS  300

FPFSPGMYFE MIIYCDVREF KVAVNGVHSL EYKHRFKELS SIDTLEINGD IHLLEVRSW   359
```

As defined herein, a "galectin-8 protein" may include a galectin-8 "N-terminal domain", a galectin-8 "proline, glycine, and tyrosine-rich domain", and/or a galectin-8 "galactoside-binding domain". These domains are further defined as follows.

As used herein, a galectin-8 "N-terminal domain" includes an amino acid sequence of about 10-20 amino acids, preferably about 14 amino acids that shares at least about 60%, 70%, 80%, 90%, 95%, 99%, or 100% identity with amino acids 1 to 14 of SEQ ID NOs:1 or 2. The N-terminal domain can include an N-glycosylation site (PROSITE No. PS00001) and/or a casein kinase II phosphorylation site (PROSITE No. PS00006). The PROSITE N-glycosylation site has the consensus sequence: N-{P}-[ST]-{P} and the PROSITE casein kinase II phosphorylation site has the consensus sequence: [ST]-X(2)-[DE]. In the above consensus sequences, and other motifs or signature sequences.

As used herein, a galectin-8 "proline, glycine, and tyrosine-rich domain" includes an amino acid sequence of about 60 to 140 amino acids, more preferably about 80 to 120 amino acids, or about 90 to 110 amino acids that shares at least about 60%, 70%, 80%, 90%, 95%, 99%, or 100% identity with amino acids 15 to 116 of each of SEQ ID NOs: 1 and 2. The proline, glycine, and tyrosine-rich domain can also include one, two, three, four, five, six, seven, or eight N-myristoylation sites (PROSITE No. PS00008) which have the consensus sequence: G-{EDRKHPFYW}-X(2)-[STAGCN]-{P}. In certain embodiments, the proline, glycine, and tyrosine-rich domain includes the following amino acids and regions of SEQ ID NO: 2: G20, P23, P28, G29, G36, P39, and other such residues as are obvious to one of skill in the art. These amino acids and regions are conserved across several mammalian species of galectin-8 and may play a catalytic and/or structural role. In certain embodiments, the proline, glycine, and tyrosine-rich domain includes the following amino acids and regions of SEQ ID NO:2: G21, P24, P29, G30, G37, P40, and other such residues as are obvious to one of skill in the art.

To calculate the bit score for the alignment of a particular sequence to the consensus sequence, the sequence of interest can be searched against the PFAM database of HMMs (e.g., the PFAM database, release 2.1) using the default parameters available at www.sanger.ac.uk/Software/Pfam. A description of the PFAM database can be found in Sonnhammer et al., supra and a detailed description of HMMs can be found, for example, in Gribskov et al., Meth. Enzymol. 183:146, 1990 and Stultz et al., Protein Sci. 2:305, 1993.

A galectin-8 galactoside-binding domain can include one, preferably two, protein kinase C phosphorylation sites (PROSITE No. PS00005); a casein kinase II phosphorylation site (PROSITE No. PS00006); and/or a galaptin signature sequence (PROSITE No. PS00309). The protein kinase C phosphorylation site has the following consensus sequence: [ST]-X-[RK]. The galaptin signature sequence has the following consensus sequence: W-[GEK]-X-[EQ]-X-[KRE]-X(3,6)-[PCTF]-[LIVMF]-[NQEGSKV]-X-[GH]-X(3)-[DENKHS]-[LIVMFC]. In certain embodiments, the galectin-8 galactoside-binding domain includes the following amino acids and regions of SEQ ID NO: 1: L123-L124, G126, P131, R128, L140-I146, and other sites similar to those as demonstrated above. These amino acids and regions are conserved across several mammalian species of galectin-8 and may play a catalytic and/or structural role.

Certain galectin-8 proteins of the present invention include the amino acid sequence of human galectin-8 as represented by SEQ ID NOs: 1 and 2. Other galectin-8 proteins of the present invention include an amino acid sequence that is substantially identical to the amino acid sequence of SEQ ID NOs: 1 or 2. The term "substantially identical" is used herein to refer to a first amino acid that contains a sufficient or minimum number of amino acid residues that are identical to aligned amino acid residues in a second amino acid sequence such that the first and second amino acid sequences can have a common structural domain and/or common functional activity. For example, amino acid sequences that contain a common structural domain having at least about 60%, or 65% identity, preferably at least 75% identity, more preferably at least 85%, 90%, 91%, 92%, 93%, 94%, 95%, 96%, 97%, 98%, or 99% identity to SEQ ID NOs:1 or 2 are termed substantially identical to the amino acid sequence of SEQ ID NOs:1 or 2. In particular, proteins which contain accidentally or deliberately induced alterations, such as deletions, additions, substitutions or modifications of certain amino acid residues of SEQ ID NOs: 1 or 2 may fall within the definition of galectin-8 proteins provided herein. It will also be appreciated that as defined herein, galectin-8 proteins may include regions represented by the amino acid sequence of galectin-8 taken from other mammalian species including but not limited to bovine, canine, feline, caprine, ovine, porcine, murine, and equine species.

The examples herein describe multiple approaches involving use of galectin mutants lacking carbohydrate-binding activity, specific sugar inhibitors of galectins, and siRNA knockdown of key players of lymphangiogenesis, to establish a critical role of carbohydrate-mediated VEGFR-3/Gal-8/PDPN interactions in the process of lymphangiogenesis. The examples herein demonstrate that Gal-8 expression is markedly upregulated in inflamed human and mouse corneas, that Gal-8 is a potent lymphangiogenic factor and a key mediator of VEGF-C/VEGFR-3 signaling, and that lymphangiogenesis is regulated by a Gal-8-dependent cross-talk between VEGFR-3 and PDPN. More importantly, examples herein show that inhibitors of Gal-8 decrease lymphatic vessel formation in inflamed mouse corneas in vivo.

Data obtained from immunohistochemical examples indicated that Gal-8 is strongly expressed in inflamed human and mouse corneas and that Gal-8 expression in normal corneas is relatively low. The in vivo corneal micropocket assays described herein indicated that Gal-8 promoted lymphangiogenesis in a dose-dependent manner. The in vitro three-dimensional sprouting assays indicated that Gal-8 alone promoted LEC sprouting compared to Gal-1, Gal-3 or Gal-7. The stimulatory effect of Gal-8 on LEC sprouting was demonstrated to be dose-dependent and is almost completely abrogated by TDG, a pan inhibitor of galectins (inhibitor of many galectins). The striking finding that several other members of the galectin family including Gal-1 and Gal-3, which are known to promote hemangiogenesis, did not promote LEC sprouting in vitro indicates that the Gal-8-mediated process of lymphangiogenesis involves the affinity of N-CRD of Gal-8 for 3'-sialylated galactosides that is unique among animal galectins (Carlsson, S., et al. 2007. Glycobiology 17:663-676; Ideo, H., et al. 2011. J Biol Chem 286:11346-11355; Ideo, H., et al. 2003. Glycobiology 13:713-723). The specific inhibition of the N-CRD of Gal-8 with 3'-SL reduced lymphangiogenesis in vitro. A Gal-8 mutant, Gal-8Q47A, which has lost its ability to bind to α2,3-sialylated glycans, did not promote lymphangiogenesis in vitro. Together, these data conclusively establish that Gal-8 promotes lymphangiogenesis in a carbohydrate-dependent manner and that N-CRD of Gal-8 is directly involved in the stimulatory effect of Gal-8 on LEC sprouting.

Di/multivalent properties of galectins allow the galectins to cross-link many cell surface and extracellular matrix glycoproteins, such as integrins and growth factor receptors, to regulate signal transduction pathways (Partridge, E. A., et al. 2004. Science 306:120-124; Saravanan, C., et al. 2009. J Cell Sci 122:3684-3693; Seguin, L., et al. 2014. Nat Cell Biol; Stillman, B. N., et al. 2006. J Immunol 176:778-789). Isolated CRDs of Gal-8 retain the carbohydrate binding activity and manifest impaired biological activity (Carlsson, S., et al. 2007. Glycobiology 17:906-912; Levy, Y., et al. 2006. Glycobiology 16:463-476), indicating that lectin requires cooperative interactions between the two CRDs. In examples herein, truncated Gal-8 with only the N-CRD (Gal-8N) not only failed to induce lymphangiogenesis, but also effectively inhibited the lymphangiogenesis induced by full-length Gal-8. Therefore, Gal-8N, which contains the entire N-CRD and retains the ability to bind to 3'-sialylated glycans effectively, competes with full-length Gal-8 and thereby acts as a dominant negative inhibitor of Gal-8. Similarly, truncated Gal-3 containing a full CRD but lacking the N-terminal oligomerizing domain also serves as a dominant negative inhibitor of Gal-3 (John, C. M., et al. 2003. *Clin Cancer Res* 9:2374-2383; Markowska, A. I., et al. 2010. *J Exp Med* 207:1981-1993). The inhibitory effect of Gal-8N on VEGF-C-induced LEC sprouting is bell-shaped, which is similar to several other anti-angiogenic molecules, such as RGD-mimetic integrin inhibitors, plasminogen activator-1, bortezomib, TGF-β1, etc (Reynolds, A. R. 2009. *Dose Response* 8:253-284).

The examples herein show data indicating that Gal-8N (a dominant negative inhibitor of Gal-8) and saccharide inhibitors of Gal-8 (TDG and 3'-SL) ameliorated VEGF-C-induced lymphangiogenesis activity. In addition, the examples also describe in vivo corneal micropocket assays in which saccharide inhibitors of Gal-8 significantly inhibited VEGF-C-induced lymphangiogenesis. Moreover, Gal-8 was observed to have markedly enhanced VEGF-C-induced lymphangiogenesis in vitro and in vivo. In an effort to characterize the molecular mechanism by which Gal-8 modulates VEGF-C-mediated lymphangiogenesis, the function of Gal-8 with respect to the glycosylation pattern of VEGFR-3 was investigated. Affinity precipitation assay was used with Gal-8-conjugated agarose beads, and data obtained show that VEGFR-3 was identified as a Gal-8-binding protein in LECs. Affinity precipitation assay conducted using a plant lectin, MAA II, which binds selectively to α2,3-linked sialic acids, indicated that VEGFR-3 contains 3'-sialylated glycans, the high affinity ligands of Gal-8. More importantly, confocal microscopy indicated that Gal-8 functioned to cluster VEGFR-3 on cell surface. These findings indicate that Gal-8 cross-links and clusters VEGFR-3 on the cell surface to activate lymphangiogenic signaling pathways. The galectin-glycan lattices increase receptor residency time by inhibiting endocytosis of glycoprotein receptors from the cell surface, and this in turn increases the magnitude or duration of signaling from the cell surface (Garner, et al. 2008. *Biochem Soc Trans* 36:1472-1477; Rabinovich, G. A., et al. 2007. *Curr Opin Struct Biol* 17:513-520). Thus, the synergistic effect of Gal-8 on VEGF-C-induced lymphangiogenesis observed in the examples herein is likely due to the formation of Gal-8-VEGFR-3 lattices.

VEGF-C-induced lymphangiogenesis was found to be inhibited by blocking the function of extracellular Gal-8. However, VEGFR-3 knockdown did not inhibit Gal-8-induced sprouting and only partially inhibits Gal-8-induced activation of AKT and extracellular signal-regulated kinases (ERK). Therefore, VEGF-C-induced lymphangiogenesis was observed to be dependent on extracellular Gal-8 and the role of VEGFR-3 in the molecular mechanism of Gal-8-induced lymphangiogenesis is limited. Hence, examples herein were designed to test whether Gal-8-mediated lymphangiogenesis was dependent on another lymphangiogenic molecule, PDPN. The characteristics of PDPN included that PDPN binds to Gal-8 in a carbohydrate-dependent manner, that PDPN contains high affinity glycans of Gal-8 (3'-sialylated glycans), that Gal-8 clusters PDPN on cell surface, and unlike the knockdown of VEGFR-3, knockdown of PDPN abrogates Gal-8-induced lymphangiogenesis and these characteristics indicate that PDPN is a key player in the mechanism of Gal-8-induced lymphangiogenesis. PDPN plays a critical role in VEGF-C-mediated process of lymphangiogenesis. VEGFR-3- and PDPN-mediated pathways have been independently shown to promote lymphangiogenesis, but the relationship in the molecular mechanism of the two pathways has not been demonstrated. Of note, PDPN knockdown attenuated only VEGF-C-induced AKT, but not ERK, phosphorylation (FIG. 7), indicating that VEGF-C-induced AKT phosphorylation is PDPN-dependent. These data indicate that AKT phosphorylation through PDPN is essential for VEGF-C signaling in LECs. PDPN knockdown in vitro and PDPN deletion in vivo inhibited VEGF-C-induced lymphangiogenesis, indicating that a cross-talk between VEGFR-3 and PDPN pathways played a critical role in the process of lymphangiogenesis. This is an important conceptual advance in the understanding of the molecular mechanism of VEGF-C/VEGFR-3 lymphangiogenic pathway.

Figure 11:
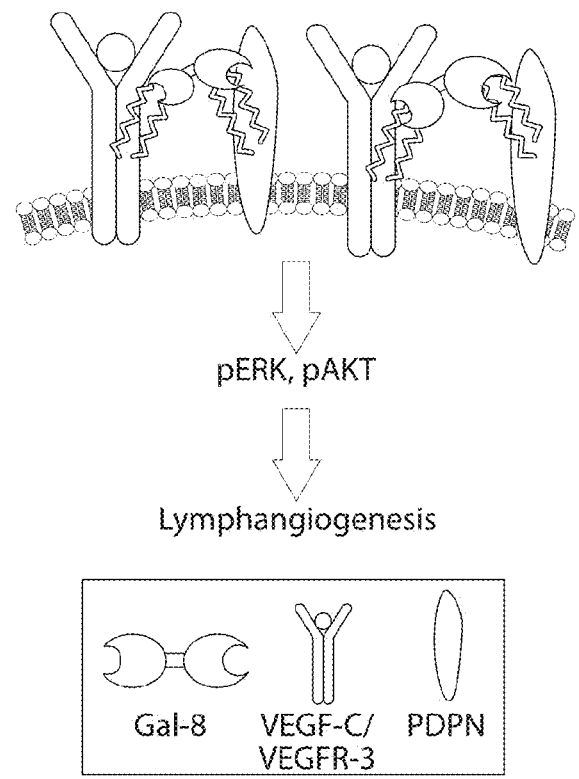
FIG. 11 is a schematic drawing showing a model the proposed herein of Gal-8-mediated lymphangiogenesis. According to this model, Gal-8 causes cross-links and clusters of VEGFR-3 and PDPN on the cell surface. The clustering activates lymphangiogenic signaling pathways that modulate events such as endothelial cell migration and sprouting in the lymphangiogenic cascade. This model is based on data found in examples herein which demonstrate that (i) Gal-8 binds to and subsequently clusters VEGFR-3 and PDPN on cell surface, (ii) VEGF-C-induced lymphangiogenesis is dependent on Gal-8 and PDPN, and (iii) Gal-8 activates AKT and ERK pathways and promotes lymphangiogenesis in vivo and in vitro in a carbohydrate-dependent manner.

Without being limited by a particular theory or mechanism of action the following model of Gal-8-mediated lymphangiogenesis is proposed (FIG. 11) based on the examples herein. According to this model, Gal-8 cross-links and clusters VEGFR-3 and PDPN on the cell surface. The clustering of VEGFR-3 and PDPN activates lymphangiogenic signaling pathways that modulate events such as endothelial cell migration and sprouting in the lymphangiogenic cascade.

The fact that a dominant negative inhibitor of Gal-8 and the pan inhibitor of galectin dampen the process of lymphangiogenesis have broad implications for developing novel therapeutic strategies for conditions resulting from pathological lymphangiogenesis, such as cancer metastasis and transplant rejection.

Pharmaceutical Compositions

In one aspect of the present invention, pharmaceutical compositions are provided, such that these compositions comprise at least one inhibitor of an activity of a galectin-8 protein, and optionally comprise a pharmaceutically acceptable carrier. In certain embodiments, these compositions optionally further comprise one or more additional therapeutic agents. In certain embodiments, the additional therapeutic agent or agents are selected from the group consisting of growth factors, anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), hepatocyte growth factor (HGF), B vitamins such as biotin, and hyaluronic acid.

The phrases "pharmaceutically acceptable carrier" and "pharmaceutically suitable carrier" are used interchangeably herein and include any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences* Ed. by Gennaro, Mack Publishing, Easton, Pa., 1995 discloses various carriers used in formulating pharmaceutical compositions and known techniques for the preparation thereof. Some examples of materials which can serve as pharmaceutically acceptable carriers include, but are not limited to, sugars such as glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, and other non-toxic compatible lubricants such as sodium lauryl sulfate and magnesium stearate, and coloring agents, releasing agents, coating agents, sweetening, flavoring and perfuming agents, preservatives and antioxidants can also be present in the composition, according to the judgment of the formulator.

Therapeutically Effective Dose

The invention provides methods for the treatment of the lymphangiogenesis-related disorder, the methods comprising administering a therapeutically effective amount of a pharmaceutical composition comprising active agents that inhibit galectin-8 to a subject in need thereof, in such amounts and for such time as is necessary to achieve the desired result. It will be appreciated that this encompasses administering an inventive pharmaceutical agent as a therapeutic measure to inhibit lymphangiogenesis, or as a prophylactic measure to minimize complications associated with a lymphangiogenesis-associated disorder such as dry eye disease, organ transplant, cancers and certain inflammatory diseases. In certain embodiments a "therapeutically effective amount" of the pharmaceutical composition is that amount effective for modulating the lymphangiogenesis-related disorder. The compositions, according to the method of the present invention, may be administered using any amount and any route of administration effective for treating the eye or other tissue. The exact dosage is chosen by the individual physician in view of the patient to be treated. Dosage and administration are adjusted to provide sufficient levels of the active agent(s) or to maintain the desired effect. Additional factors which may be taken into account include the severity of the disease state, e.g., extent of lymphangiogenesis, history of the condition; age, weight and gender of the patient; diet, time and frequency of administration; drug combinations; reaction sensitivities; and tolerance/response to therapy. Long acting pharmaceutical compositions might be administered several times a day, every day, 3 to 4 days, every week, or once every two weeks depending on half-life and clearance rate of the particular composition.

The active agents of the invention are preferably formulated in dosage unit form for ease of administration and uniformity of dosage. The expression "dosage unit form" as used herein refers to a physically discrete unit of active agent appropriate for the patient to be treated. It will be understood, however, that the total daily usage of the compositions will be decided by the attending physician within the scope of sound medical judgment. For any active agent, the therapeutically effective dose can be estimated initially either in cell culture assays or in animal models, usually mice, rabbits, dogs, or pigs. The animal model is also used to achieve a desirable concentration range and route of administration. A therapeutically effective dose refers to that amount of active agent that ameliorates the symptoms or condition. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosage for human use.

Administration of Pharmaceutical Compositions

After formulation with an appropriate pharmaceutically acceptable carrier in a desired dosage, the pharmaceutical compositions of this invention can be administered to humans and other mammals topically such as ocularly (as by gels, ointments, or drops), i.e., as applied directly to external tissues of the eye. Alternative and additional routes such as injection into the eye including invitreally, subtenonally, and subretinally, or orally, rectally, parenterally, intracisternally, intravaginally, intraperitoneally, bucally, or nasally, depending on the severity of the condition being treated, are envisioned. Ocular injections include intra-ocular injection into the aqueous or the vitreous humor, or injection into the external layers of the eye, such as via subconjunctival injection or subtenon injection. Oral administration is envisioned as effective for synthetic small molecule inhibitors.

Liquid dosage forms for ocular administration include buffers and solubilizing agents, preferred diluents such as water, preservatives such as thymosol, and one or more biopolymers or polymers for conditioning the solution, such as polyethylene glycol, hydroxypropylmethylcellulose, sodium hyaluronate, sodium polyacrylate or tamarind gum.

Liquid dosage forms for oral administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, ocular or cutaneous infections may be treated with aqueous drops, a mist, an emulsion, or a cream. Administration may be therapeutic or it may be prophylactic. Prophylactic formulations may be present or applied to the site of potential wounds, or to sources of wounds. The invention includes ophthalmological devices, surgical devices, audiological devices or products which contain disclosed compositions (e.g., gauze bandages or strips), and methods of making or using such devices or products. These devices may be coated with, impregnated with, bonded to or otherwise treated with a disclosed composition.

The ointments, pastes, creams, and gels may contain, in addition to an active agent of this invention, excipients such as animal and vegetable fats, oils, waxes, paraffins, starch, tragacanth, cellulose derivatives, polyethylene glycols, silicones, bentonites, silicic acid, talc, zinc oxide, or mixtures thereof.

Powders and sprays can contain, in addition to the agents of this invention, excipients such as talc, silicic acid, aluminum hydroxide, calcium silicates, polyamide powder, or mixtures of these substances. Sprays can additionally contain customary propellants such as chlorofluorohydrocarbons.

Transdermal patches have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent may be accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the active agent(s) of this invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as milk sugar and high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed. manner. Examples of embedding compositions which can be used include polymeric substances and waxes.

Uses of Pharmaceutical Compositions

As discussed herein and described in greater detail in the Examples, an inhibitor of galectin-8 is useful to treat or modulate lymphangiogenesis conditions by binding VEGF-C receptors or by binding to oligosaccharide chains of secretory mucins to the transmembrane muscins (or other glycoproteins). In general, it is believed that these inhibitors of galectins will be clinically useful in suppressing development of lymphangiogenic disorders including for example conditions associated with excessive neovascularization, or fibrosis. For example the inhibitor of galectin expression or galectin activity is effective to treat a condition associated with a disease, e.g., a cancer, dry eye disease and organ transplant.

In general, it is shown herein that these inhibitors of galectin-8 are clinically useful in suppressing lymphangiogenesis associated with any epithelial tissue including but not limited to the skin epithelium; the corneal epithelium; the lining of the gastrointestinal tract; the lung epithelium; and the inner surface of kidney tubules, of blood vessels, of the uterus, of the vagina, of the urethra, or of the respiratory tract.

Pharmaceutical compositions containing an inhibitor of a galectin-8 is, for example herein, useful to promote a normal level of lymphangiogenesis.

Inhibitors of galectin-8 for example are useful by methods herein to treat gastrointestinal ulcers and help heal the mucosal lining and regeneration of glandular mucosa and duodenal mucosal lining more rapidly. Inflammatory bowel diseases, such as Crohn's disease and ulcerative colitis, are diseases which result in destruction of the mucosal surface of the small or large intestine, respectively. Thus, inhibitors of galectin-8 are used to limit lymphangiogenesis during resurfacing of the mucosal surface to aid more rapid healing and to prevent or attenuate progression of inflammatory bowel disease. Galectin-8 is expected to bind mucin and facilitate its adhesion to the apical surface of the epithelium and inhibitors of these proteins are therefore used to protect the gastrointestinal tract from injurious substances that are ingested or following surgery, and to prevent or attenuate mucositis, esophagitis, or gastritis (e.g., to heal lesions associated with oral, esophageal, intestinal, colonic, rectal, and anal ulcers).

Inhibitors of galectin-8 are administered prophylactically to reduce or prevent damage by excess lymphangiogenesis to the eyes and lungs caused by various pathological states. For example, galectin-8 in appropriate amounts is used to promote the repair of alveoli and bronchiolar epithelium to prevent, attenuate, or treat acute or chronic lung damage can be controlled by compositions herein. Emphysema, which results in the progressive loss of alveoli, and inhalation injuries, i.e., resulting from smoke inhalation and burns, that cause necrosis of the bronchiolar epithelium and alveoli can be effectively treated using inhibitors of galectin-8, as can damage attributable to chemotherapy, radiation treatment, lung cancer, asthma, black lung and other lung damaging conditions, following galectin-8 treatment.

It will be appreciated that the therapeutic methods encompassed by the present invention are not limited to treating wounds in humans, but may be used to treat wounds in any mammal including but not limited to bovine, canine, feline, caprine, ovine, porcine, murine, and equine species. When treating wounds in a given species, it is preferred, but not required, that the inhibitory compositions herein galectin-8 be used.

A portion of this work was published April 2015 as a paper in the Journal of the Federation of American Societies for Experimental Biology, entitled, "Pathological Lymphangiogenesis Is Regulated by Galectin-8-Dependent Crosstalk among VEGF-C, Podoplanin and Integrin Pathways", authored by Wei-Sheng Chen, Zhiyi Cao, Hakon Leffler, Ulf Nilsson, Lijun Xia and Noorjahan Panjwani (Chen et al. FASEB J April 2015 29:890.6), which is hereby incorporated by reference herein in its entirety.

The invention now having been fully described, it is further exemplified by the following examples and claims. Those skilled in the art will recognize or be able to ascertain using no more than routine experimentation, numerous equivalents to the specific procedures described herein. Such equivalents are within the scope of the present invention and claims. The contents of all references including issued patents and published patent applications cited in this application are hereby incorporated by reference in their entirety.

EXAMPLES

Example 1

Subject Animals

Lymphatic-specific Prox1-EGFP reporter mice (FVB background) (Choi, I., et al. 2011 *Blood* 117:362-365) were purchased from Mutant Mouse Regional Resource Centers, FVB/NCr1 mice were purchased from Charles River Laboratories, and C57BL/6 mice were purchased from Jackson Laboratory. Mice with inducible deletion of PDPN (Pdpn$^{f/f}$;CagCre) and wild-type littermates (Pdpn$^{f/w}$;CagCre) in mixed background (C57BL/6 and 129/Sv) were generated. Herzog, B. H., et al. 2013. *Nature* 502:105-109. PDPN deletion was accomplished by administering tamoxifen orally (20 µg each day) from P1 to P6. After weaning, the mice were orally administered 1 mg tamoxifen weekly.

Example 2

Expression and Purification of Recombinant Galectins

Recombinant galectins were expressed and purified as described previously (Carlsson, S., et al. 2007. *Glycobiology* 17:906-912; Carlsson, S., et al. 2007. *Glycobiology* 17:663-676; Diskin, S., et al. 2009. *Glycobiology* 19:29-37; Kuwabara, I., et al. 2002. J Biol Chem 277:3487-3497; Suryawanshi, A., et al. 2013. *J Immunol* 190:6397-6409). Endotoxin was removed by Detoxi-Gel endotoxin removing gel (Thermo Scientific) and endotoxin levels were detected by ToxinSensor chromogenic LAL endotoxin assay kit (Genscript). Endotoxin levels of all recombinant galectins used were <0.1 EU/µg.

Example 3

Gal-8 Immunohistochemistry Staining of Normal and Inflamed Corneas

Human corneas were obtained from the Ophthalmology Department of Tufts Medical Center. Normal human corneas were harvested from eyes which were enucleated due to choroidal melanoma (n=2) and uveal malignant melanoma (n=2). Inflamed human corneas were obtained at the time of keratoplasty from patients with failed corneal graft (n=6), bacterial keratitis (n=4) and *Acanthamoeba keratitis* (n=2). Tissue sections of normal and inflamed corneas were processed for immunolocalization of Gal-8 using a procedure as described in Panjwani, N., et al. 1986. *Invest Ophthalmol Vis Sci* 27:1280-1284. Paraffin-embedded sections were deparaffinized, rehydrated and incubated with rabbit anti-Gal-8 primary antibody (1:100 dilution in 1% BSA/PBS, 1 hr, 37° C., Novus) and a biotinylated secondary antibody (30 min, 37° C., R&D Systems). Sections were subsequently incubated with HSS-HRP (30 min, 25° C., R&D Systems), and a DAB/AEC chromogen solution (37° C., R&D Systems). Images were acquired by EVOS XL Core cell imaging system (Invitrogen).

Example 4

Gal-8 Immunohistochemistry of Normal and Inflamed Mouse Corneas

To induce inflammation, mouse corneas (8-week old C57BL/6 mice) were treated with thermal cautery or silver nitrate cautery. For thermal cautery, five light burns were applied to the central cornea of the right eye of each animal using the straight fine tip of a hand-held thermal cauterizer (Fine Science Tools) and ophthalmic antibiotics were topically applied to the operated eyes. For silver nitrate cautery, silver nitrate applicators (Grafco) were applied on the central cornea of the right eye for 5 seconds under a surgical microscope. The corneas were rinsed with 2 ml of PBS, and ophthalmic antibiotics were topically applied to the operated eyes. The eyes with thermal or silver nitrate cautery were harvested on post-surgery day 1 and day 5, respectively. Contralateral eyes served as normal controls. Frozen sections of the eyes (12-µm thick) were fixed with 4% paraformaldehyde/PBS, blocked with 1% BSA/PBS, and were then incubated with rabbit anti-Gal-8 primary antibody (1:100 dilution, 4° C. overnight, Novus), and Alexa Fluor® 488 anti-rabbit secondary antibody (1:300 dilution, 1 hr, 25°

C., Invitrogen). Fluorescent images were acquired by Leica TCS SPE imaging system (Leica).

Example 5

Corneal Mouse Micropocket Lymphangiogenesis Assay

The corneal micropocket lymphangiogenesis assay was performed using implants containing a test agent, hydron (polyhydroxylmethylmethacrylate), and sucralfate (Cao, R., et al. 2011. *Nat Protoc* 6:817-826; Rogers, M. S., et al. 2007. *Nat Protoc* 2:2545-2550). Test agents included full-length Gal-8 (40-320 ng/pellet) and VEGF-C (160 ng/pellet). Implants containing hydron and sucralfate alone served as negative controls. The mice were anesthetized by intraperitoneal injection of a mixture of ketamine (90-120 mg/kg) and xylazine (10 mg/kg). The eyes were topically anesthetized with proparacaine and were gently proptosed (forwardly displaced) with forceps. Using a corneal blade and a stereoscope, intrastromal linear keratotomy was performed about 2 mm from the limbus. Using a von Graefe knife (Miltex), a pocket was extended towards the limbus, and the pellet was maneuvered into the pocket. The wound was coated with a veterinary ophthalmic ointment (Akorn) to prevent infection. Mouse corneas were harvested 7 days after pellet implantation, fixed in 4% paraformaldehyde/PBS (1 hour at 4° C.), washed with PBS, and fixed again in iced acetone (15 min at −20° C.). To quantitate the extent of lymphangiogenesis in Prox-1-EGFP reporter mice, flat mounts of the dissected corneas were evaluated by fluorescence microscopy. Fluorescent images were acquired by EVOS FL cell imaging system (Invitrogen), and vessel areas were calculated using the formula (Rogers, M. S., et al. 2007. Nat Protoc 2:2545-2550): vessel area=pellet distance×vessel length×clock hours×0.2 rt. To quantitate the extent of lymphangiogenesis in WT and PDPN-deficient mice, corneas were stained with eFluor 570-anti-mouse LYVE-1 (clone ALY7, eBioScience, and 1:75) in 10% goat serum/0.2% Triton X-100/PBS overnight, 4° C. After several washes with 0.2% Triton X-100/PBS, the corneas were flattened and mounted with VECTASHIELD mounting medium (Vector Laboratories) and evaluated by fluorescence microscopy. In some examples, for comparisons, corneas were stained with Alexa Fluor® 488-anti-mouse CD31 (clone MEC13.3, 1:100, BioLegend) to visualize blood vessels.

Example 6

Mouse Model of Suture-Induced Inflammatory Corneal Lymphangiogenesis

The mouse model of suture-induced lymphangiogenesis was used as described in Cho, Y. K., et al. 2012. *Invest Ophthalmol Vis Sci* 53:685-692 and Cursiefen, C., et al. 2004. *Invest Ophthalmol Vis Sci* 45:1117-1124. Two 11-0 sutures were placed intrastromally about 2 mm from the limbus at the 12 and 6 o'clock positions in the Prox1-EGFP reporter mice. After surgery, a veterinary ophthalmic ointment was applied to prevent infection. Sutures were left in place for 7 days. To assess the effect of galectin inhibitors on suture-induced lymphangiogenesis, 10 μL of vehicle (PBS), TDG (200 mM in PBS), or Gal-8N (15 μg in PBS) were subconjunctivally injected on post-surgery days 0, 2, 4 and 6 using a 32 gauge needle with a 10 μL syringe (Hamilton). On day 7 post-surgery, mouse corneas were harvested and processed for staining with anti-LYVE-1 as described in examples herein. The areas of lymphatic vessels covering the whole corneas were calculated.

Example 7

Knockdown of VEGFR-3, PDPN and Nrp2

ON-TARGET plus human VEGFR-3 siRNA SMART pool was purchased from Dharmacon/Thermo. Oligonucleotide siRNA duplexes targeting PDPN and AllStars Negative control siRNA were purchased from Qiagen. Hs_PDPN_1 and Hs_T1A-2_7 siRNA were designated as PDPN siRNA1 and siRNA4, respectively. The transfection of siRNA in primary LECs (Lonza) was carried out with the Lipofectamine 2000 reagent (Invitrogen). Lipofectamine 2000 (3 μL) in 250 μL of Opti-MEM medium (Invitrogen) and 3 μL of siRNA (20 μM) in 250 μL of Opti-MEM medium were incubated separately for 5 min at 25° C., and the two mixtures were combined and incubated for an additional 20 min to form Lipofectamine 2000-siRNA complexes. At the end of the incubation period, serum-free Opti-MEM (1.5 ml) was added to each well of a 6-well plate and 500 μL aliquots of Lipofectamine 2000-siRNA complex were added to each well. Final concentration of siRNA was 30 nM. After 3 hours incubation, media were replaced with complete EGM-2MV medium (Lonza). The same procedure was repeated on the next day and knockdown efficiency was assessed by western blot after 48 hours transfection.

Example 8

LEC Sprouting Assay

LEC spheroids were generated by seeding primary LECs at passage 4 or 5 in each well of 384-well hanging-drop plates (3D Biomatrix) in complete EGM-2 MV medium containing 0.25% methyl cellulose according to the manufacturer's instructions (750 cells/well). After 18 hours, LEC spheroids were collected, resuspended in serum-free EBM-2 basal medium, and mixed with collagen solution (PureCol collagen, Advanced BioMatrix, 2.2 mg/ml in M199 medium, pH adjusted to 7.4 with $NaHCO_3$ and NaOH). Aliquots of the LEC spheroid/collagen mixture (250 μl/well of 48-well plate) were incubated in the presence or absence of various test agents for 24 hr. At the end of the incubation period, spheroids were stained with Calcein AM (Invitrogen, 1 μg/mL, 37° C., and 30 min). Fluorescent images were acquired using the EVOS FL cell imaging system, pixels were inverted for better visualization and cumulative length of each sprout was calculated. Results were expressed as fold change compared to corresponding controls. It was observed that sprout lengths vary from passages to passages. Test agents used included thiodigalactoside (10 to 50 mM, Carbosynth), 3'-sialyl lactose (2 to 10 mM, Carbosynth), 6'-sialyl lactose (2 to 10 mM, Carbosynth), LY294002 (20 μM, Abeam), U0126 (20 μM, Abeam), PD0325901 (1 μM, Selleckchem), human VEGFR-3-Fc chimera (10 μg/ml, R&D), human VEGFR-2-Fc chimera (10 μg/ml, R&D), Avastin (10 μg/ml, bevacizumab, Genentech/Roche), human control IgG (10 μg/ml, Southern Biotech), anti-human podoplanin functional grade antibody (10 μg/ml, eBioscience), and rat IgG2a κ isotype control functional grade antibody (10 μg/ml, eBioscience).

Example 9

Affinity Precipitation Assay

Five mg of plant lectins (Vector Labs) and galectins were conjugated to 330 mg of Pierce® NHS-activated agarose dry resin in accordance with the manufacturer's instructions (Thermo Scientific). Primary LECs (Lonza) were lysed in Triton lysis buffer (20 mM Tris-HCl, pH 7.4; 150 mM NaCl; 0.5% Triton X-100 with protease inhibitor cocktail). LEC lysates (250 µg in 500 µL lysis buffer supplemented with 10 mM $MgCl_2$) were incubated with 40 µL (50% slurry) of agarose-conjugated lectins (4° C., overnight). Beads were pelleted by centrifugation at 3000 rpm for 1 min. Nonspecific binding proteins were removed by washing the beads with Triton lysis buffer once and PBS twice. Supernatants were discarded; bound proteins were eluted by boiling the beads with 20 µL of 2× Laemmli sample buffer for 7 min, and examined by western blotting.

Example 10

Western Blot Analysis

Primary LECs were lysed with Triton lysis buffer supplemented with protease inhibitor cocktail and Phos-STOP phosphatase inhibitor cocktail (Roche), and subjected to electrophoresis in 4-15% SDS-PAGE gels (Bio-Rad). Protein blots of the gels were blocked with 0.5×Odyssey® blocking buffer (OBB, Li-COR). For AKT and ERK signaling, blots were incubated with primary antibodies (rabbit anti-ERK1/2, 1:7500, Cell Signaling Technology; mouse anti-phospho-ERK1/2, Thr202/Tyr204, 1:2000, Cell Signaling Technology; mouse anti-AKT1/2/3, 1:2000, Cell Signaling Technology; rabbit anti-phospho-AKT, Ser473, 1:1500, Cell Signaling Technology) overnight at 4° C. Blots were washed with 0.5% Tween-20/PBS three times, and were incubated with appropriate secondary antibodies (donkey anti-rabbit IRDye 680LT and anti-mouse IRDye 800CW, Li-Cor) for 45 min at 25° C. The blots were scanned by an Odyssey® Infrared Imaging System using Image Studio v2.0 software (Li-COR). After scanning, the blots were stripped with NewBlot Nitrocellulose stripping buffer (25° C., 10 min, Li-Cor) and were re-probed with primary antibodies (rabbit anti-VEGFR-3, clone C-20, 1:500, Santa Cruz Biotechnology; rat anti-human podoplanin, 1:2000, BioLegend; mouse anti-GAPDH, clone 6C5, 1:10000, Santa Cruz Biotechnology; mouse anti-β-actin, clone AC-15, 1:10000, Santa Cruz. Biotechnology) overnight at 4° C. The blots were developed using appropriate secondary antibodies (goat anti-rabbit IRDye 800CW; anti-rat IRDye 800CW; anti-mouse IRDye 680LT, 1:10000 dilution, Li-Cor) for 45 min at 25° C. Signals were detected by Odyssey® Infrared Imaging System.

Example 11

LEC Migration Assay

Transwell (6.5 mm) plates with 8 µm-pore polycarbonate membrane inserts (Corning) were used in the migration assay. The lower-sides of the insert membranes were coated with 400 µL of fibronectin (10 µg/ml, Sigma) or galectin-8 (0.5 µM) at 37° C., overnight and then the inserts were blocked with 0.1% BSA in PBS, 37° C., 3 hours. LECs were serum-starved in serum-free EBM-2 medium overnight, detached with StemPro® Accutase® cell dissociation reagent, and resuspended in serum-free EBM-2 medium ($2 \times 10^5$ cells/ml). Aliquots of LEC suspension (200 µL of $2 \times 10^5$ cells/ml) were added to the upper chamber. The bottom chamber was filled with 600 µL of serum-free EBM-2 and the plates were incubated at 37° C. for 2 hours. Inserts were fixed in absolute methanol (6 min, 25° C.) and stained with Giemsa stain (40 min, 25° C., Sigma) per manufacturer's instructions. Membranes were wiped free of cells on the upper surface and mounted with Permount mounting medium (Fisher) on glass slides. The number of migrating cells in each condition were counted in 4 random fields at 10× magnification, averaged, and normalized to control condition to generate percent-change in migration activity. In some assays, the cells were incubated in the presence of isotype control Ab (10 µg/ml, eBioScience) or the anti-PDPN functional blocking Ab (10 µg/ml, eBioScience). Using control BSA-coated membranes data showed that no LECs attached, therefore data from this group were not included in the graphs.

Example 12

Immunoprecipitation

Mouse isotype antibody (15 µg, Santa Cruz Biotechnology) and anti-PDPN (15 µg, clone E-1, Santa Cruz Biotechnology) were immobilized onto AminoLink Plus coupling resin (Pierce) by sodium cyanoborohydride according to manufacturer's instructions. Primary LECs were serum-starved overnight and treated with galectin-8 (0.2 µM) for 15 min at 37° C. After treatment, cells were lysed with IP lysis/wash buffer (25 mM Tris, 150 mM NaCl, 1 mM EDTA, 1% NP-40, 5% glycerol; pH 7.4) supplemented with protease inhibitor cocktails (Roche). After centrifugation (10 min, 13,000 rpm), supernatants (500 µg protein lysates) were pre-cleared by incubation for 1 hour with Pierce control agarose resin at 4° C. The clarified samples were incubated with the Ab-conjugated agarose resins overnight at 4° C. Immunoprecipitates were washed three times with IP lysis/wash buffer and once with conditioning buffer provided by the kit (Pierce). The bound proteins were eluted with low pH elution buffer, neutralized with Tris-HCl (pH 9.0), and analyzed with control inputs by western blotting using anti-integrin α1 (1:1,000, Abcam), anti-integrin α5 (clone H-104, 1:1,000, Santa Cruz Biotechnology), anti-integrin β1 (clone N-20, 1:1,000, Santa Cruz Biotechnology), anti-PDPN, anti-galectin-8 (clone NBP1-66520, 1:1,000, Novus Biologicals) and anti-GAPDH as described in examples herein.

Example 13

Immunocytochemistry Staining

Primary LECs were treated with Gal-8 (0.5 µM) for 15 min at 37° C., washed with PBS three times, fixed with 4% paraformaldehyde/PBS (10 min, 25° C.), and permeabilized with 0.2% Triton X-100/PBS (5 min, 25° C.). Cells were blocked with Image-iT® signal enhancer (30 min, 25° C., Invitrogen) and incubated with primary antibodies (rat anti-human PDPN, 1:300, BioLegend; mouse anti-human VEGFR-3, 9D9F9, 1:100, BioLegend; rabbit anti-Gal-8, H-80, 1:100, Santa Cruz Biotechnology) in 2% BSA/PBS at 4° C. overnight. The cells were then washed with 2% BSA/PBS three times and incubated with appropriate secondary antibodies (Alexa Fluor® 488 anti-mouse, 1:200, Invitrogen; Alexa Fluor® 568 anti-rabbit, 1:200, Invitrogen; Alexa Fluor 647® anti-rat, 1:300, Jackson ImmunoResearch) at 25° C. for 1 hr. Cells were washed with PBS, slides were mounted with ProLong Gold antifade reagent with DAPI (Invitrogen) and were examined with the Leica TCS SPE imaging system (Leica).

Example 14

Analyses of Cell Surface Expression of VEGFR-3 and PDPN by Flow Cytometry

Primary LECs were serum-starved overnight in basal EBM-2 medium. The cells were incubated with or without VEGF-C (50 ng/ml, PeproTech) or Gal-8 (0.2 µM) in serum-free EBM-2 medium for 10 and 30 min. At the end of the incubation period, cells were lifted with StemPro® Accutase® cell dissociation reagent (Invitrogen), washed with PBS and fixed with 4% paraformaldehyde/PBS on ice for 10 min, and were then stained using rat anti-human PDPN (1:500, BioLegend) and mouse anti-human VEGFR-3 (clone 9D9F9) (1:100, BioLegend) primary antibodies in cell staining buffer (BioLegend, 45 min on ice) and Alexa Fluor® 488 donkey anti-rat and Alexa Fluor® 647 anti-mouse secondary antibodies (1:1000, Invitrogen, 30 min on ice). For negative control, the primary antibodies were omitted. The stained cells were fixed with 2% paraformaldehyde/PBS, analyzed with BD FACSCalibur, and the mean fluorescence intensity of VEGFR-3 and PDPN were quantified with the FlowJo software (version 9.5.2).

Example 15

Glycosidase Treatment

To determine whether treatment with neuraminidase inhibits VEGFR-3 and PDPN interaction with Gal-8, primary LECs ($3 \times 10^5$ cells) were lifted with StemPro® Accutase® cell dissociation reagent, resuspended in 100 µL of PBS with 200 units of α2-3 neuraminidase (BioLabs), or 100 µL of G7 reaction buffer containing 2,000 units of peptide-N-glycosidase F (BioLabs) and 3 U of DNase I (Fisher). The reaction mixtures were incubated at 37° C. for 1 hr. Cell lysates were subjected to affinity precipitation using Gal-8-conjugated agarose beads and bound proteins were analyzed by western blot analysis using anti-VEGFR-3 and anti-PDPN as described in examples herein.

Example 16

Statistics

Data in all figures are presented as mean±SEM. All results were confirmed in two or more independent examples. Data were analyzed using paired two-tailed Student's t test or one-way ANOVA in Prism 6 (GraphPad) as indicated in figure legends. P value of less than 0.05 was considered statistically significant.

Example 17

Gal-8 Expression is Markedly Upregulated in Inflamed Human and Mouse Corneas Corneal epithelium is a prototype-stratified squamous epithelium and is composed of 5-6 layers of cells. Posterior to the epithelial basement membrane is corneal stroma. During inflammation, inflammatory cells infiltrate superficial or deep stroma depending on the location of injury. In corneas of patients with graft failure and bacterial keratitis numerous inflammatory cells were detected in the stroma as highlighted by periodic acid Schiff (PAS) staining (FIG. 1A-FIG. 1F). To assess the expression pattern of Gal-8 in normal and inflamed human corneas, corneal buttons removed at keratoplasty from patients with corneal graft failure and bacterial keratitis were processed for immunostaining with anti-Gal-8. Normal corneas expressed less amount of Gal-8 (FIG. 1D). In contrast, robust Gal-8 immunoreactivity was detected in corneas of patients with corneal graft failure and bacterial keratitis. Corneal buttons from six patients with graft failure and six patients with microbial keratitis were examined with reproducible results. In western blot analysis, the antibody reacted with recombinant Gal-8 and the antibody did not react to a number of other recombinant galectins including Gal-1, -3, -7 and -9, indicating the specificity of the antibody.

To determine the expression pattern of Gal-8 in normal and inflamed mouse corneas, two different murine models of corneal inflammation were used. Corneas treated with either thermal cautery or silver nitrate cautery were allowed partially to heal in vivo and were then processed for immunostaining with anti-Gal-8 antibody. As observed with normal human corneas, Gal-8 expression was minimal in normal mouse corneas with some immunoreactivity in corneal epithelium. In contrast, in cauterized corneas, intense Gal-8 immunoreactivity was detected in the stroma (FIG. 1G-FIG. 1I). Three corneas with thermal and $AgNO_3$ cautery each were analyzed with reproducible results. No immunoreactivity was detected in the control human or mouse corneas.

Example 18

Gal-8 Promotes Lymphangiogenesis In Vivo in a Dose-Dependent Manner

Avascular cornea has been extensively used as the in vivo model to investigate the molecular mechanism of hemangiogenesis and to examine the efficacy of the inhibitors and activators of hemangiogenesis (Cao, R., et al. 2011. *Nat Protoc* 6:817-826; Rogers, M. S., et al. 2007. *Nat Protoc* 2:2545-2550). Cornea has also proven to be an invaluable in vivo model for defining general mechanisms of lymphangiogenesis.

Figure 2B:
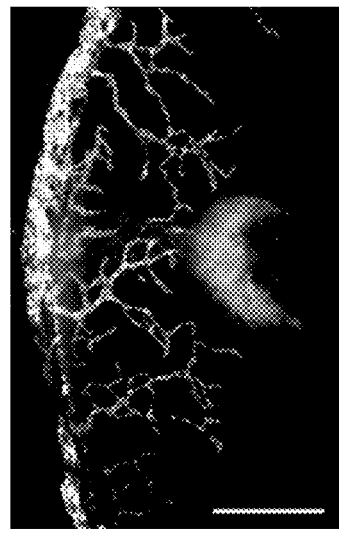

To determine whether Gal-8 plays a role in promoting lymphangiogenesis in vivo, the mouse corneal micropocket assay were used to assess Gal-8-mediated lymphangiogenesis. The vessel area, representing the extent of lymphangiogenesis, was calculated one week after pellets containing various concentrations of Gal-8 were implanted in the mouse corneas. In the concentration range tested (40-320 ng Gal-8/pellet), the extent of lymphangiogenesis were observed to have increased in a dose-dependent manner (FIG. 2A-FIG. 2B).

Example 19

Gal-8 Promotes Lymphangiogenesis In Vitro in a Dose- and Carbohydrate-Dependent Manner To better characterize the role of Gal-8 in the regulation of lymphangiogenesis, especially with respect to its molecular mechanism, an in vitro three-dimensional sprouting assay using LEC spheroids was used. The method uses primary LECs. More importantly, it allows easy manipulation of gene expression, for example by siRNA transfection as used in this study. Unlike 2D cultures in which different steps of vessel formation i.e. cell migration, proliferation and tube formation are addressed separately, the 3D-culture bridges the gap between in vitro and in vivo assay and provides an excellent approximation to in vivo lymphangiogenesis.

Figure 2C:
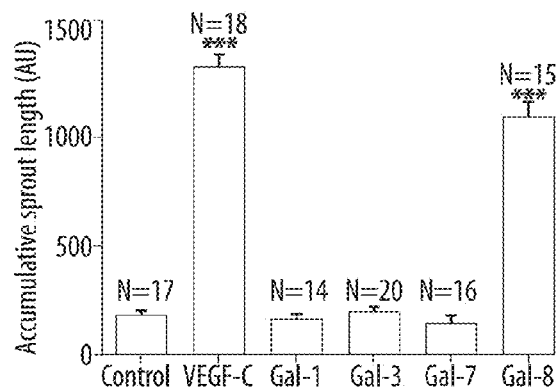
Figure 2D:
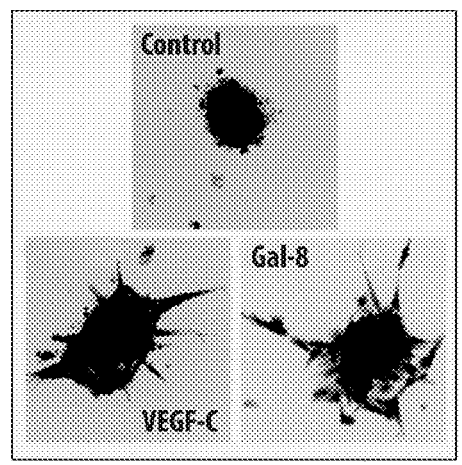

To assess the effect of galectins on LEC sprouting, LEC spheroids were embedded in a collagen matrix and incubated with media containing various test agents. After 24 hours, the cumulative length of the sprouts for each spheroid was quantified by ImageJ. In these assays, Gal-8, and not Gal-1, -3 or -7, were observed to have promoted LEC sprouting (FIG. 2B-FIG. 2C). The stimulatory effect of Gal-8 on LEC sprouting was observed to be concentration-dependent and was comparable to that of VEGF-C, which was used as a positive control (FIG. 2B-FIG. 2C). Multiple approaches were used to determine whether the stimulatory effect of Gal-8 on LEC sprouting was carbohydrate-dependent.

Figure 2E:
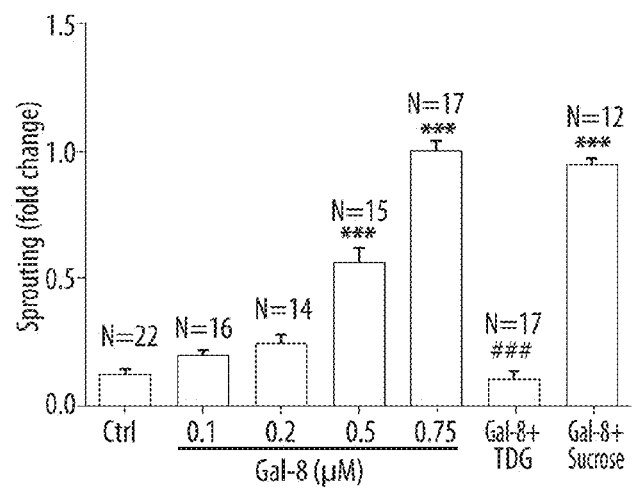
Figure 2F:
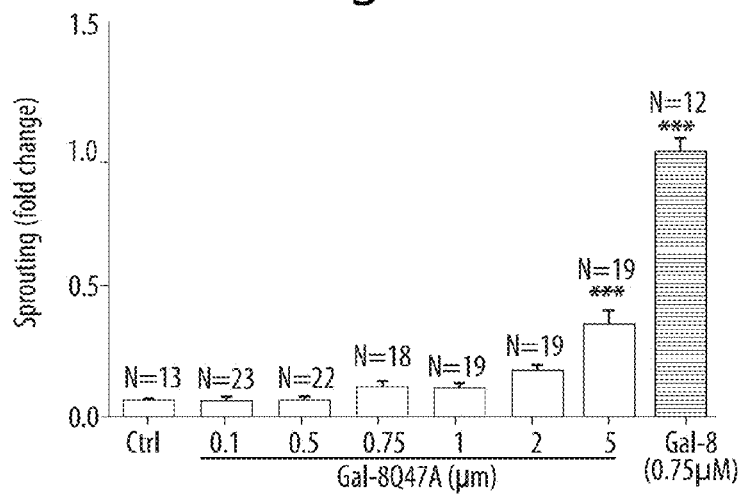

Gal-8-induced LEC sprouting was almost completely inhibited by thiodigalactoside (TDG, 20 mM; FIG. 2E), a pan inhibitor of galectins, indicating that at least one of the galectin CRDs was directly involved in the stimulatory effect of the exogenous lectin on LEC sprouting. Further, N-CRD of Gal-8 prefers α2,3-sialyl glycans and mainly contributes to its unique carbohydrate-binding specificity (Carlsson, S., et al. 2007. *Glycobiology* 17:663-676; Ideo, H., et al. 2011. *J Biol Chem* 286:11346-11355; Ideo, H., et al. 2003. *Glycobiology* 13:713-723). A Gal-8 mutant, Gal-8Q47A, which has lost its ability to bind to α2,3-sialylated glycans (Carlsson, S., et al. 2007. *Glycobiology* 17:906-912; Carlsson, S., et al. 2007. *Glycobiology* 17:663-676), was observed to not promote lymphangiogenesis (FIG. 2F), indicating that the N-CRD of Gal-8 is directly involved in the stimulatory effect of exogenous lectin on LEC sprouting.

Figure 2G:
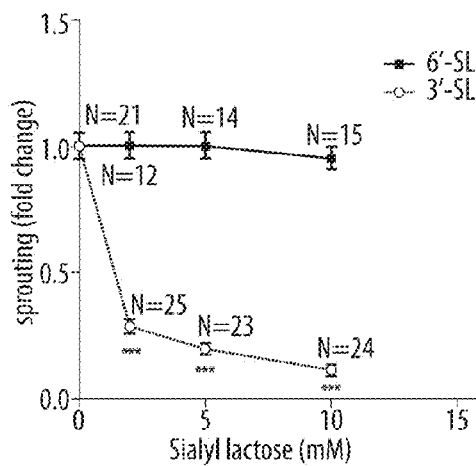

Further, to further verify the importance of N-CRD of Gal-8 in the Gal-8-induced LEC sprouting, the assays were conducted in the presence or absence of 3'-sialyllactose (3'-SL), which binds to N-CRD and does not bind to C-CRD of Gal-8 (Carlsson, S., et al. 2007. *Glycobiology* 17:663-676). At 2 mM concentration, the 3'-SL was observed to have inhibited Gal-8-induced LEC sprouting by 95% (FIG. 2G). In contrast, 6'-SL, which does not bind to either CRD of Gal-8, had no effect. These data conclusively establish that the stimulatory effect of Gal-8 on lymphangiogenesis is carbohydrate-dependent and that N-CRD of Gal-8 plays a critical role in the process of Gal-8-induced lymphangiogenesis.

Next, N-CRD was tested to determine if it can serve as a dominant negative inhibitor of Gal-8. The diverse functions of galectins are thought to result from the formation of galectin-glycan lattices. Most galectins form either dimers or oligomers on ligand encounter. This multivalency allows the formation of lectin-carbohydrate lattices to modulate signal transduction, cell-cell and cell-matrix interactions. Isolated CRDs, which retain their carbohydrate binding ability but are unable to dimerize or oligomerize and cross-link cell surface receptors, may compete with the carbohydrate-binding ability of the endogenous galectins and, hence, act as a dominant-negative inhibitor (John, C. M., et al. 2003. *Clin Cancer Res* 9:2374-2383; Markowska, A. I., et al. 2010. *J Exp Med* 207:1981-1993. *J Exp Med* 207:1981-1993; Yang, R. Y., et al. 1998. *Biochemistry* 37:4086-4092). As described herein, Gal-8 is made up of two distinct CRDs (N-CRD and C-CRD) joined by a "hinge" region. Properties of Gal-8 are mediated by the concerted action of its two CRDs (Levy, Y., et al. 2006. *Glycobiology* 16:463-476). Isolated CRDs of Gal-8 retain the carbohydrate binding activity but manifest impaired biological activity (Carlsson, S., et al. 2007. *Glycobiology* 17:663-676; Levy, Y., et al. 2006. *Glycobiology* 16:463-476), indicating that lectin requires cooperative interactions between the two CRDs. As described herein, N-CRD of Gal-8 is unique among galectins in exhibiting a very high affinity of α2,3-sialyl glycans.

Figure 2H:
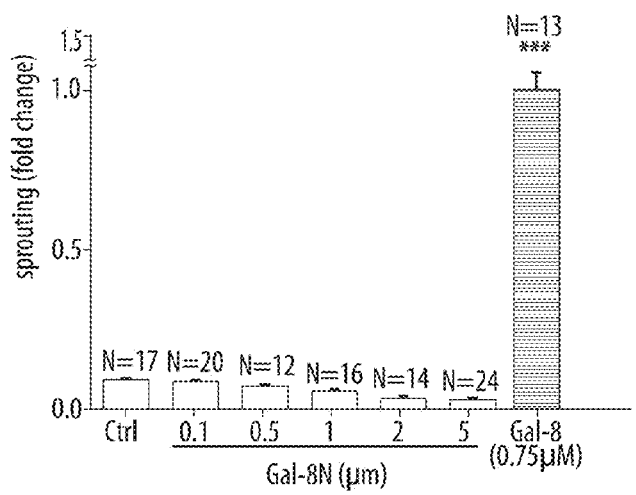
Figure 2I:
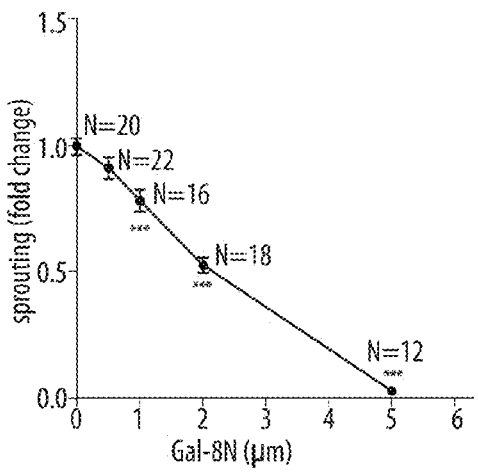

To determine whether the prolymphangiogenic property of Gal-8 is dependent on the cooperative action of both N-CRD and C-CRD of Gal-8, N-CRD was tested for its ability to promote lymphangiogenesis. Unlike full-length Gal-8, Gal-8N was observed to have failed to induce LEC sprouting (FIG. 2H). Moreover, Gal-8N effectively inhibited Gal-8-induced lymphangiogenesis in a dose-dependent manner (FIG. 2I). These results indicate that Gal-8N serves as a dominant negative inhibitor of Gal-8 and that α2,3-sialyl glycans recognized by Gal-8N and cooperative action of both Gal-8N and Gal-8C are required for Gal-8-induced lymphangiogenesis.

Example 20

Gal-8-Induced LEC Sprouting is Dependent on the Activation of AKT and ERK Pathways AKT and ERK1/2 are essential to the process of lymphangiogenesis (Deng, Y., et al. 2013. *J Clin Invest* 123:1202-1215; Zhou, F., et al. 2010. *Am J Pathol* 177:2124-2133). Therefore, both the time- and dose-dependent activation of AKT and ERK1/2 pathways by Gal-8 were tested. In addition, the effect of inhibitors of PI3K and MEK, the upstream signaling molecules of AKT and ERK1/2 pathways, were tested on Gal-8-induced LEC sprouting. To test the effect of Gal-8 on AKT and ERK1/2 activation, primary LECs were serum starved and incubated either with 0.5 μM Gal-8 for 0 to 60 minutes or with 0 to 0.5 μM Gal-8 for 30 minutes. At the end of the incubation period, the whole cell lysates were electrophoresed and the protein blots of the gels were probed with phospho-specific antibodies directed against 5473 of AKT and T202/Y204 of ERK. Gal-8 was observed to have induced phosphorylation of AKT and ERK1/2 in time- and dose-dependent manner (FIG. 3A and FIG. 3B), suggesting that Gal-8 interacts with cell surface proteins to activate AKT and ERK1/2 in LECs.

To determine the role of these pathways on Gal-8-induced lymphangiogenesis, LEC spheroids were stimulated with Gal-8 (0.75 μM) in the presence or absence of PI3K inhibitor (LY294002, 20 μM) and two different MEK inhibitors (U0126, 20 μM; PD0325901, 1 μM). After overnight treatment with Gal-8, accumulated sprout lengths were quantified. All three inhibitors were observed to have markedly inhibited Gal-8-induced LEC sprouting (FIG. 3C-FIG. 3D), indicating that PI3K-AKT and MEK-ERK signaling axes play a crucial role in Gal-8-induced LEC sprouting. VEGF-C-induced sprouting was also inhibited by PI3K and MEK inhibitors (FIG. 3E-FIG. 3F, positive control).

Example 21

Gal-8 Markedly Enhances VEGF-C-Induced Lymphangiogenesis In Vitro and in Vivo

Figure 4A:
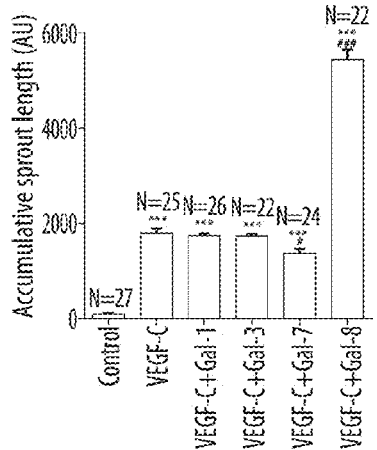
FIG. 4A-FIG. 4E are bar graphs and photomicrographs showing that Gal-8 markedly enhances VEGF-C-induced lymphangiogenesis in vitro and in vivo.
Figure 4B:
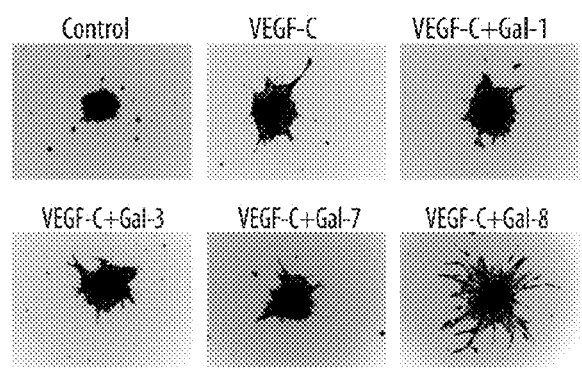
Figure 4C:
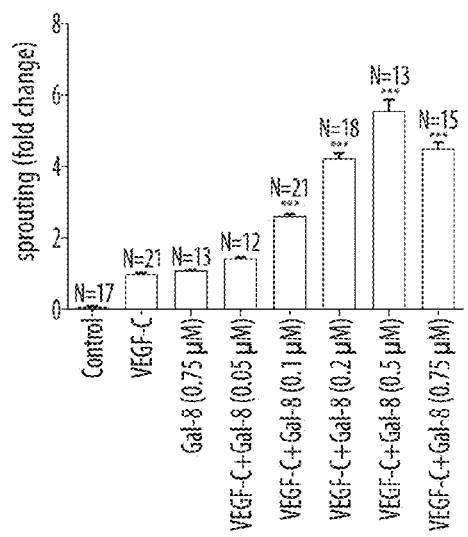

Since galectin-glycan lattices have been shown to increase the magnitude and duration of signaling from the cell surface (Garner, et al. 2008. *Biochem Soc Trans* 36:1472-1477), and VEGF-C/VEGFR-3 signaling plays a prominent role in lymphangiogenesis (Jeltsch, M., et al. 1997. *Science* 276:1423-1425; Karkkainen, M. J., et al. 2004. *Nat Immunol* 5:74-80; Veikkola, T., et al. 2001. *Embo J* 20:1223-1231), the effect of exogenous Gal-8 on VEGF-C-induced LEC sprouting was tested. In this assay, the LEC spheroids were treated with VEGF-C (50 ng/ml) in the presence or absence of 0.75 µM of Gal-8 for 24 hours, and then accumulated sprout lengths were quantified. Gal-8 markedly enhanced VEGF-C-induced LEC sprouting (FIG. 4A-FIG. 4B). In contrast, Gal-1, -3 and -7 did not potentiate VEGF-C-induced LEC sprouting (FIG. 4A-FIG. 4B). Synergistic effect of Gal-8 on VEGF-C-induced LEC sprouting was dose-dependent. In the concentration range of Gal-8 tested (0.05 to 0.75 µM), the extent of VEGF-C-induced sprouting by Gal-8 increased in a dose-dependent manner up to 0.5 µM Gal-8 concentration (FIG. 4C). At concentrations >0.5 µM Gal-8, there was no further increase in the degree of VEGF-C-induced lymphangiogenesis (FIG. 4C). At 0.75 µM of Gal-8, VEGF-C-induced LEC sprouting was 5 times higher than that seen by VEGF-C alone or Gal-8 alone (FIG. 4C), indicating that Gal-8 has a synergistic effect on VEGF-C-induced LEC sprouting. The synergistic effect of Gal-8 on VEGF-C-induced sprouting was almost completely inhibited by TDG, indicating the critical role of the carbohydrate-mediated recognition.

Figure 4D:
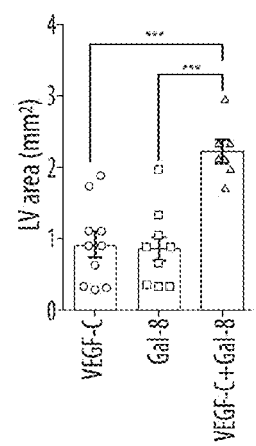
Figure 4E:
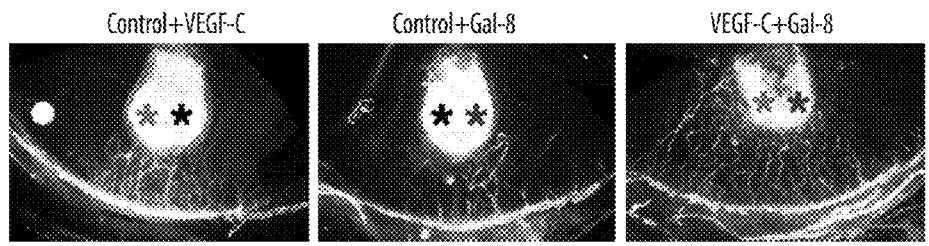

To determine whether Gal-8 also enhances VEGF-C-induced lymphangiogenesis in vivo, two separate pellets (VEGF-C and Gal-8) were implanted in close proximity to one another, in the corneas of Prox1-EGFP reporter mice. One week after surgery, the vessel area was calculated as described in the examples herein. In the in vivo micropocket assays, Gal-8 was observed to have augmented VEGF-C-induced lymphangiogenesis (FIG. 4D-FIG. 4E). Lymphatic vessel growth was 2.2 times higher in the corneas implanted with both VEGFC and Gal-8 pellets compared to the corneas implanted with either VEGF-C pellet or Gal-8 pellet alone.

Next, a series of examples were performed to determine whether VEGF-C-induced lymphangiogenesis is dependent on Gal-8. To determine whether VEGFR-3 is a Gal-8-binding protein, LEC lysates were incubated with Gal-8-conjugated agarose beads in the presence or absence of 0.1 M of lactose (an inhibiting sugar) or sucrose (a non-inhibiting sugar). Bound proteins were examined and were compared to total cell lysates (input) by western blot using anti-VEGFR-3 antibody. Three forms of VEGFR-3 (125 kDa, 175 kDa and 195 kDa) were detected in total cell lysates (FIG. 5A) (Bando, H., et al. 2004. *Int J Cancer* 111:184-191.). The affinity precipitation assay determined that Gal-8 interacted with 125 and 195 kDa VEGFR-3 and not with 175 kDa VEGFR-3 (FIG. 5A), which is considered the intracellular unglycosylated precursor (Bando, H., et al. 2004. *Int J Cancer* 111:184-191.). Binding of VEGFR-3 to Gal-8 were observed to be inhibited by lactose, a competing sugar, and not sucrose, a noncompeting sugar (FIG. 5A), indicating that Gal-8 interacts with VEGFR-3 in a carbohydrate-dependent manner. As described in examples herein, Gal-8 is unique among galectins in exhibiting very high affinity of α2,3-sialyl glycans. Having shown that Gal-8 binds to VEGFR-3 in LECs and that the carbohydrate-binding activity of Gal-8 is required for the synergistic effect of Gal-8 on VEGF-C-induced LEC sprouting, it was of interest to determine whether VEGFR-3 bears 3'-sialylated glycans.

Figure 5A:
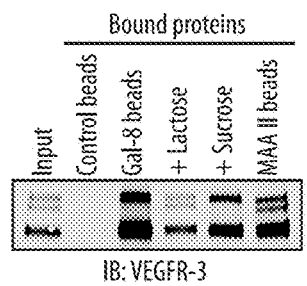
FIG. 5A-FIG. 5G is a set of photographs, photomicrographs and line graphs showing that VEGF-C-induced LEC sprouting is dependent on extracellular Gal-8.
Figure 5B:
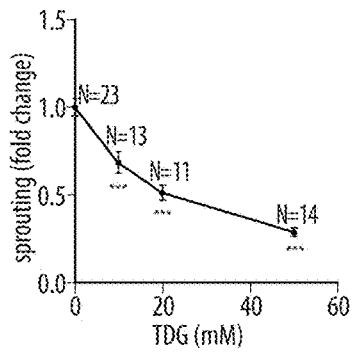
Figure 5C:
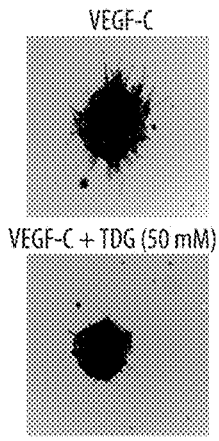
Figure 5D:
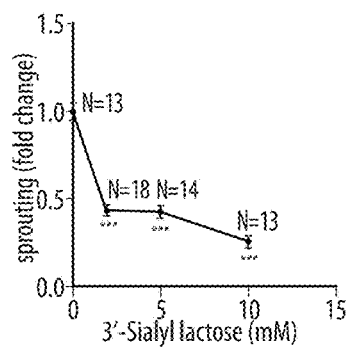
Figure 5E:
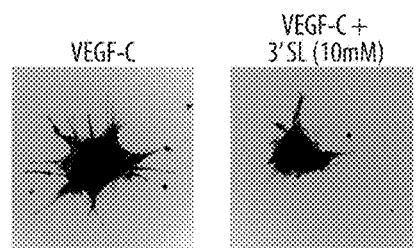
Figure 5F:
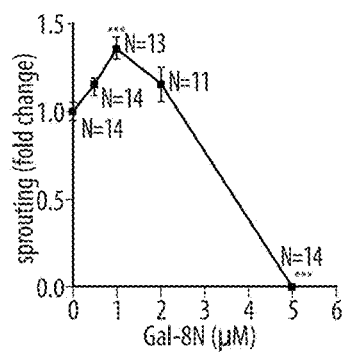
Figure 5G:
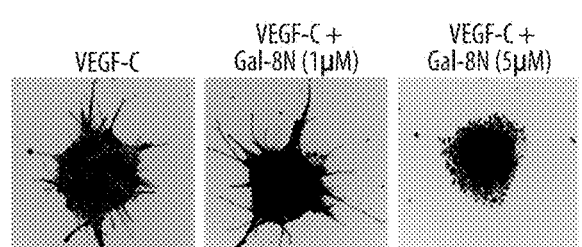
Figure 12:
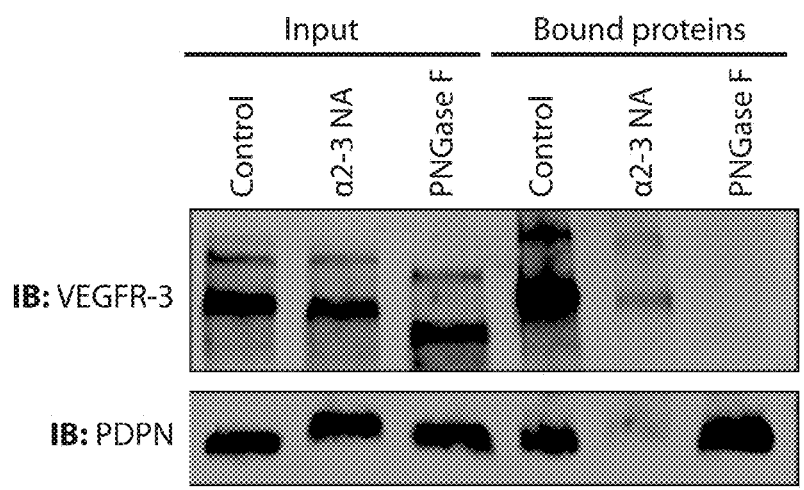
FIG. 12 is a photograph of a western blot showing that Gal-8 interacts with the $\alpha$2,3-sialyl glycans of VEGFR-3 and PDPN. Primary LECs were incubated at 37° C. for 1 hr with buffer only (control), $\alpha$2-3 neuraminidase ($\alpha$2-3NA) that removes $\alpha$2,3-sialyl glycans, or were incubated with peptide-N-glycosidase F (PNGase F) that removes complex glycans from N-linked glycoproteins. After the incubation, the reaction was stopped by adding 400 µL Triton lysis buffer and the reaction mixture was incubated with Gal-8 agarose beads at 4° C. overnight. Unbound proteins were removed and the bound proteins were eluted with 20 µL of 2× Laemmli sample buffer and were examined and compared to input by western blotting. The data show that VEGFR-3 without $\alpha$2,3-sialyl glycans and complex N-glycan did not interact with Gal-8 and PDPN without $\alpha$2,3 sialyl glycans did not interact with Gal-8. The results are representative of three independent examples.
Figure 13A:
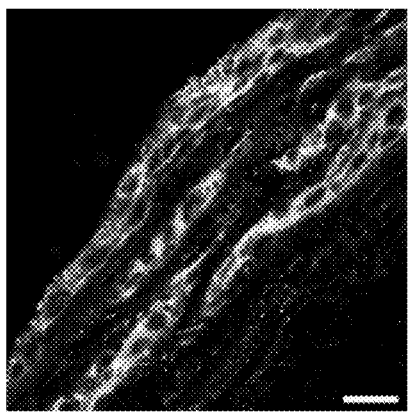
FIG. 13A-FIG. 13D are photomicrographs showing lymphangiogenesis in vascularized mouse cornea. Mouse corneas cauterized with $AgNO_3$ were harvested at day 7. Frozen sections were stained with antibodies to anti-PDPN (FIG. 13B), VEGFR-3 (FIG. 13C) or Gal-8 (FIG. 13D), and were examined by confocal microscopy. Merged images are shown in (FIG. 13A). VEGFR-3, PDPN and Gal-8 were observed to be colocalized in the basal epithelium and lymphatic vessels in the stroma. Scale bar: 25 µm.
Figure 13B:
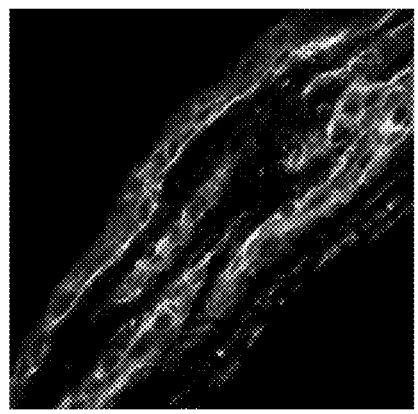
Figure 13C:
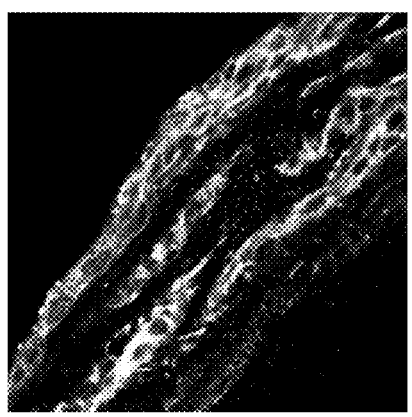
Figure 13D:
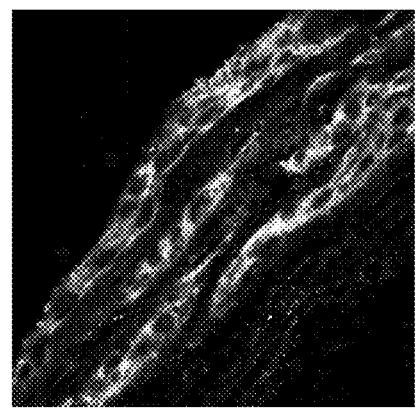

Affinity precipitation examples with a plant lectin, *Maakia Amurensis* II (MAA II), which binds selectively to α2,3-sialic acids, indicated that VEGFR-3 contains 3'-sialylated glycans (FIG. 5A). To further characterize the role of carbohydrate-mediated recognition in VEGF-C-induced lymphangiogenesis, LEC spheroids were stimulated with VEGF-C (50 ng/ml) in the presence or absence of three different galectin inhibitors. The data obtained from these assays indicated that VEGF-C-induced LEC sprouting is inhibited by TDG (a pan inhibitor of galectins, FIG. 5B-FIG. 5C), 3'-sialyl lactose (the high affinity ligand of the N-CRD of Gal-8, FIG. 5D-FIG. 5E), and by Gal-8N (the dominant negative inhibitor of Gal-8, FIG. 5F-FIG. 5G). In addition, removal of α2,3-sialyl glycans were observed to abrogate the interaction of VEGFR-3 and Gal-8, indicating that Gal-8 binds to α2,3-sialyl glycans of VEGFR-3 (FIG. 12). Therefore, the data establishes the critical role of Gal-8-mediated carbohydrate-mediated recognition in VEGF-C-induced lymphangiogenesis.

Example 22

Figure 6A:
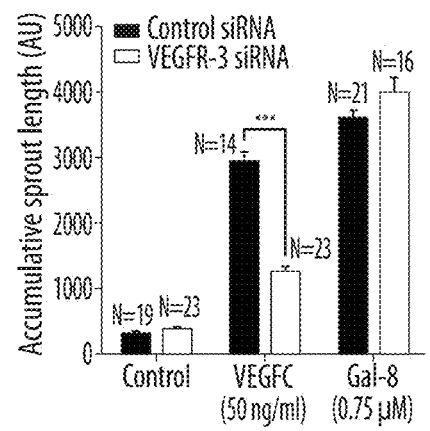
FIG. 6A-FIG. 6G are photographs, photomicrographs and bar graphs showing the role of VEGFR-3 in the molecular mechanism of Gal-8-induced lymphangiogenesis.
Figure 6B:
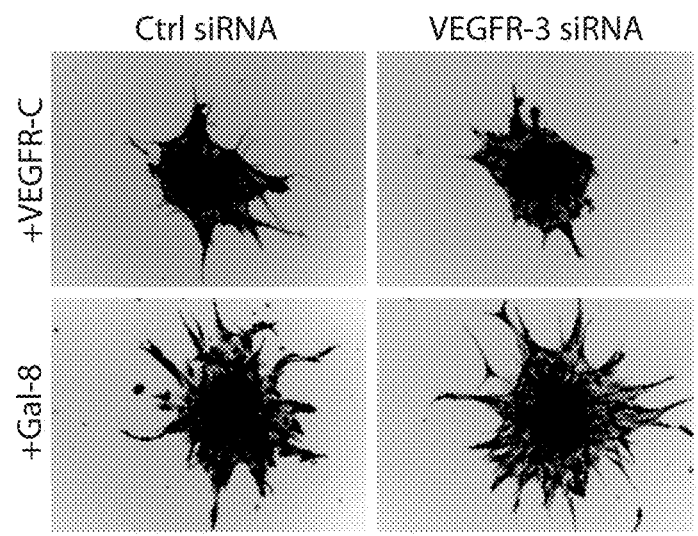

Role of VEGFR-3 in the Molecular Mechanism of Gal-8-Induced Lymphangiogenesis is Limited Data in examples herein established that VEGF-C-induced lymphangiogenesis is dependent on extracellular Gal-8. Accordingly the extent, if any, to which Gal-8-induced lymphangiogenesis is dependent on VEGFR-3/VEGF-C signaling axis was determined. In this assay, spheroids prepared using primary LECs transfected with control or VEGFR-3 siRNA were treated with Gal-8 (0.75 µM) or VEGF-C (50 ng/ml). After 24 hours, accumulated sprout lengths were quantified. The results of western blot analysis showed that the expression of VEGFR-3 was reduced by about 90% in the VEGFR-3 siRNA transfected cells. Knockdown of VEGFR-3 markedly reduced VEGF-C-induced LEC sprouting (FIG. 6A, % inhibition: 57.2). In contrast, knockdown of VEGFR-3 had little effect on Gal-8-induced LEC sprouting (FIG. 6A-FIG. 6B). Since VEGF-C/VEGFR-3 signaling axis is one of the primary pathways involved in lymphangiogenesis, additional strategies were explored involving the use of VEGFR-3-Fc to determine the role of VEGFR-3-mediated signaling pathway in Gal-8-mediated lymphangiogenesis.

In addition, investigations were performed to determine whether VEGF-A/VEGFR-2 pathway, which also promotes lymphangiogenesis, is involved in Gal-8-mediated lymphangiogenesis. LEC spheroids were stimulated with Gal-8 (0.75 µM) in the presence or absence of VEGFR-3-Fc, VEGFR-2-Fc (10 µg/ml), Avastin (bevacizumab) (10 µg/ml) or control IgG (10 µg/ml) for 24 hours and then accumulated sprout lengths were quantified. Positive controls included treatment of LEC spheroids with: VEGF-C in the presence or absence of VEGFR-3-Fc and VEGF-A in the presence or absence of VEGFR-2-Fc and Avastin.

Figure 6C:
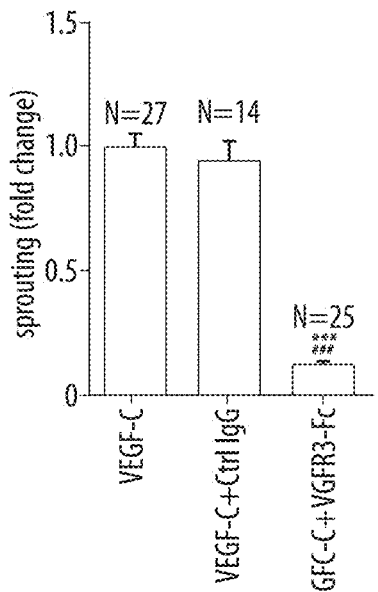
Figure 6D:
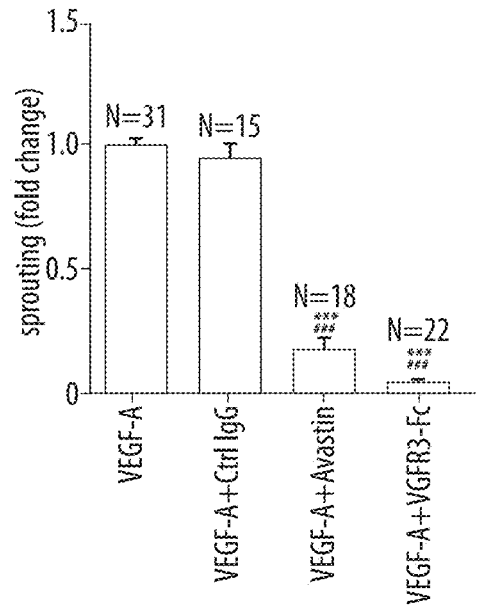
Figure 6E:
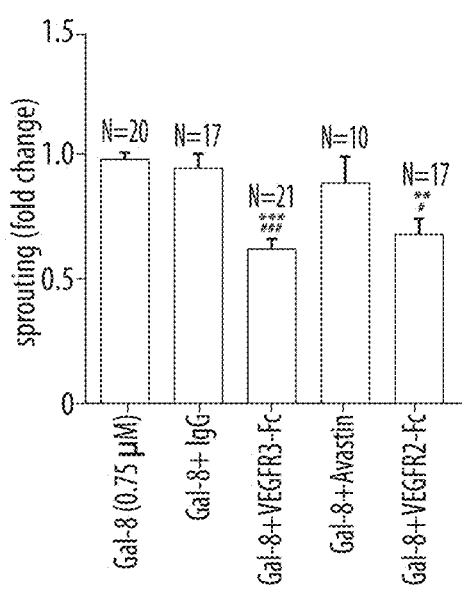

VEGFR-3-Fc were observed to have inhibited VEGF-C-induced LEC sprouting (FIG. 6C); Avastin, an antibody targeted against VEGF-A was observed to have almost completely abolished VEGF-A-induced LEC sprouting (FIG. 6D). In contrast, VEGFR-3-Fc and VEGFR-2-Fc were observed to have only partially inhibited Gal-8-induced LEC sprouting (% inhibition: VEGFR-3-Fc, 37%; VEGFR-2-Fc, 31%). Avastin was observed to have had no effect on Gal-8-induced LEC sprouting (FIG. 6E).

Figure 6F:
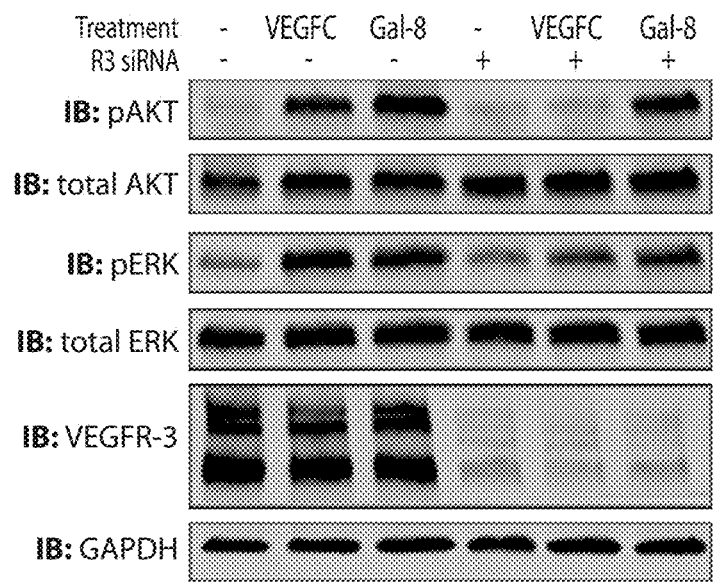
Figure 6G:
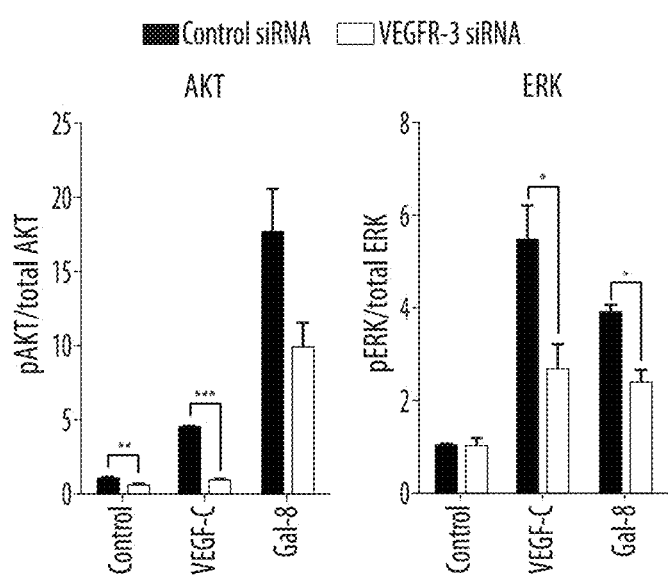

The effect of VEGFR-3 knockdown on Gal-8-induced activation of AKT and ERK was assayed. Primary LECs were transfected with control or VEGFR-3 siRNA; the cells were serum-starved and treated with Gal-8 (0.5 µM) or VEGF-C (50 ng/ml or 3.7 nM, positive control) for 30 minutes. Electrophoresis blots of cell lysates were probed with phospho-specific antibodies directed against 5473 of AKT and T202/Y204 of ERK antibodies. The data show that VEGFR-3 knockdown almost completely abolished VEGF-C-induced activation of AKT (FIG. 6F-FIG. 6G, 92% reduction) and partially reduced Gal-8-induced activation of AKT (FIG. 6F-FIG. 6G, 44% reduction). Gal-8-induced activation of ERK was observed to have been only partially reduced in the VEGFR-3 knockdown cells (FIG. 6F-FIG. 6G, 38% reduction). Together, these data indicate that VEGF-C/VEGFR-3-induced lymphangiogenesis is dependent on Gal-8, that the role of VEGFR-3 in the molecular mechanism of Gal-8-induced lymphangiogenesis is limited, and that additional signaling molecules are involved in Gal-8-induced lymphangiogenesis.

Example 23

Gal-8 and VEGF-C-Induced Lymphangiogenesis is Dependent on PDPN

Figure 7A:
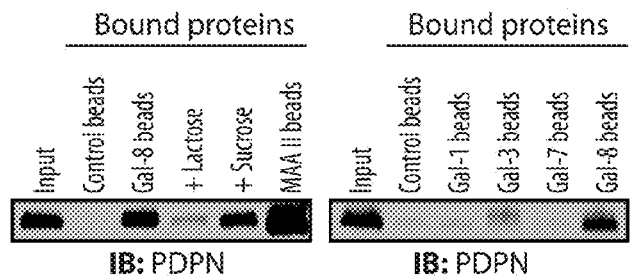
FIG. 7A-FIG. 7F are photographs, photomicrographs and bar graphs showing that Gal-8- and VEGF-C-induced lymphangiogenesis in vitro is dependent on PDPN.

To determine whether PDPN binds to Gal-8 in a carbohydrate-dependent manner, LEC lysates were incubated with Gal-8-conjugated to agarose beads in the presence or absence of 0.1 M of lactose (an inhibiting sugar) or sucrose (a non-inhibiting sugar). Bound proteins were examined with total cell lysates (input) by western blot using an anti-PDPN antibody. To determine specificity of PDPN binding to Gal-8, LEC lysates were also incubated with agarose beads conjugated to Gal-1, Gal-3 and Gal-7. Within the whole cell lysate, an anti-PDPN-reactive 43-kDa component was detected (FIG. 7A). The affinity precipitation assay indicated that PDPN interacted with Gal-8 and not Gal-1, -3 or -7 (FIG. 7A). Binding of PDPN to Gal-8 was observed to be inhibited by lactose, a competing sugar, and not by sucrose, a noncompeting sugar (FIG. 7A), indicating that Gal-8 interacts with PDPN in a carbohydrate-dependent manner. Affinity precipitation assays conducted using MAA II which binds selectively to α2,3-sialic acids indicated that PDPN contains 3'-sialylated glycans (FIG. 7A), the high-affinity ligands of the N-CRD of Gal-8. In addition, removal of α2,3-sialyl glycans were observed to have abrogated the interaction of PDPN and Gal-8, indicating that Gal-8 binds to α2,3-sialyl glycans on the O-glycans of PDPN (FIG. 12).

Figure 7B:
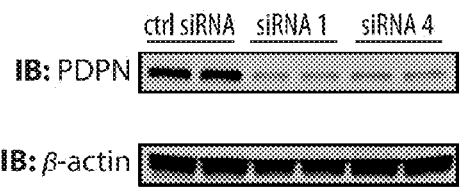
Figure 7C:
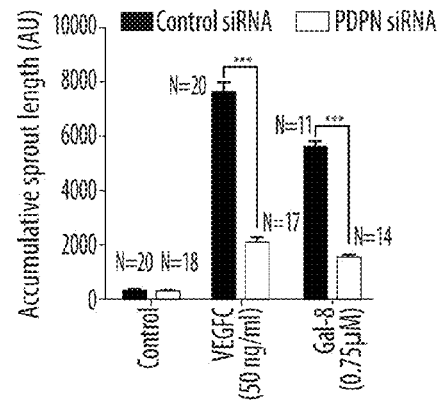
Figure 7D:
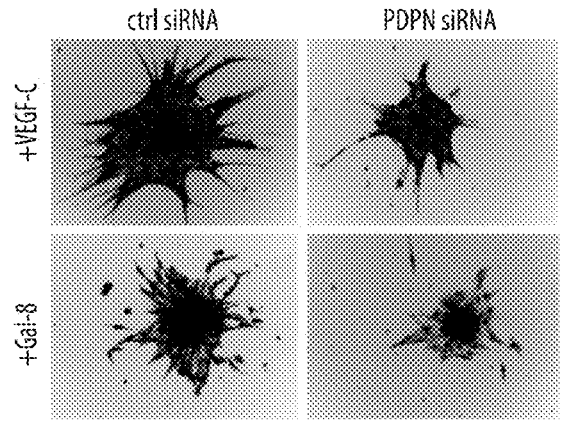
Figure 7E:
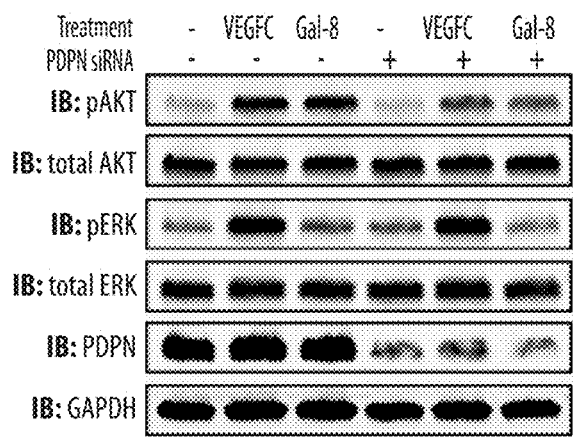
Figure 7F:
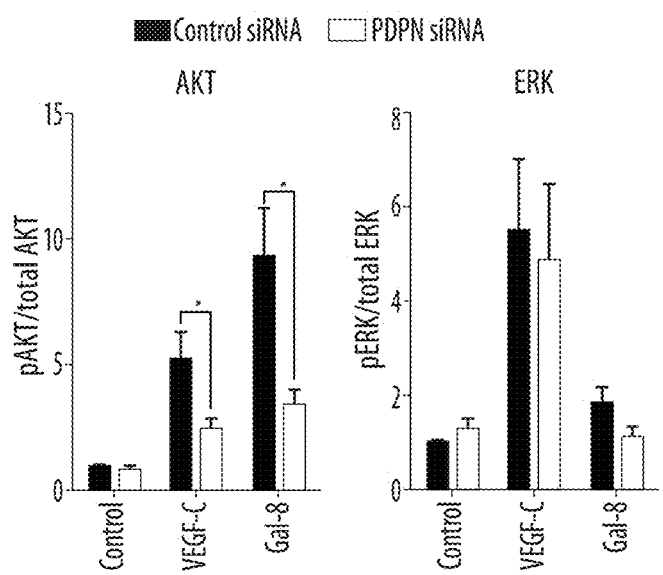

To determine whether PDPN plays a role in Gal-8- and/or VEGF-C-induced lymphangiogenesis, spheroids prepared using primary LECs transfected with control or pooled PDPN siRNA were treated with Gal-8 (0.75 µM) or VEGF-C (50 ng/ml). After 24 hr, accumulated sprout lengths were quantified. The expression of PDPN was observed to have been reduced by about 78% in the siRNA transfected LECs (FIG. 7B). PDPN knockdown was observed to have markedly inhibited Gal-8-induced LEC sprouting (FIG. 7C-FIG. 7D) and to have substantially reduced VEGF-C-induced LEC sprouting (FIG. 7C-FIG. 7D).

To determine whether PDPN knockdown inhibits Gal-8- and/or VEGFC-induced activation of AKT and ERK pathways, primary LECs transfected with control or PDPN siRNA were serum-starved and treated with Gal-8 (0.5 µM) or VEGF-C for 30 min. Electrophoresis blots of cell lysates were probed with phospho-specific antibodies directed against 5473 of AKT and T202/Y204 of ERK. PDPN knockdown was observed to have substantially reduced each of Gal-8- and VEGF-C-induced activation of AKT and not ERK (FIG. 7E-FIG. 7F), indicating that PDPN modulates Gal-8- and PDPN-induced lymphangiogenesis largely by activation of AKT pathway.

Figure 8A:
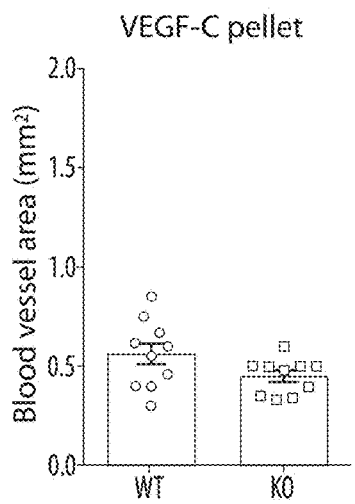
FIG. 8A-FIG. 8H are photomicrographs and graphs showing that VEGF-C- and Gal-8-induced lymphangiogenesis in vivo is dependent on PDPN.
Figure 8B:
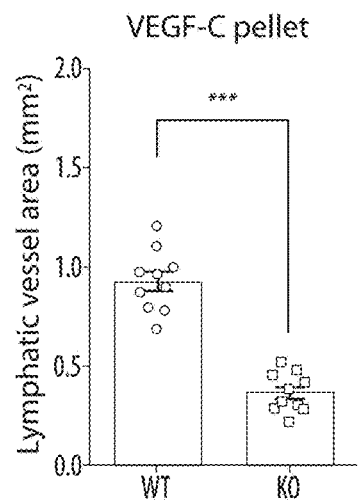
Figure 8C:
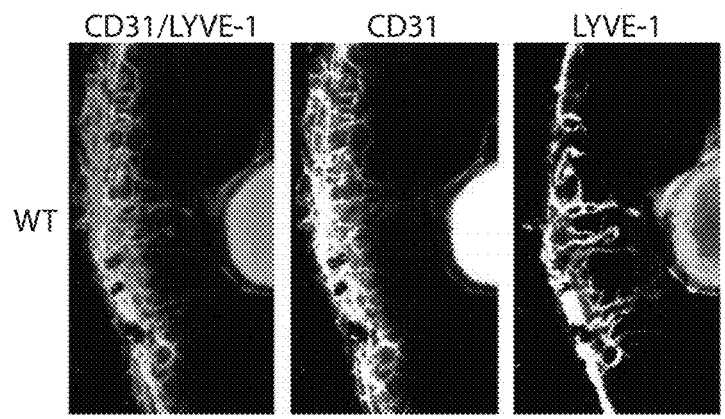
Figure 8D:
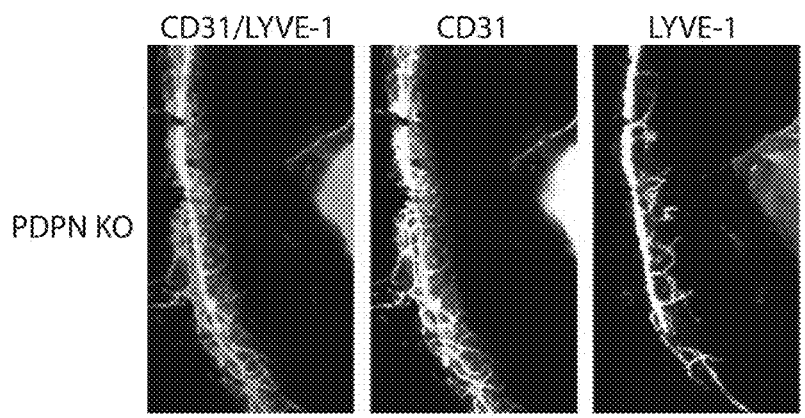
Figure 8E:
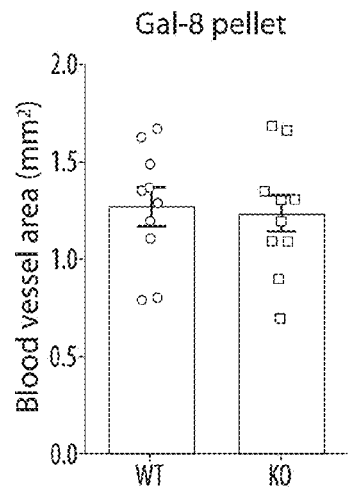
Figure 8F:
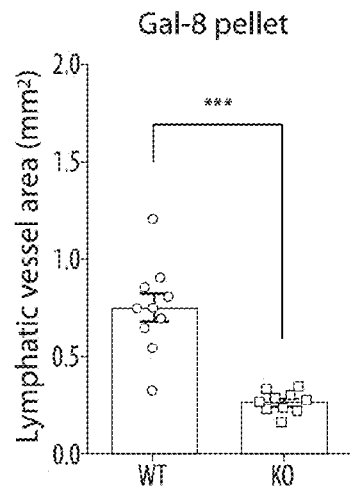
Figure 8G:
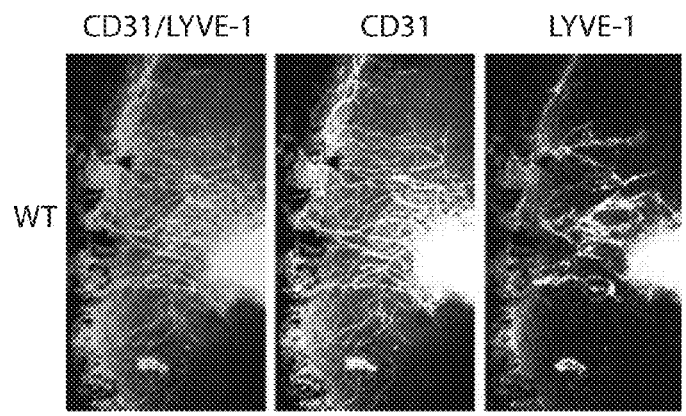
Figure 8H:
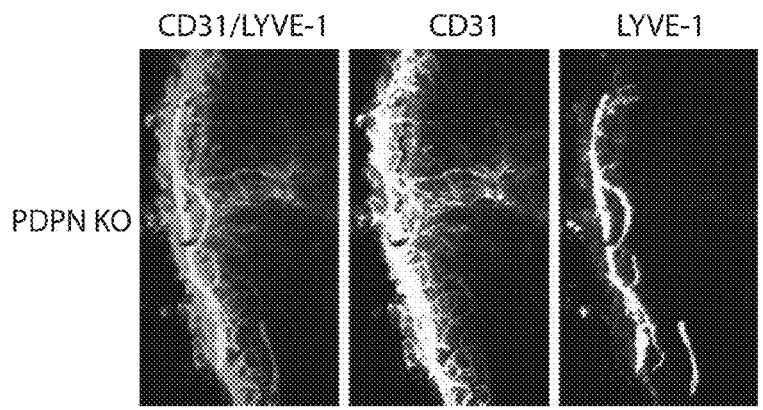

To further determine whether PDPN plays a role in Gal-8- and/or VEGF-C-induced lymphangiogenesis in vivo, mice with tamoxifen-inducible global deletion of PDPN (Pdpn$^{f/}$ $_f$;CagCre) (Herzog, B. H., et al. 2013. Nature 502:105-109) were used to perform the corneal micropocket assays. Tamoxifen administration (1 mg/week) resulted in complete loss of PDPN in the corneal limbus determined by immunohistochemistry staining. VEGF-C (160 ng) pellets were observed to have markedly induced both hemangiogenesis and lymphangiogenesis in wild type (WT) mice. The extent of VEGF-C-induced hemangiogenesis was similar in both WT and PDPN-deficient mice. In contrast, VEGF-C-induced lymphangiogenesis was observed to have significantly reduced in the PDPN-deficient mice (mean lymphatic vessel areas: 1.35 mm$^2$ in WT mice; 0.67 mm$^2$ in PDPN KO mice) (FIG. 8A-FIG. 8D). Likewise, Gal-8-induced lymphangiogenesis, and not hemangiogenesis, was observed to have reduced in PDPN-deficient mice (mean lymphatic vessel areas: 0.78 mm$^2$ in WT mice; 0.28 mm$^2$ in PDPN KO mice) (FIG. 8E-FIG. 8G). Together, the data indicate that PDPN is a key player, in Gal-8-induced lymphangiogenesis and also in VEGF-C-induced lymphangiogenesis.

Example 24

Gal-8 Clusters PDPN and VEGFR-3 on LEC Plasma Membrane

Figure 9A:
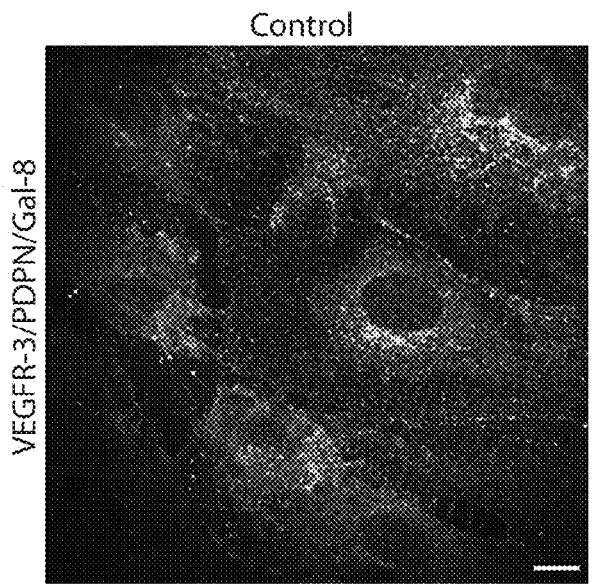
FIG. 9A-FIG. 9J are photomicrographs and line graphs showing that Gal-8 causes clustering and retention of PDPN and VEGFR-3 on LEC membranes. LECs were treated with or without Gal-8 for 15 min, fixed, stained with antibodies to anti-VEGFR-3 (FIG. 9B and FIG. 9G), PDPN (FIG. 9C and FIG. 9H) and Gal-8 (FIG. 9D and FIG. 9I), and were examined by confocal microscopy.
Figure 9B:
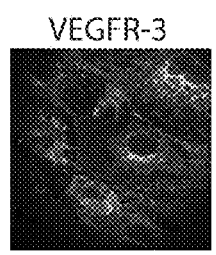
Figure 9C:
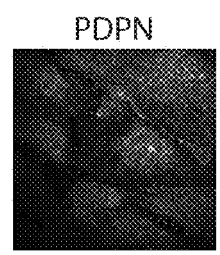
Figure 9D:
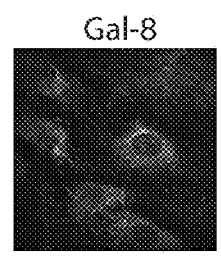
Figure 9E:
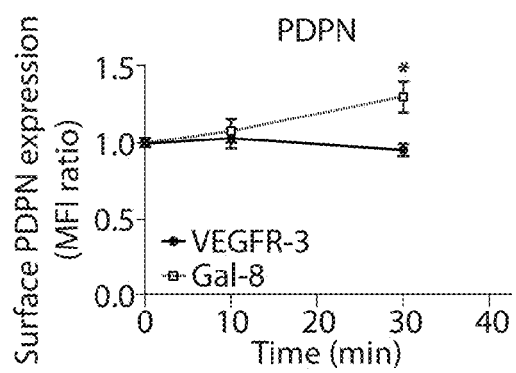
Figure 9F:
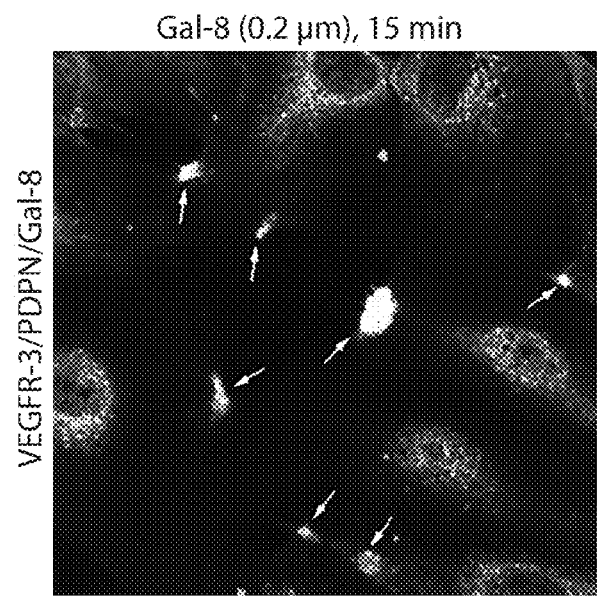
Figure 9G:
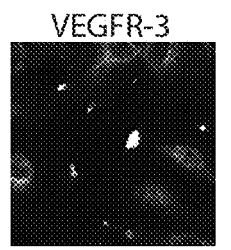
Figure 9H:
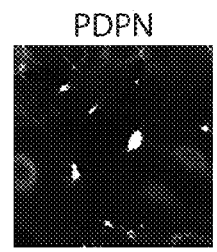
Figure 9I:
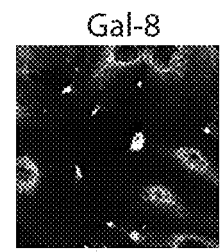
Figure 9J:
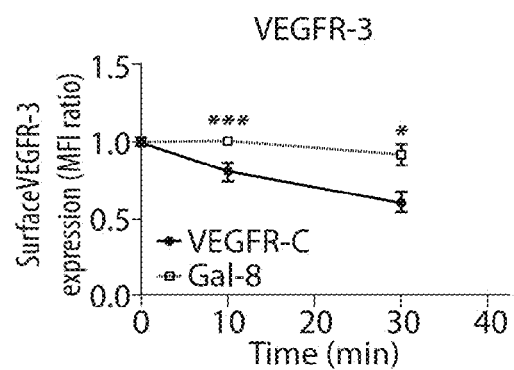

Since galectin-glycan lattices segregate the cell surface receptors into discrete domains to initiate cell signaling (Lajoie, P., et al. 2009. J Cell Biol 185:381-385), assays were performed to determine whether Gal-8 clusters PDPN and VEGFR-3 on LEC plasma membrane. LECs were treated with Gal-8 for 15 minutes, fixed, stained with anti-PDPN, VEGFR-3 and Gal-8 antibodies, and examined by confocal microscopy. In control cells, which were incubated with buffer only, both PDPN and VEGFR-3 were homogenously distributed all over the LEC and in cell borders; endogenous Gal-8 was mainly distributed in cytosol (FIG. 9A-FIG. 9D). Exogenous Gal-8 was added to determine whether Gal-8 changes distribution of PDPN and/or VEGFR-3 in LECs. Addition of Gal-8 caused dramatic redistribution and clustering of PDPN and VEGFR-3 on LEC plasma membrane (FIG. 9F-FIG. 9I). PDPN clusters were observed to be larger than VEGFR-3 clusters. In some areas, VEGFR-3, PDPN and Gal-8 were observed to have colocalized (FIG. 9F-FIG. 9I, arrow). Moreover, consistent with the notion of galectin-glycan lattice formation, Gal-8 treatment were observed to have increased cell-surface residency of VEGFR-3 and PDPN compared to VEGF-C treatment in primary LECs (FIG. 9E-FIG. 9J). After 30 min post-treatment, cell surface expression of PDPN was observed to have increased by about 30% in Gal-8-treated cells. In contrast, the cell surface expression of PDPN was observed to have decreased by about 5% in VEGF-C-treated cells (FIG. 9E). Although the cell surface expression of VEGFR-3 decreased in both Gal-8- and VEGF-C-treated cells, the extent of decrease was observed to be less in Gal-8-treated cells (about 10% decrease) compared to the VEGF-C-treated cells (about 40% decrease) (FIG. 9J). These findings in conjunction with data presented in FIG. 3 showing that Gal-8 treatment activates AKT and ERK pathway indicate that Gal-8 binds to specific glycan ligands of cell-surface PDPN and VEGFR-3 and segregates them into discrete signaling complexes to promote lymphangiogenesis.

Example 25

Figure 10A:
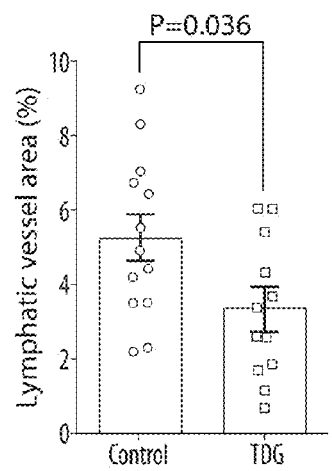
FIG. 10A-FIG. 10J are photomicrographs and graphs showing that galectin inhibitors resulted in significantly decreased inflammatory lymphangiogenesis in vivo (FIG. 10A and FIG. 10B). Silver nitrate cautery was introduced in the center of the corneas of the Prox1-EGFP reporter mice (FIG. 10E and FIG. 10F). The animals were treated with TDG (200 mM, a pan inhibitor of galectins.
Figure 10B:
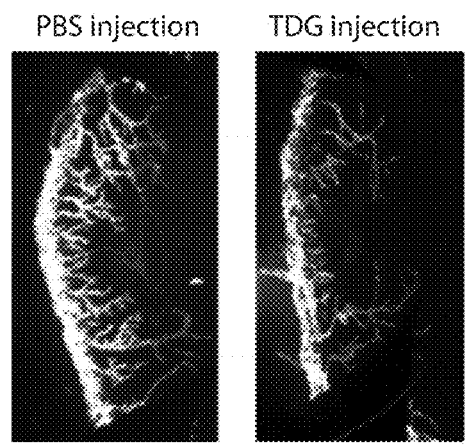
Figure 10C:
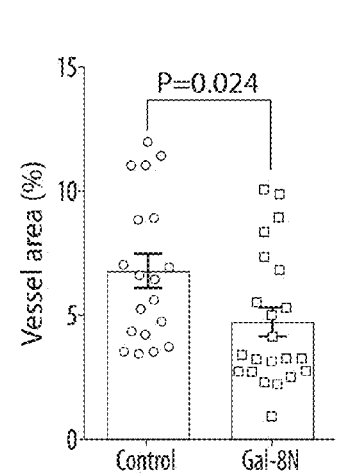
Figure 10D:
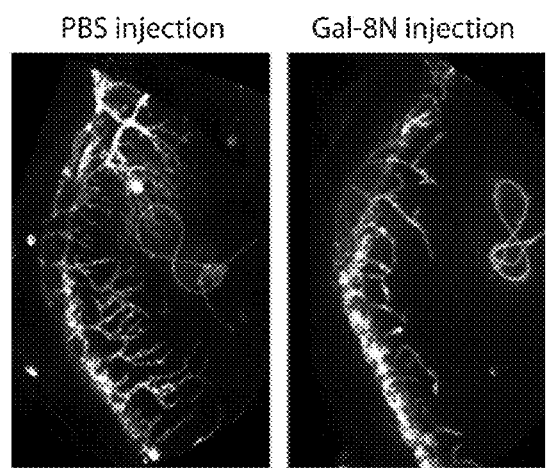
Figure 10E:
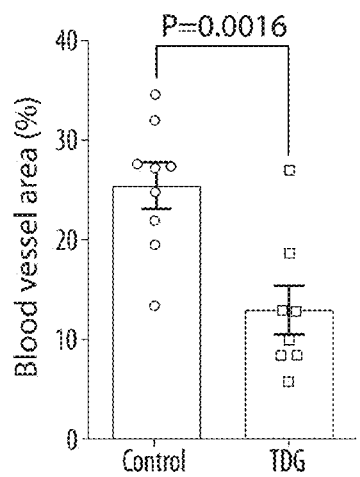
Figure 10F:
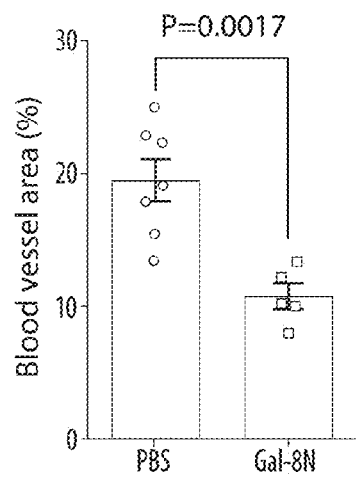
Figure 10G:
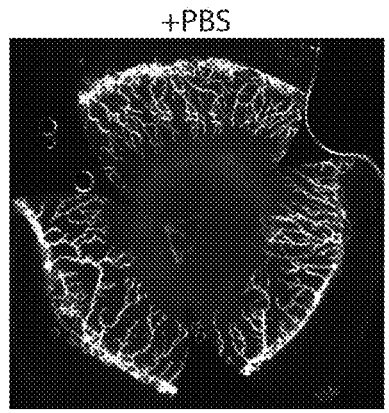
Figure 10H:
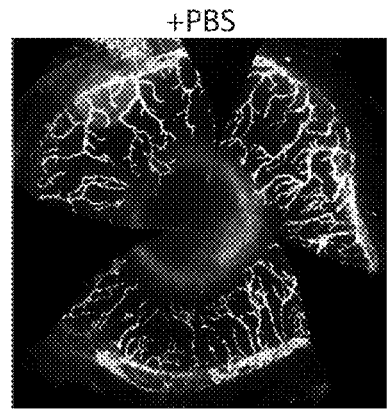
Figure 10I:
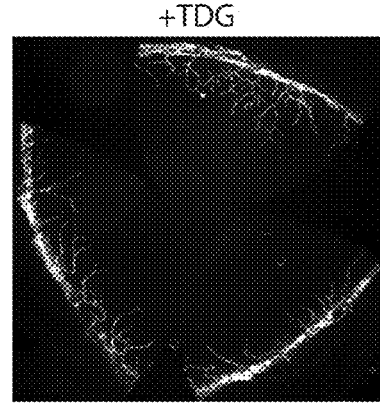
Figure 10J:
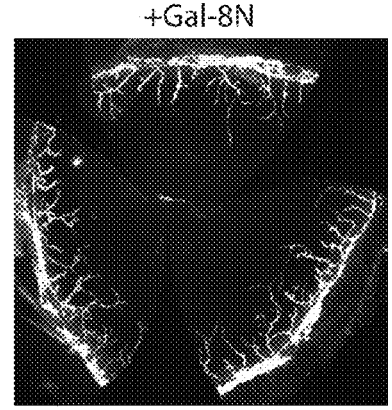

Galectin Inhibitors Significantly Decrease Inflammatory Lymphangiogenesis In Vivo There is much interest in finding ways to inhibit prolymphangiogenic factors as means of suppressing cancer metastasis, transplant rejection and chronic inflammation. To determine whether galectins can be targeted to control lymphangiogenesis, a well-established in vivo model of lymphangiogenesis was used. In this model, sutures are placed approximately 2 mm above the limbic vessel in the mouse corneas. The inflammatory insult perpetuated by suture placement induces the growth of blood and lymphatic vessels in normally clear cornea. After suture placement in the corneas of Prox1-EGFP reporter mice to induce inflammation, the animals were treated with TDG (200 mM, a pan inhibitor of galectins, i.e., a general inhibitor of several galectins) or with Gal-8N (15 µg, the dominant negative inhibitor of Gal-8) by local subconjunctival injections on days 0, 2, 4 and 6 post-surgery. At the end of the treatment period, lymphatic vessel areas were quantified. Treatment with both TDG (FIG. 10A-FIG. 10B) or with Gal-8N (FIG. 10C-FIG. 10D) was observed to have significantly suppressed suture-induced corneal lymphangiogenesis. These data indicate a novel mechanism for the modulation of pathological lymphangiogenesis by targeting Gal-8.

Example 26

Figure 14A:
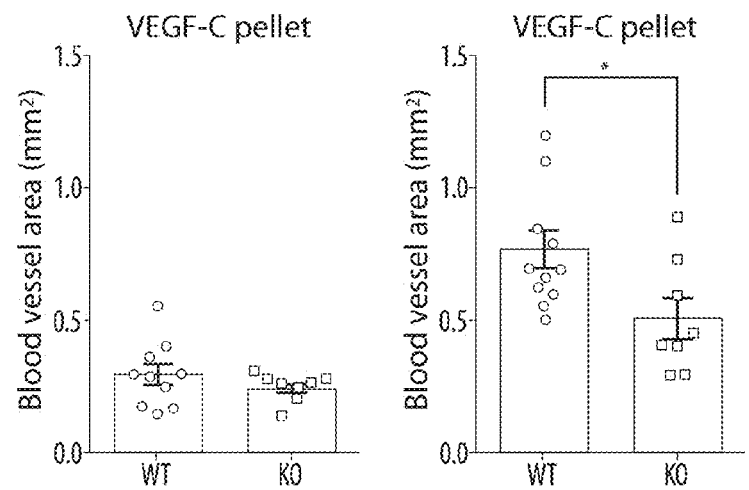
FIG. 14A-FIG. 14F are bar graphs and photomicrographs showing that inflammatory lymphangiogenesis induced by VEGF-C or suture is reduced in galectin-8 knockout (KO) mice.
Figure 14B:
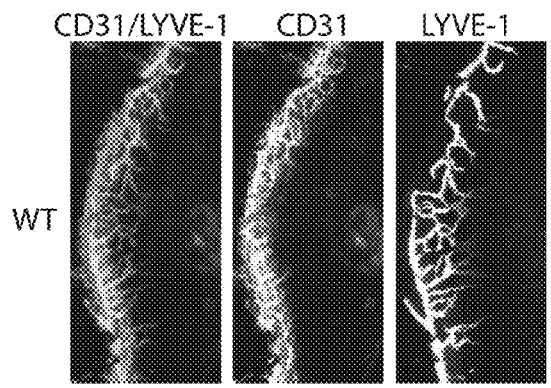
Figure 14C:
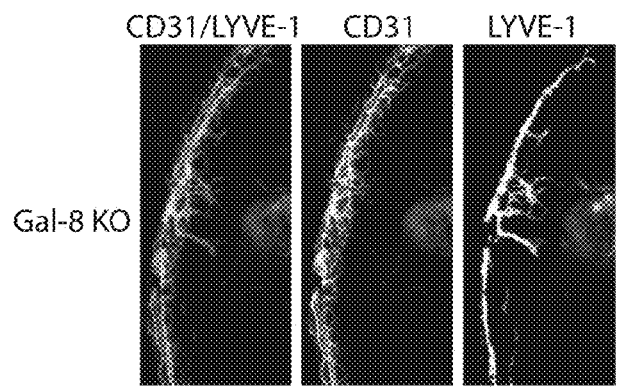
Figure 14D:
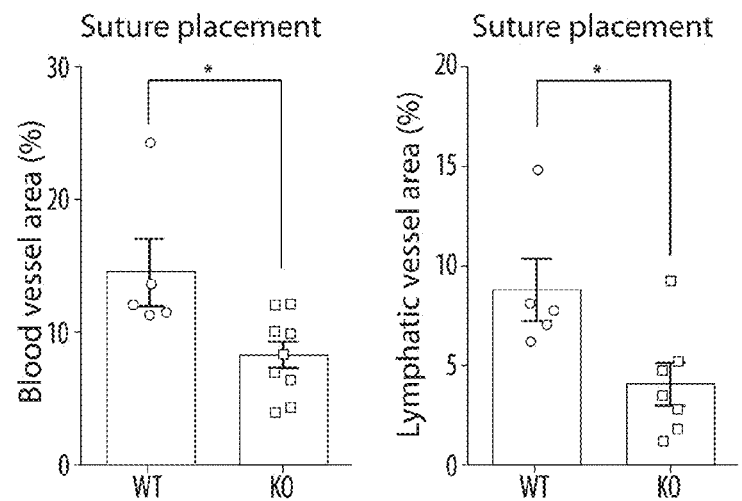
Figure 14E:
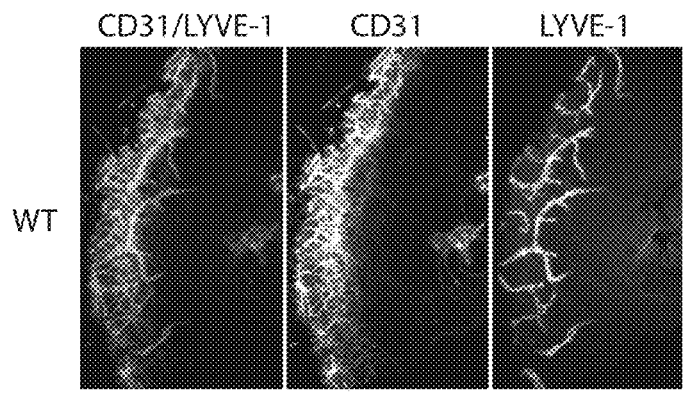
Figure 14F:
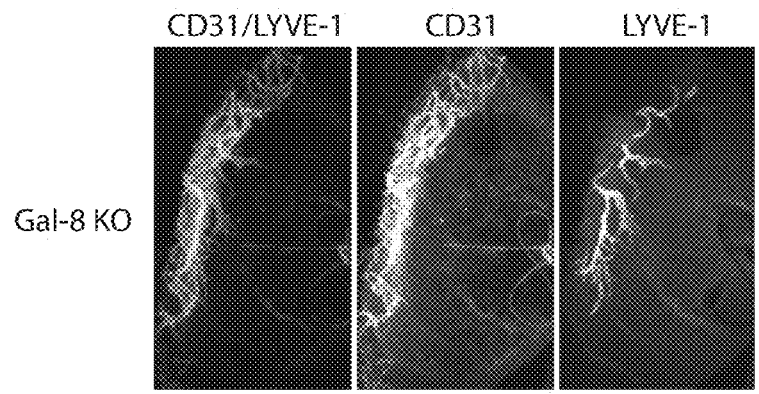

VEGF-C-Induced and Suture-Induced Inflammatory Lymphangiogenesis is Reduced in Galectin-8 Knockout Mice To test the role of galectin-8 in postnatal lymphangiogenesis in vivo, mouse corneal micropocket assays and induced inflammatory lymphangiogenesis in wild type (WT) and galectin-8 knockout (KO) mice were performed. For micropocket assays, pellets containing 160 ng of VEGF-C were implanted into mouse corneas, and one week after surgery, the vessel area representing the extent of lymphangiogenesis was calculated. In WT mice, VEGF-C was observed to induce robust growth of lymphatic vessels (FIG. 14A and FIG. 14B). The extent of vessel formation mediated by VEGF-C was observed to have been significantly reduced in galectin-8 KO mice compared to WT control mice (FIG. 14A, FIG. 14C). Similarly, the extent of inflammatory lymphangiogenesis induced by suture placement (FIG. 14D-FIG. 14F) and AgNO₃ cautery (FIG. 20A-FIG. 20D) in the cornea was observed to have been reduced in galectin-8 KO mice in comparison to WT mice.

Example 27

Galectin-8 and VEGF-C-Induced Lymphangiogenesis is Dependent on PDPN

Figure 21A:
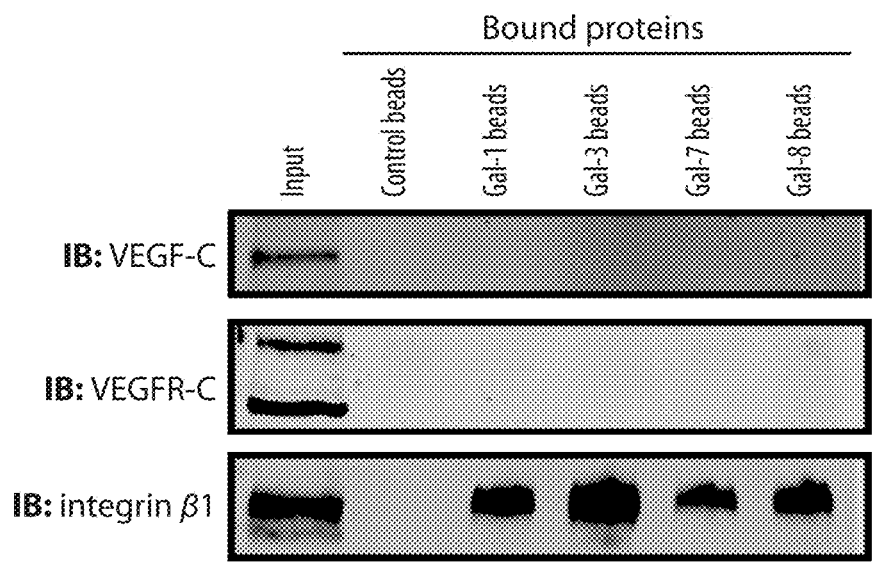
FIG. 21A-FIG. 21B are photographs of western blots showing that galectin-8 interacts with VEGFR-3 and does not interact with VEGF-C.
Figure 21B:
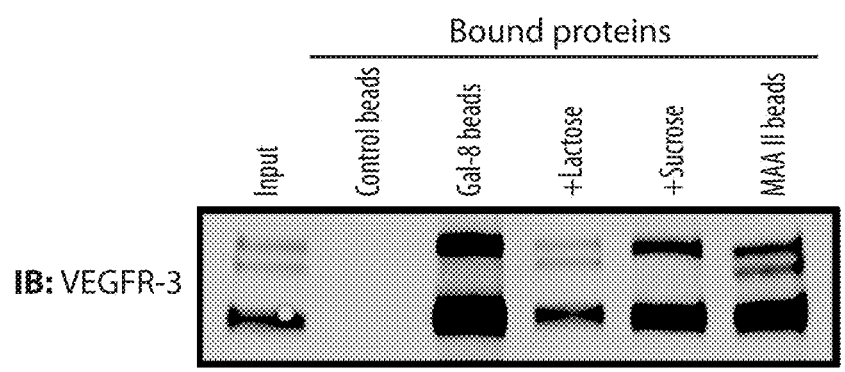
Figure 22A:
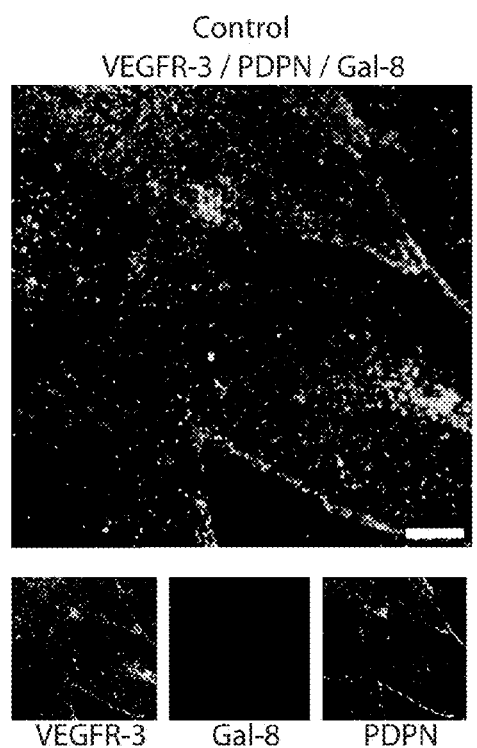
FIG. 22A-FIG. 22B are photomicrographs showing that galectin-8 results in clusters of VEGFR-3 and PDPN on cell surfaces. LECs were treated with or without galectin-8 for 15 min, fixed without permeabilization, stained with antibodies to anti-VEGFR-3 (green), PDPN (blue) and galectin-8 (red), and were examined by confocal microscopy. Merged images are shown in the top panels of each of FIG. 22A and FIG. 22B. In control LECs, no colocalization of VEGFR-3, galectin-8 and PDPN was observed.
Figure 22B:
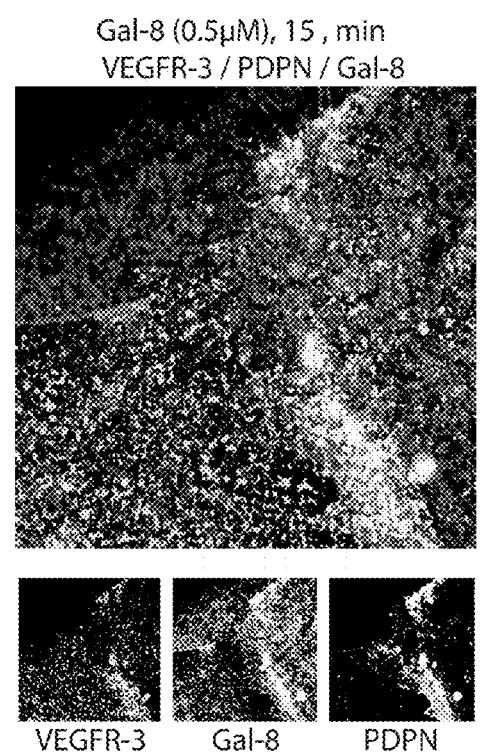
Figure 23A:
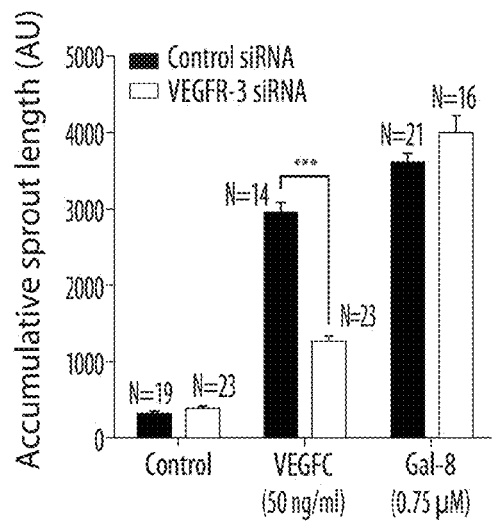
FIG. 23A-FIG. 23E are bar graphs and photomicrographs showing that VEGFR-3 and Neuropilin-2 (Nrp2) knockdown has little effect on galectin-8-induced lymphangiogenesis.
Figure 23B:
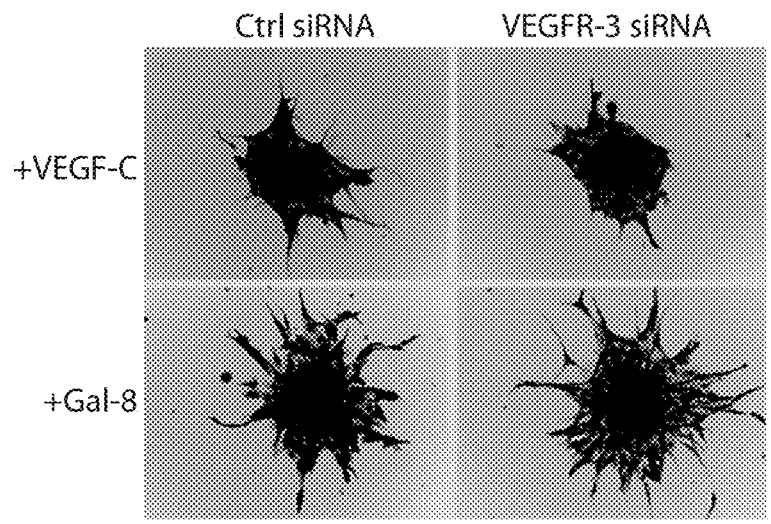
Figure 23C:
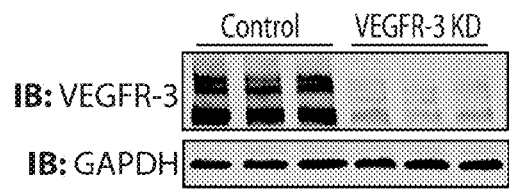
Figure 23D:
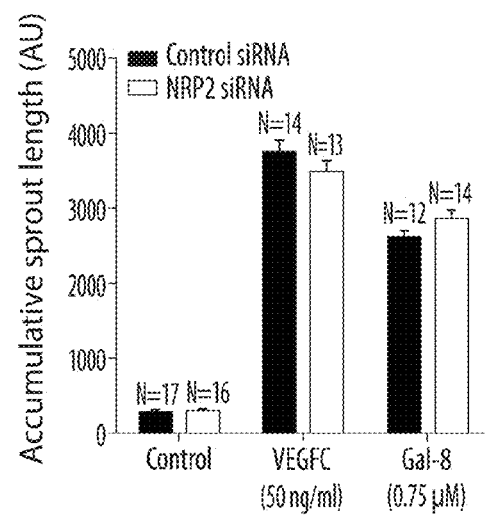
Figure 23E:
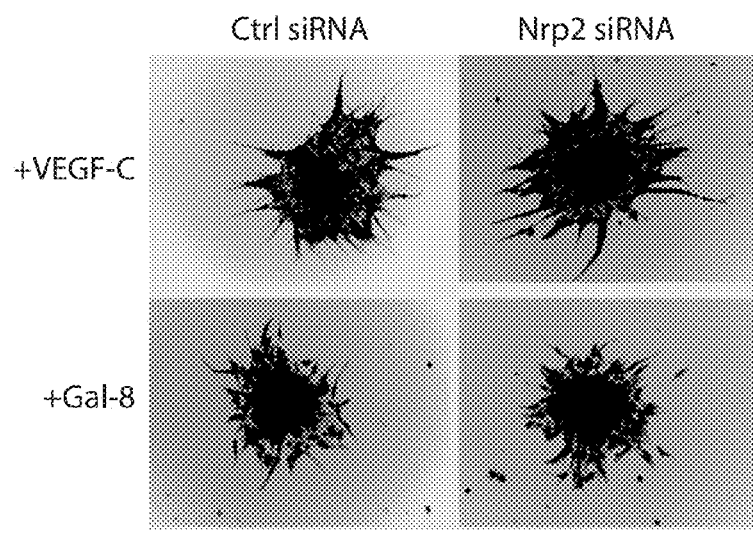
Figure 23F:
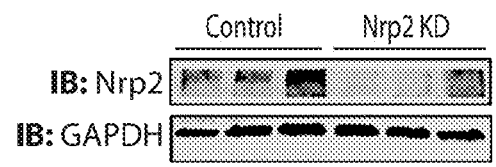

It has been reported that the galectin-glycan lattices increase receptor residency time by inhibiting endocytosis of glycoprotein receptors from the cell surface which increases the magnitude or duration of signaling from the cell surface (Garner, O. B. et al., 2008. *Biochemical Society transactions* 36, 1472-1477; Rabinovich, G. A., et al., 2007 *Current opinion in structural biology* 17, 513-520). Therefore, in an effort to characterize the mechanism by which galectin-8 modulates VEGF-C-induced lymphangiogenesis, an assay was conducted to determine whether the lectin modulates VEGFR-3, the predominant VEGF-C receptor. It was observed that VEGFR-3 was a galectin-8 binding protein and VEGF-C was not a galectin-8 binding protein (FIG. 21A-FIG. 21B). Further, galectin-8 was observed to cluster VEGFR-3 on cell surfaces (FIG. 22A-FIG. 22B). However, surprisingly, knockdown of VEGFR-3 had little effect on galectin-8-induced LEC sprouting (FIG. 23A and FIG. 23B) which indicates that molecules in addition to VEGFR-3 are involved in galectin-8-induced lymphangiogenesis. Therefore, whether galectin-8-mediated lymphangiogenesis involves other receptors for VEGF-C was explored. It is known that VEGFR-2, which also binds VEGF-C, is not involved in VEGF-C-induced sprouting (Joukov, V. et al. 1997. *EMBO journal* 16, 3898-3911; Wirzenius, M. et al. 2007 *Journal of experimental medicine* 204, 1431-1440). The siRNA knockdown and/or antibody blocking data in examples herein indicated that several other known receptors of VEGF-C including neuropilin-2 and integrin α9β161-64 are not possible targets of galectin-8 (FIG. 23D, FIG. 23E and FIG. 15A-FIG. 15D). PDPN which is expressed by LECs and not expressed by blood ECs, is thought to play a role in the process of lymphangiogenesis (Navarro, A., et al. 2008. *Am J Physiol Lung Cell Mol Physiol* 295:L543-551; Navarro, A., et al. 2011. *Am J Physiol Lung Cell Mol Physiol* 300:L32-42). However, the role of Gal-8 in the modulation of PDPN has not been investigated and virtually nothing is known about the role of PDPN in VEGF-C-induced lymphangiogenesis. Therefore, assays were performed to determine whether: (i) PDPN binds galectin-8 in a carbohydrate-dependent manner, (ii) PDPN knockdown inhibits galectin-8- and/or VEGFC-induced LEC sprouting and activation of AKT and ERK pathways, and (iii) galectin-8- or VEGF-C-induced lymphangiogenesis is attenuated in mice with inducible deletion of PDPN (Pdpnf/f;CagCre).

Figure 24:
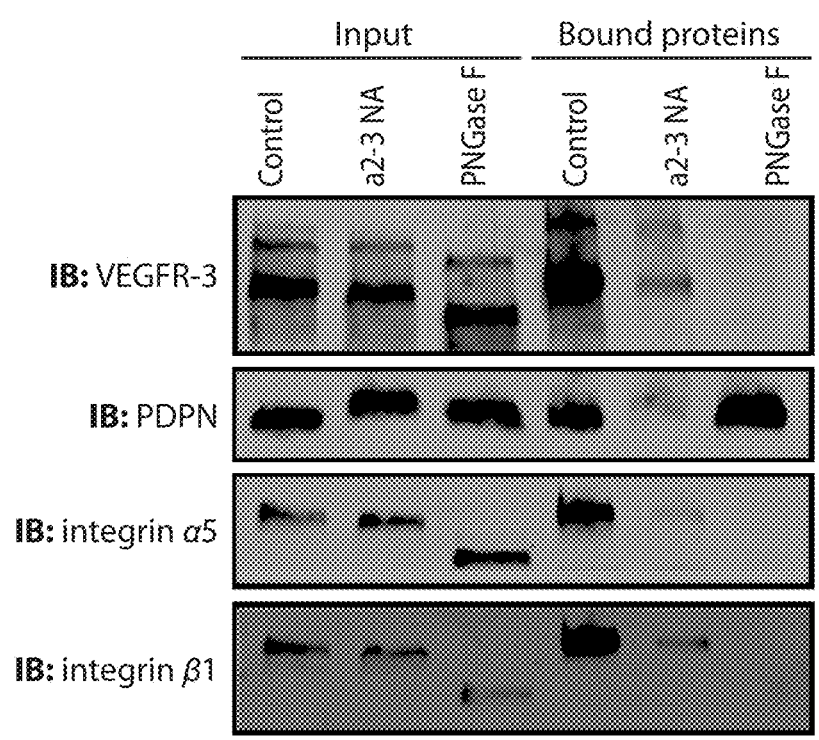
FIG. 24 is a set of photographs of western blots showing that galectin-8 interacts with the α2,3-sialyl glycans of PDPN. Primary LECs were incubated at 37° C. for 1 hour with buffer only (control), α2-3 neuraminidase (α2-3NA) that removes α2,3-sialyl glycans, or with peptide-N-glycosidase F (PNGase F) that removes complex glycans from N-linked glycoproteins. Post incubation, reaction was stopped by adding 400 μl Triton lysis buffer and the reaction mixture was incubated with galectin-8 agarose beads at 4° C. overnight. Unbound proteins were removed and the bound proteins were eluted with 20 μL of 2x Laemmli sample buffer and examined by western blotting with control input. It was observed that VEGFR-3 and integrins failed to interact with galectin-8 without complex N-glycan. Further, it was observed that PDPN did not interact with galectin-8 in the absence of the α2,3 sialyl glycans.

As determined by affinity precipitation assays, PDPN was observed to have interacted with galectin-8, and not to have interacted with galectin-1, -3 or -7, and the binding of PDPN to galectin-8 was carbohydrate-dependent (FIG. 7A). Additionally, pulldown methods with agarose beads conjugated with the plant lectin MAAII (specificity: α2,3-sialylated glycans) indicated that PDPN contains α2,3-sialylated glycans (FIG. 7A). Removal of α2,3-sialylated glycans by treatment with α2-3 neuraminidase abrogated the interaction of PDPN and galectin-8, indicating that galectin-8 binds α2,3-sialylated glycans on the O-glycans of PDPN (FIG. 24). To determine whether PDPN plays a role in Gal-8- and/or VEGF-C-induced lymphangiogenesis, spheroids prepared using primary LECs transfected with control or pooled PDPN siRNA were treated with galectin-8 or VEGF-C. The expression of PDPN was reduced by 82% in the siRNA transfected LECs (FIG. 7B). PDPN knockdown markedly inhibited galectin-8-induced LEC sprouting and substantially reduced VEGF-C-induced LEC sprouting (FIG. 7C, FIG. 7D). Additionally, PDPN knockdown in LECs substantially reduced galectin-8- and VEGF-C-induced activation of AKT and not ERK (FIG. 7E, FIG. 7F), indicating that PDPN modulates galectin-8- and VEGF-C-induced lymphangiogenesis largely by activation of the AKT pathway.

To determine whether PDPN plays a role in galectin-8- and/or VEGF-C-induced lymphangiogenesis in vivo, mice with tamoxifen-inducible global deletion of PDPN (Pdpnf/f;CagCre)65 were used to perform the corneal micropocket assays. VEGF-C pellets were observed to markedly induce both hemangiogenesis and lymphangiogenesis in WT mice. The extent of VEGF-C-induced hemangiogenesis was observed to be similar in both WT and PDPN-deficient mice (FIG. 8A). In contrast, VEGF-C-induced lymphangiogenesis was significantly reduced in the PDPN-deficient mice (FIG. 8 A, FIG. 8C). Likewise, galectin-8-induced lymphangiogenesis, and not hemangiogenesis, was reduced in PDPN-deficient mice (FIG. 8D-FIG. 8F). These data indicate that PDPN is a key player in galectin-8-induced lymphangiogenesis and in VEGF-C-induced lymphangiogenesis.

Example 28

Integrins Play a Key Role in Galectin-8-PDPN-Mediated Lymphangiogenic Pathway

Figure 15A:
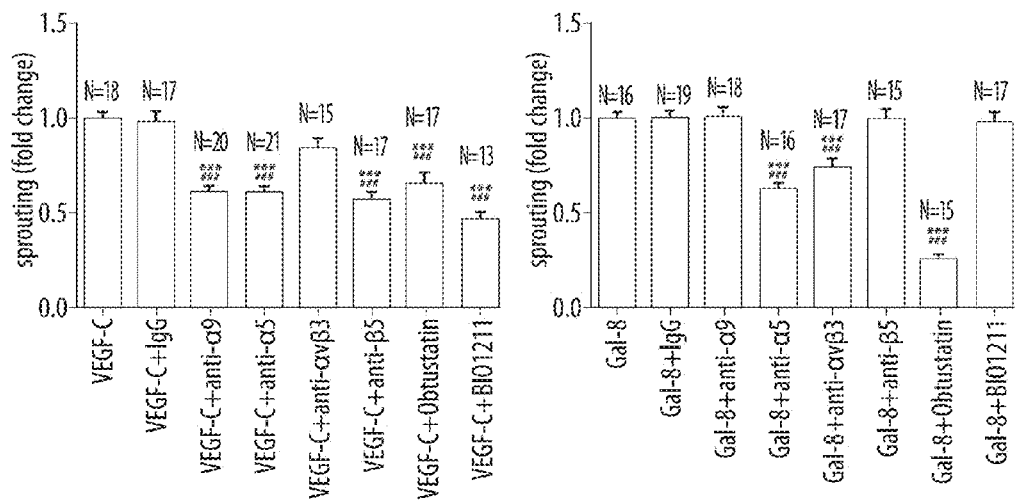
FIG. 15A-FIG. 15D are bar graphs, photomicrographs and photographs showing that Integrins regulate galectin-8-mediated lymphangiogenesis and are affected by the absence of PDPN.
Figure 15B:
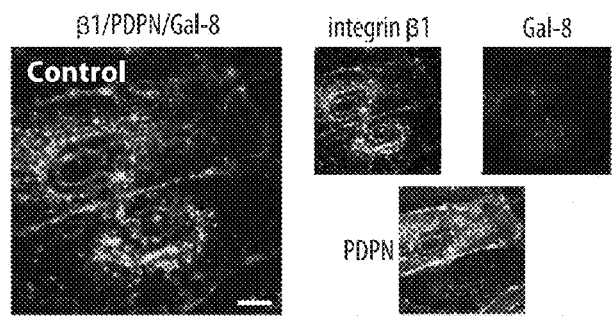
Figure 25A:
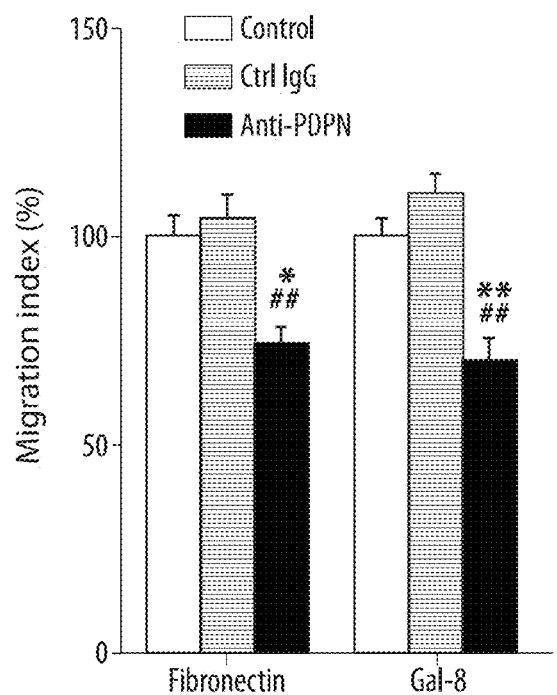
FIG. 25A-FIG. 25B are bar graphs showing that matrix-mediated LEC migration is dependent on PDPN.
Figure 25B:
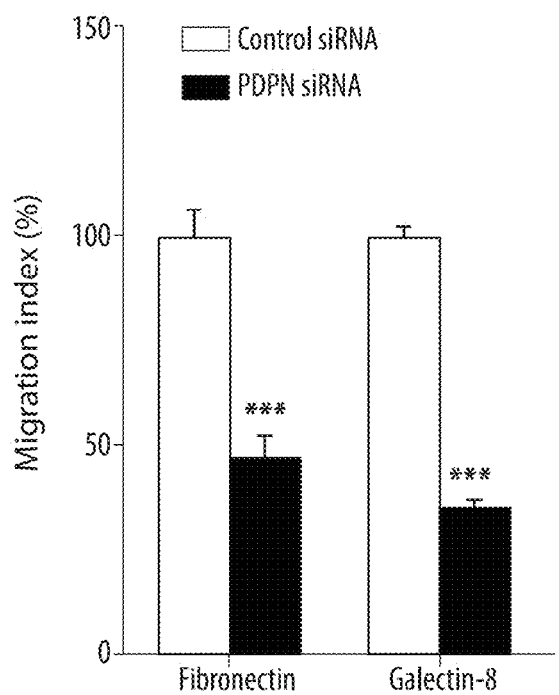

In addition to α9β1 integrin, several other integrins including α1β1, α4β1 and α5β1 are involved in the process of lymphangiogenesis (reviewed in Chen et al., 2012. International journal of cell biology 2012, 853703) and the interplay between integrin β1 and VEGFR-3 has been reported (Wang, J. F., et al., 2001. *Journal of biological chemistry* 276, 41950-41957: Zhang, X., et al., 2005. *Journal of cellular physiology* 202, 205-214). Therefore, to determine whether galectin-8-PDPN lymphangiogenic pathway involves specific integrins, LEC spheroids were treated with galectin-8 or VEGF-C in the presence or absence of blocking antibodies and peptides against a panel of integrins including anti-integrin α5 (clone NKI-SAM-1), anti-integrin αvβ3 (clone 23C6), anti-integrin β5 (clone KN52), Obtustatin (a blocking peptide against integrin α1β1) and BIO1211 (a blocking peptide against integrin α4β1). Data from this assay show that only blocking of integrins α1β1 (by Obtustatin) and α5β1 (by the neutralizing antibody) inhibited both VEGF-C- and galectin-8-induced LEC sprouting (FIG. 15A). To determine whether PDPN indirectly regulates the functions of VEGF-C/VEGFR-3 through controlling the function of integrins α1β1 and α5β1 in galectin-8-dependent manner, assays were performed to determine whether: (i) PDPN inhibition attenuates matrix mediated LEC migration, a process in which integrin-mediated cell-matrix interactions play a key role, (ii) PDPN interacts with integrins in a galectin-8-dependent manner, and (iii) knockdown PDPN impedes integrin-mediated signaling cascades. In this assay, blocking the function of PDPN by antibodies or by siRNA knockdown attenuated both fibronectin and galectin-8 promoted cell migration (FIG. 25). These data in conjunction with a published study (Cueni, L. N. et al. 2010. Blood 116, 4376-4384) indicate that PDPN-Fc inhibits type I collagen-mediated cell migration and that PDPN is involved in galectin-8 and in fibronectin- and type I collagen-mediated LEC migration, a process in which integrins are well-known to play a key role.

To assess the galectin-8-dependent interaction between integrins and PDPN, primary LECs were treated with galectin-8 for 15 minutes, fixed without permeabilization, stained with anti-integrin β1, PDPN and galectin-8 antibodies, and examined by confocal microscopy. In control cells incubated with buffer only, both integrin β1 and PDPN were observed to be homogenously distributed all over the LECs; endogenous galectin-8 was detected all over the cells (FIG. 15B) and in some cell-free areas which presumably are in the extracellular matrix.

Figure 15C:
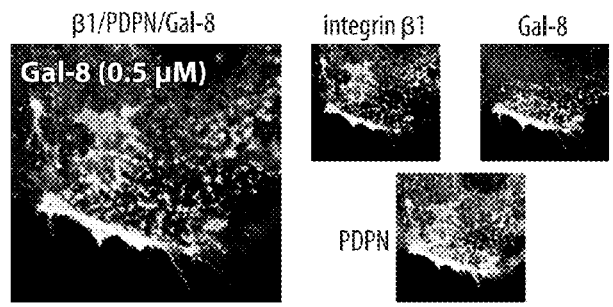
Figure 15D:
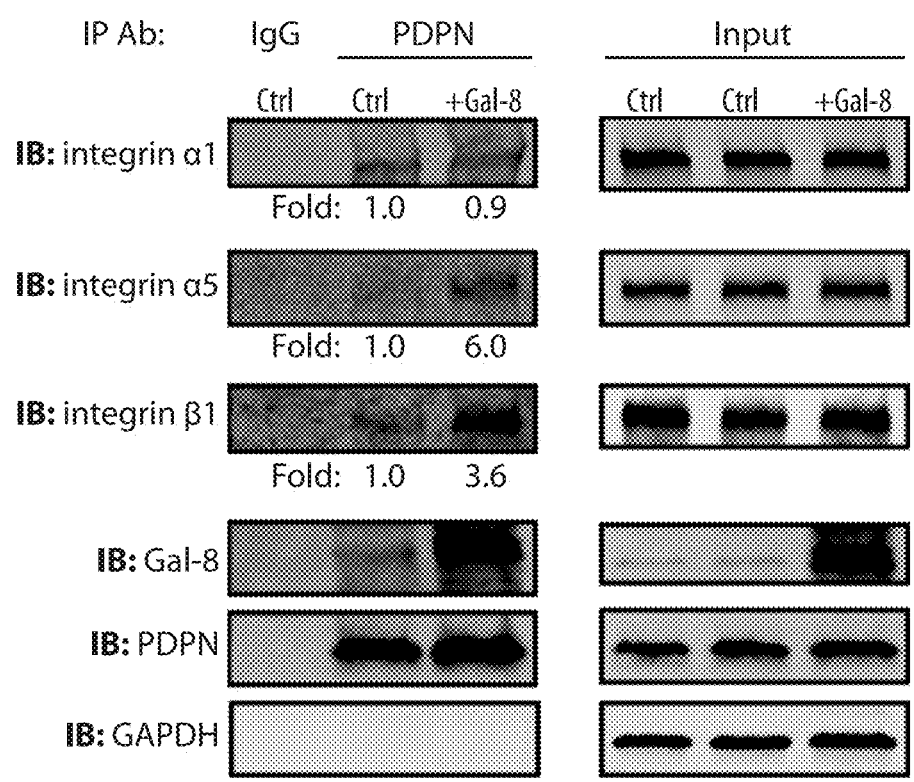
Figure 17A:
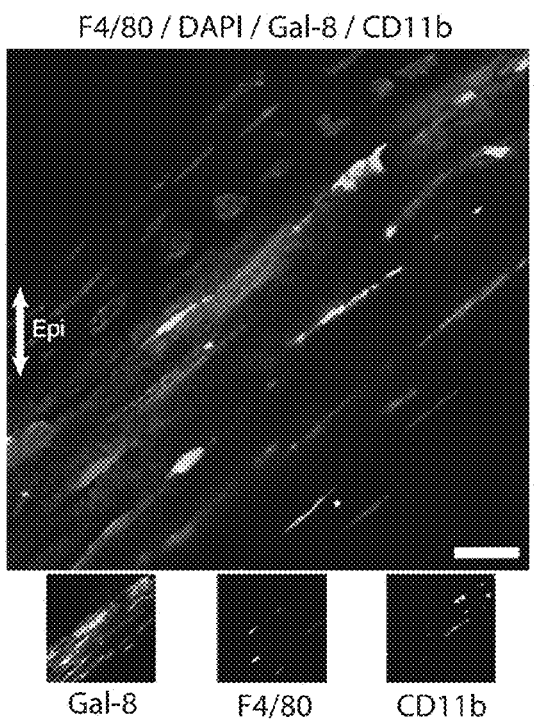
FIG. 17A-FIG. 17D are photomicrographs showing immunolocalization of galectin-8 with infiltrating immune cells in mouse corneas. Frozen sections of thermal cauterized mouse corneas on postoperative day one (FIG. 17A) and rejected mouse corneal allografts on postoperative week four (FIG. 17B-FIG. 17D) were fixed in 4% paraformaldehyde/PBS; and were permeabilized with 0.3% Triton X-100/PBS; and were stained with anti-galectin-8, biotinylated anti-Ly6G; and were incubated as indicated with Alexa Fluor 488-labeled F4/80 (green), Alexa Fluor 488-labeled CD4 (green), Alexa Fluor 647-labeled CD11b (cyan), Alexa Flour 647-labeled CD45 (cyan), Alexa Fluor 488-labeled streptavidin (green) and Alexa Fluor 568-labeled anti-rabbit IgG (red). Nuclei were counterstained with DAPI (blue). It was observed that macrophages and a subset of dendritic cells were positively stained with anti-F4/80 and anti-CD11b, and most of the F4/80+ cells were CD11b$^{dim}$ (FIG. 17A-FIG. 17B); neutrophils were stained positively with anti-Ly6G and anti-CD11b (FIG. 17C); CD4+ T cells were stained positively with anti-CD4 and anti-CD45 (FIG. 17D). The white asterisk indicates a F4/80+ but galectin-8-cell. Scale: 10 µm. Epi: epithelium.
Figure 17B:
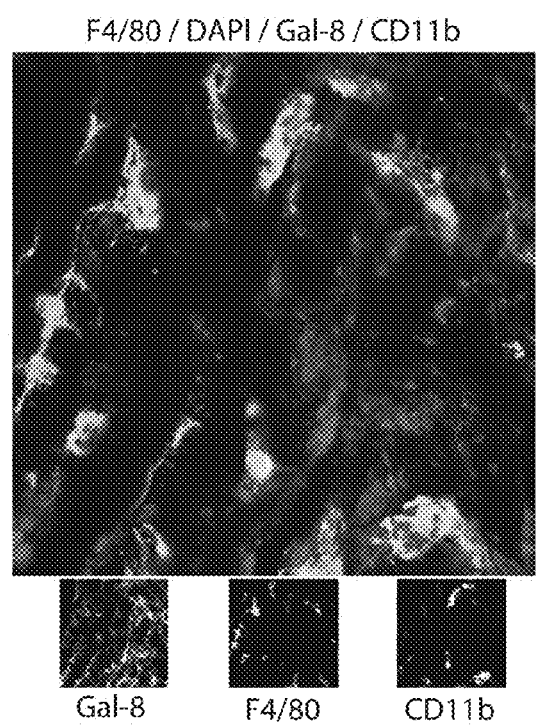
Figure 17C:
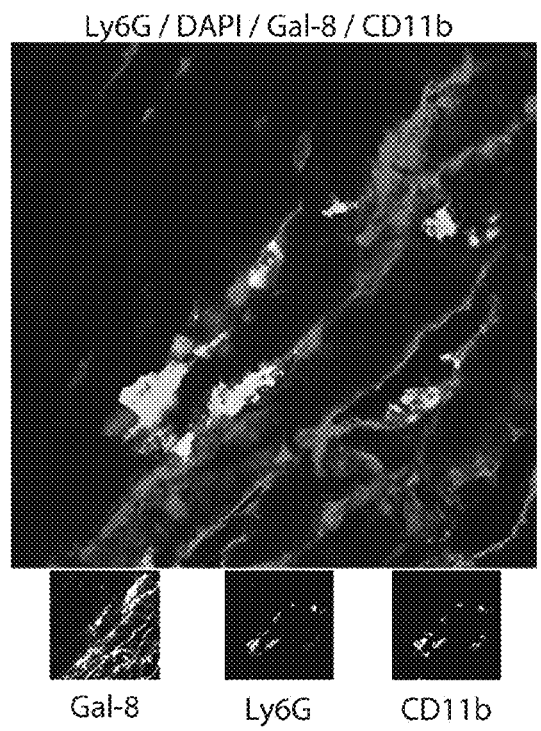
Figure 17D:
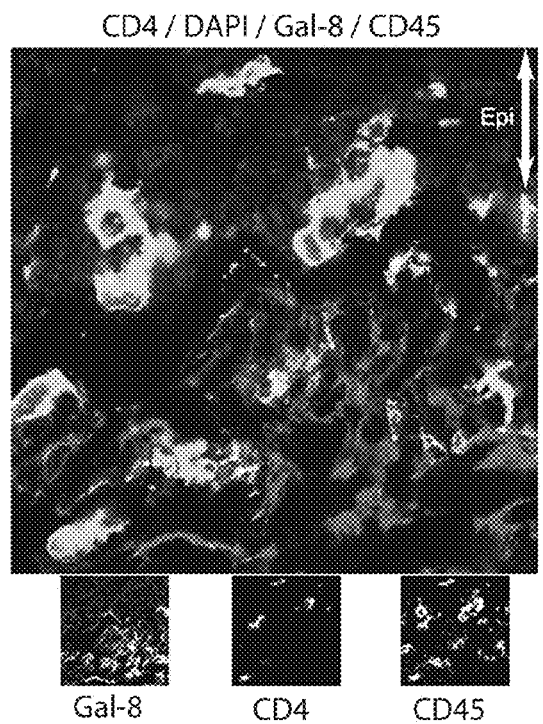
Figure 18A:
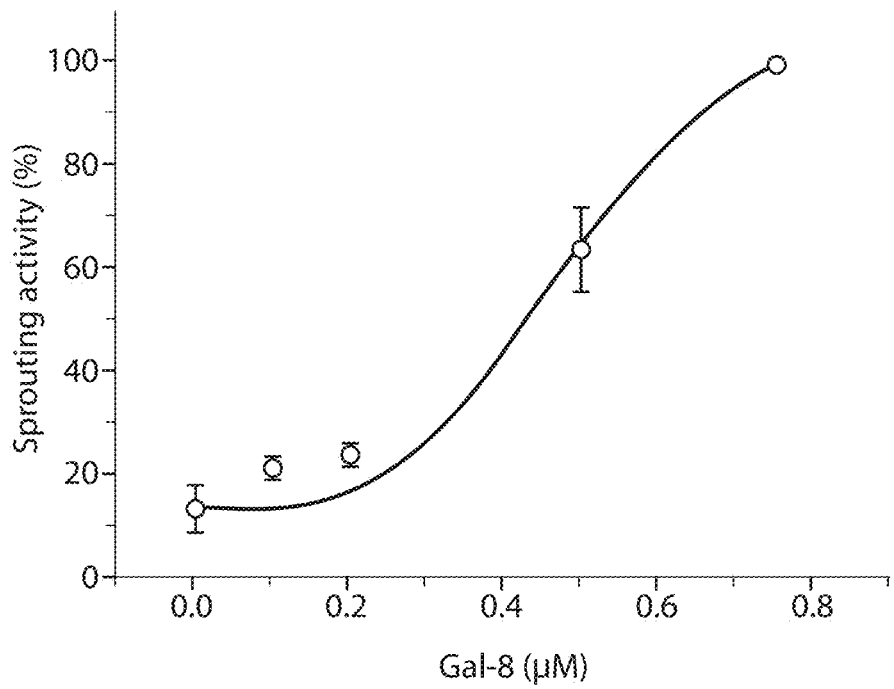
FIG. 18A and FIG. 18B are line graphs showing that galectin-8 stimulates LEC sprouting in a positively cooperative manner.
Figure 18B:
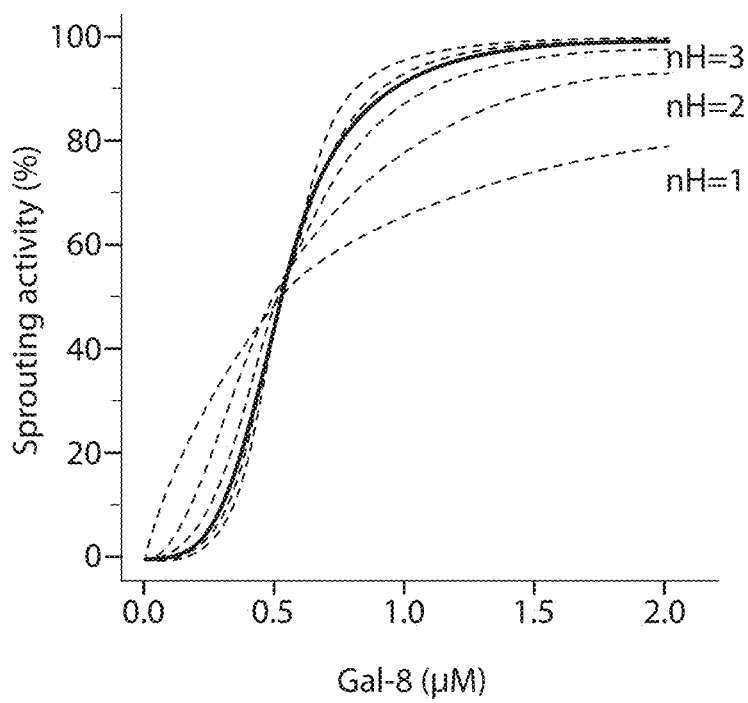
Figure 19A:
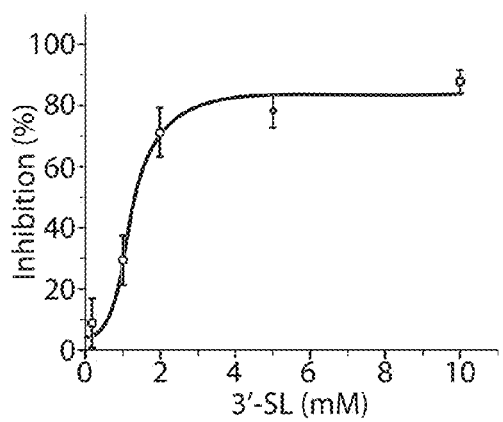
FIG. 19A-FIG. 19F are line graphs showing kinetic characteristics of inhibitory effect of 3'-SL and Gal-8N on galectin-8-mediated LEC sprouting.
Figure 19B:
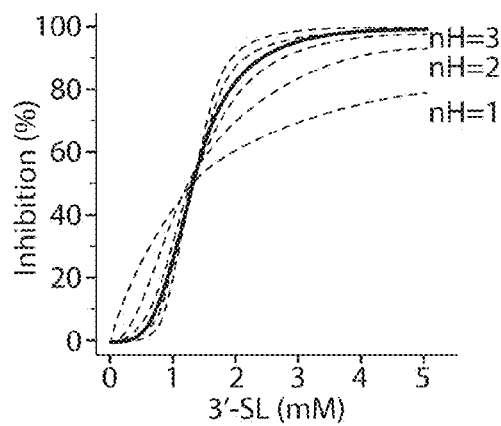
Figure 19C:
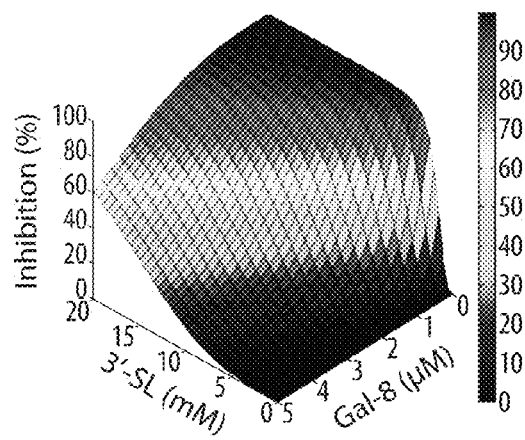
Figure 19D:
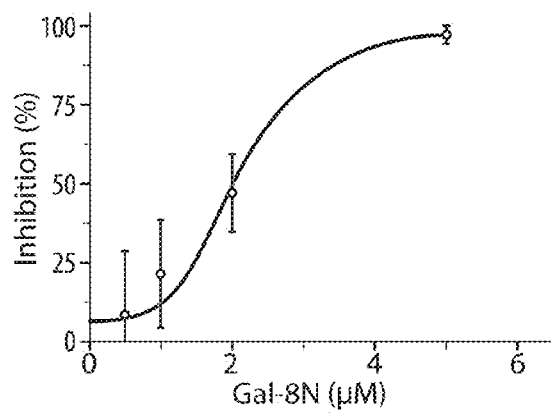
Figure 19E:
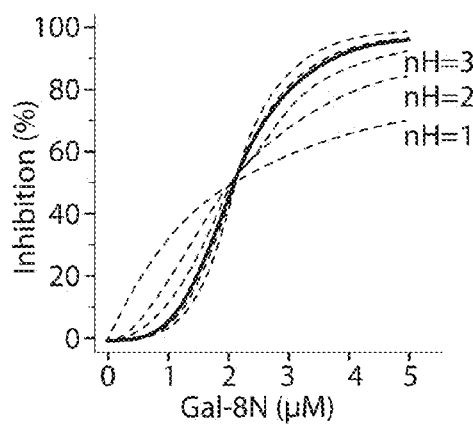
Figure 19F:
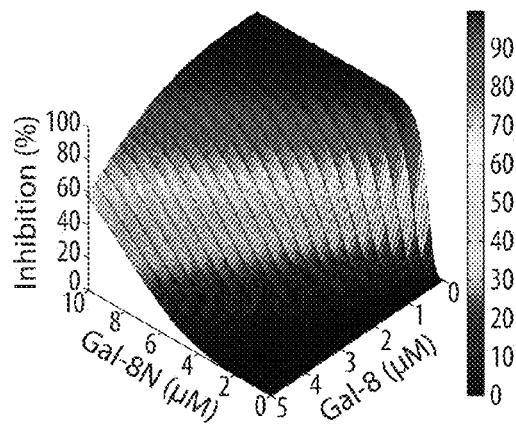
Figure 20A:
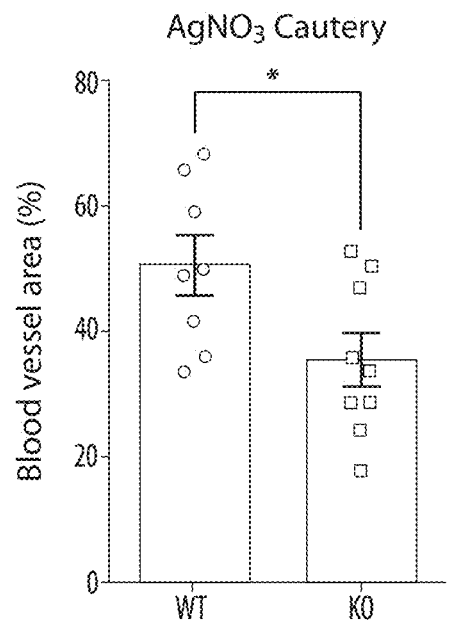
FIG. 20A-FIG. 20D are bar graphs and photomicrographs showing that silver nitrate cautery-induced inflammatory lymphangiogenesis is reduced in galectin-8 KO mice compared to WT. Silver nitrate cautery was introduced in the center of the corneas of the WT galectin-8+/+ and the KO galectin-8-/- mice. At the end of the treatment period (day seven), blood and lymphatic vessel areas were quantified (FIG. 20A-FIG. 20B). Representative images of WT (FIG. 20C) and galectin-8 KO (FIG. 20D) are shown. Anti-CD31: green; anti-LYVE-1: red. Data are plotted as mean±SEM and analyzed using Student's t test.
Figure 20B:
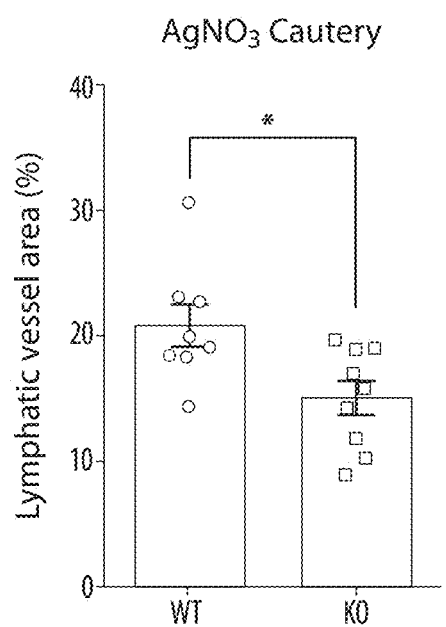
Figure 20C:
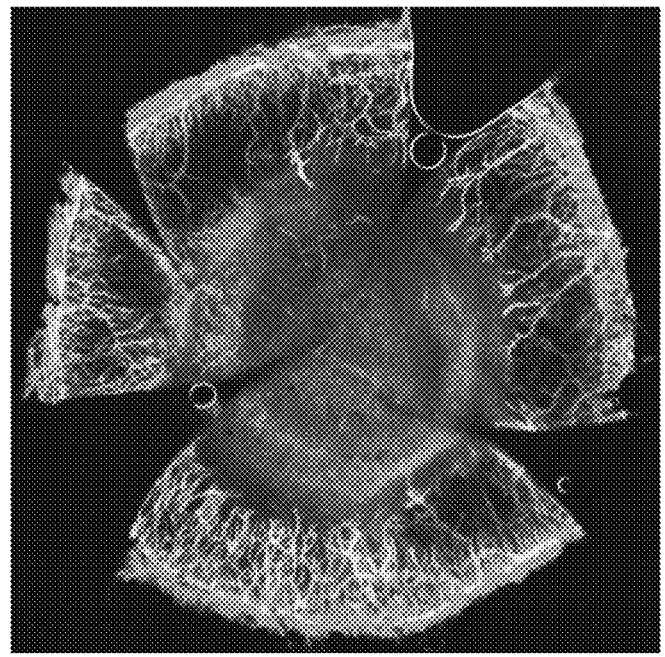
Figure 20D:
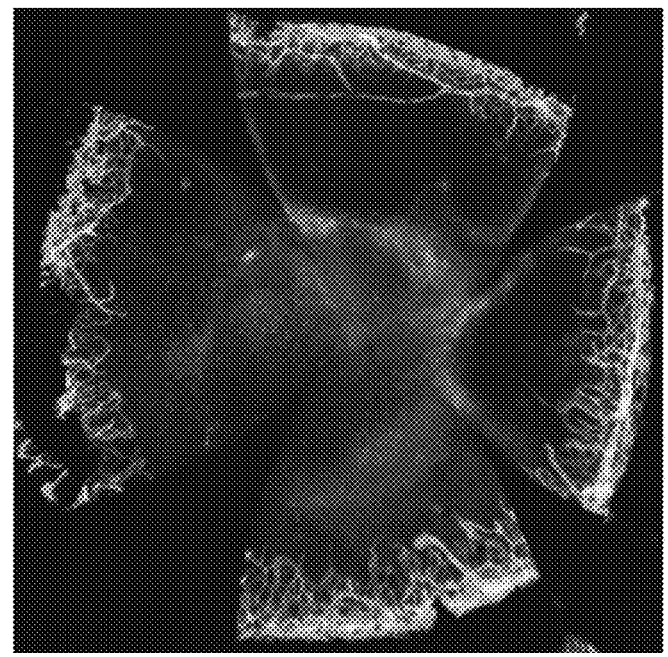

Since it was determined in data obtained from examples herein that galectin-8 was upregulated in inflamed human and mouse corneas (FIG. 1), exogenous galectin-8 was added to observe whether galectin-8 changes the distribution of PDPN and/or integrin β1 on LECs. Addition of galectin-8 was observed to have caused dramatic redistribution and clustering of PDPN and integrin β1 on LEC plasma membrane (FIG. 15C). To more directly assess the association between integrins and PDPN, lysates from untreated or galectin-8-treated LECs were incubated with anti-PDPN antibody, and immunoprecipitated proteins were examined by western blotting using antibodies against integrins β1, α1, α5, galectin-8 and PDPN. In untreated cell lysates, immunoprecipitation of anti-PDPN co-immunoprecipitated PDPN, endogenous galectin-8 and integrin α1β1, indicating that PDPN interacted with endogenous galectin-8 and the association between PDPN and integrin α1β1 was constitutive (FIG. 15D). Cells treated with exogenous galectin-8 were observed to have an increased association between PDPN and integrin α5β1 and the association between PDPN and integrin α1β1 remained similar (FIG. 15D).

Figure 26:
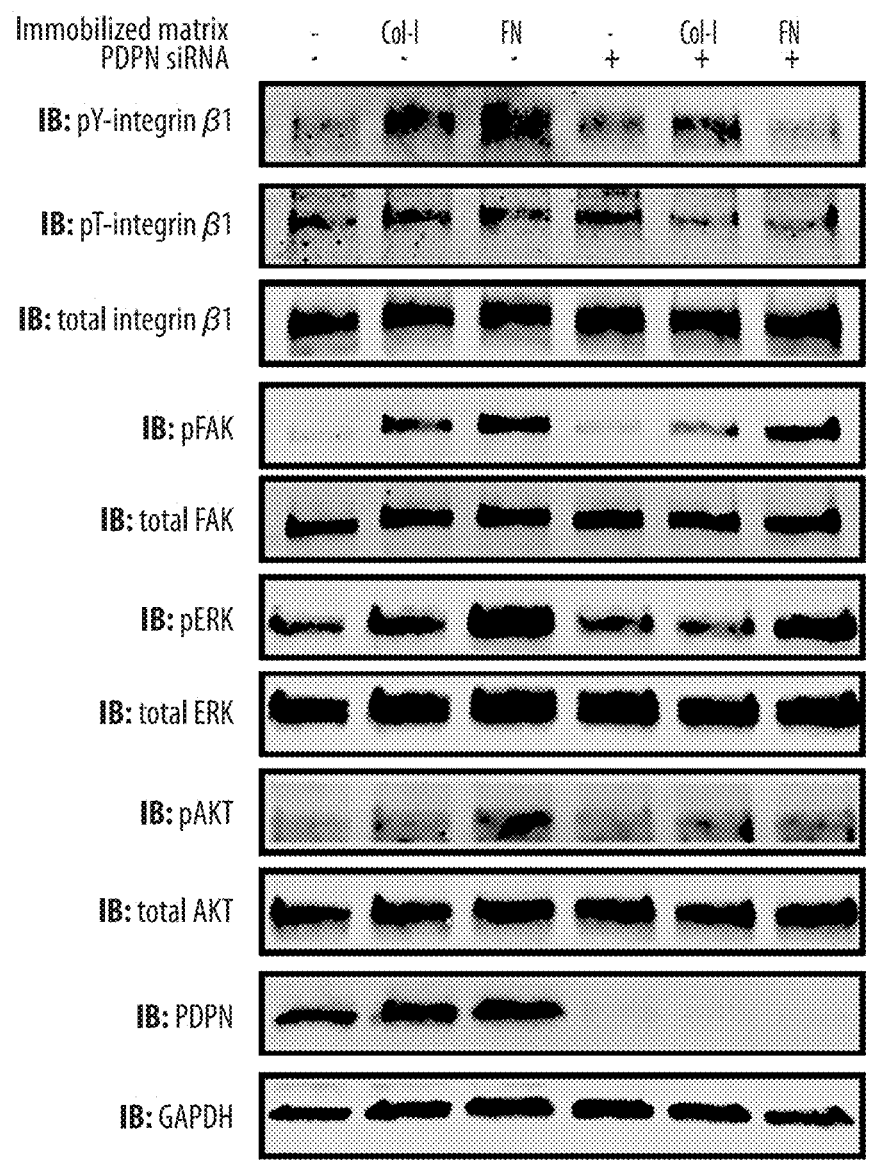
FIG. 26 is a photograph of western blots showing that PDPN modulates integrin-mediated signaling. LECs were transfected with control or PDPN pooled siRNA. The cells were detached 48 hours post-transfection and stimulated with immobilized collagen I (4 μg/cm$^2$) or fibronectin (2 μg/cm$^2$), or left in suspension for 15 min at 37° C. Cell lysates were subjected to electrophoresis and western blotting with antibodies described in examples herein.

Next, the role of PDPN on integrin-mediated signaling was assessed by transfecting LECs with control or PDPN pooled siRNA and seeding on collagen I- or fibronectin-coated wells incubated to adhere for 15 min at 37° C. Unattached cells were removed and cell lysates from attached cells on collagen I or fibronectin were analyzed by western blotting using phospho-specific integrin and focal adhesion kinase (FAK) antibodies. Phosphorylation of integrin β1 at residues Tyr783 and Thr788/789 was observed to be reduced in PDPN-knocked down cells in comparison to corresponding controls (FIG. 26), indicating that the activation of integrin β1 is reduced in the absence of PDPN. Also, phosphorylation of FAK at the residue Tyr397 was observed to be decreased in the PDPN-knocked down cells seeded on collagen I coated wells and the phosphorylation was observed to have remained the same in fibronectin-coated wells (FIG. 26). Additionally, phosphorylation of ERK at residues Thr202/Tyr204 was observed to be markedly reduced in the PDPN-knocked down cells seeded on both matrix proteins (FIG. 26). Taken together, these data conclude that PDPN regulates the functions of integrin β1 complexes, specifically of integrins α1β1 and α5β1 in LECs, and that this function is galectin-8 dependent.

What is claimed is:

1. A method for treating or preventing lymphangiogenesis in a subject, the method comprising:
    selecting an inhibitor of a galectin-8 protein or a portion thereof, wherein the inhibitor is a dominant negative inhibitor or a saccharide inhibitor selected from Thymine DNA glycosylase (TDG), 3'-sialyl lactose, and *Maackia amurensis* II (MAA II);
    administering a therapeutically effective amount of a pharmaceutical composition to the subject, wherein the composition comprises the inhibitor; and,
    measuring a decrease in a lymphangiogenesis marker in the subject.

2. The method according to claim 1 further comprising, analyzing an amount or an activity of at least one of the lymphangiogenesis marker selected from: podoplanin (PDPN),LYVE-1, PROX-1, desmoplakin, VECGF-C, VEGF-D receptor, and VEGFR-3.

3. The method according to claim 2, wherein analyzing further comprises measuring the treating or the preventing of lymphangiogenesis in the subject.

4. The method according to claim 1 further comprising, measuring interaction between at least two of the following: galectin-8 protein, VEGFR-3, and PDPN.

5. The method according to claim 4 further comprising, measuring binding of the composition to the galectin-8 protein thereby modulating a VEGF-C/VEGF receptor-3 pathway and/or a PDPN pathway in the subject.

6. The method according to claim 1 wherein the lymphangiogenesis is associated with a cancer, a corneal injury, a dry eye disease, an inflammation, a lymphedema, or a graft rejection.

7. The method according to claim 1, wherein administering further comprises topical delivery or transscleral delivery by a route selected from the group of: passive diffusion, osmotic pump, iontophoresis, ocular implant, or controlled release device.

* * * * *

UNITED STATES PATENT AND TRADEMARK OFFICE
CERTIFICATE OF CORRECTION

PATENT NO. : 10,226,509 B2  
APPLICATION NO. : 15/389509  
DATED : March 12, 2019  
INVENTOR(S) : Panjwani et al.

Page 1 of 1

It is certified that error appears in the above-identified patent and that said Letters Patent is hereby corrected as shown below:

In the Claims

Claim 2, Column 45, Line 64, insert a space after "(PDPN),"

Claim 2, Column 45, Line 64, strike out the first occurrence of the letter "C" in "VECGF-C"

Signed and Sealed this  
Thirtieth Day of April, 2019

Andrei Iancu  
*Director of the United States Patent and Trademark Office*